United States Patent
Morin-Aldebert et al.

(10) Patent No.: US 11,415,513 B2
(45) Date of Patent: Aug. 16, 2022

(54) METHOD FOR DETERMINING THE DEGREE OF SENSITIVITY OF A STRAIN OF FUNGUS TO AN ANTIFUNGAL AGENT

(71) Applicants: UNIVERSITE GRENOBLE ALPES, Saint Martin D'heres (FR); CENTRE HOSPITALIER UNIVERSITAIRE DE GRENOBLE, Grenoble (FR)

(72) Inventors: Delphine Paule Renee Morin-Aldebert, Grenoble (FR); Murielle Monique Jacqueline Cornet-Gigou, Saint-Ismier (FR)

(73) Assignees: UNIVERSITE GRENOBLE ALPES, Saint Martin d'Heres (FR); CENTRE HOSPITALIER RÉGIONAL DE GRENOBLE, La Tronche (FR)

( * ) Notice: Subject to any disclaimer, the term of this patent is extended or adjusted under 35 U.S.C. 154(b) by 868 days.

(21) Appl. No.: 15/744,682

(22) PCT Filed: Jul. 15, 2016

(86) PCT No.: PCT/FR2016/051832
§ 371 (c)(1),
(2) Date: Jan. 12, 2018

(87) PCT Pub. No.: WO2017/009585
PCT Pub. Date: Jan. 19, 2017

(65) Prior Publication Data
US 2018/0266952 A1 Sep. 20, 2018

(30) Foreign Application Priority Data
Jul. 15, 2015 (FR) ...................................... 15/01489

(51) Int. Cl.
G01N 21/64 (2006.01)
C12Q 1/18 (2006.01)
C12N 1/14 (2006.01)
C12Q 1/02 (2006.01)
G01N 33/50 (2006.01)
G01N 33/569 (2006.01)
G01N 33/58 (2006.01)
G01N 21/47 (2006.01)

(52) U.S. Cl.
CPC ............. *G01N 21/64* (2013.01); *C12N 1/14* (2013.01); *C12Q 1/02* (2013.01); *C12Q 1/18* (2013.01); *G01N 33/5008* (2013.01); *G01N 33/56961* (2013.01); *G01N 33/582* (2013.01); *C12Q 2304/00* (2013.01); *G01N 2021/4766* (2013.01); *G01N 2333/37* (2013.01); *G01N 2400/28* (2013.01)

(58) Field of Classification Search
CPC combination set(s) only.
See application file for complete search history.

(56) References Cited

U.S. PATENT DOCUMENTS 9,632,085 B2  4/2017  Super et al.

FOREIGN PATENT DOCUMENTS

| CN | 104284984 A | 1/2015 |
|---|---|---|
| FR | 2 863 273 A1 | 6/2005 |
| WO | 95/06132 A2 | 3/1995 |
| WO | 95/06132 A3 | 4/1995 |
| WO | 2013/130875 A1 | 9/2013 |

OTHER PUBLICATIONS

Walk et al., Antimicrobial Agents and Chemotherapy, 57: 146-154, 2013. (Year: 2013).*
Ling et al., "Evaluation of the VITEK 2 System for Rapid Direct Identification and Susceptibility Testing of Gram-Negative Bacilli from Positive Blood Cultures", Journal of Clinical Microbiology, Oct. 2003, pp. 4705-4707, vol. 41, No. 10.
Costa-De-Oliveira et al., "Determination of Chitin Content in Fungal Cell Wall: An Alternative Flow Cytometric Method", Cytometry Part A, 2013, pp. 324-328, vol. 83A.
Walker et al., "Cell wall stress induces alternative fungal cytokinesis and septation strategies", Journal of Cell Science, 2013, pp. 2668-2677, vol. 126, No. 12.
Arendrupa et al., "Breakpoints for antifungal agents: An update from EUCAST focussing on echinocandins against *Candida* spp. and triazoles against *Aspergillus* spp."Drug Resistance Updates, 2013, pp. 81-95, vol. 16.
Maubon et al., "Resistance of *Candida* spp. to antifungal drugs in the ICU: where are we now?", Intensive Care Medicine, 2014, pp. 1241-1255, vol. 40, No. 9.
Roncero et al., "Isolation and Characterization of *Saccharomyces cerevisiae* Mutants Resistant to Calcofluor White", Journal of Bacteriology, 1988, pp. 1950-1954, vol. 170, No. 4.
Juchimiuk et al., "*Candida albicans* cis-prenyltransferase Rer2 is required for protein glycosylation, cell wall integrity and hypha formation", Fungal Genetics and Biology, 2014, pp. 1-12, vol. 69.
International Search Report, dated Oct. 7, 2016, from corresponding PCT application No. PCT/FR2016/051832.
French Search Report, dated Mar. 30, 2016, from corresponding FR application No. FR 15 01489.
Yu et al., "Advances in Dermatology and Venereology," Sep. 30, 1999, Henan Medical University Press, p. 148.

(Continued)

*Primary Examiner* — Allison M Fox
*Assistant Examiner* — Qing Xu
(74) *Attorney, Agent, or Firm* — Nixon & Vanderhye

(57) ABSTRACT

A method for determining the degree of sensitivity of a strain of fungus to an antifungal agent by using the possible change in a chitin level in a population of cells of a strain of fungus to an antifungal agent. The change is determined compared to the chitin level of a population of cells of said strain of fungus in the absence of antifungal agent.

9 Claims, 7 Drawing Sheets

(56) References Cited

OTHER PUBLICATIONS

Zhang et al., "The paradoxical effects of echinocandins," Chin J Infect Chemother, vol. 14, No. 5, pp. 442-445, Sep. 20, 2014.

* cited by examiner

Figure 1: Test of sensitivity of the strain SC5314 of *C. albicans* to fluconazole
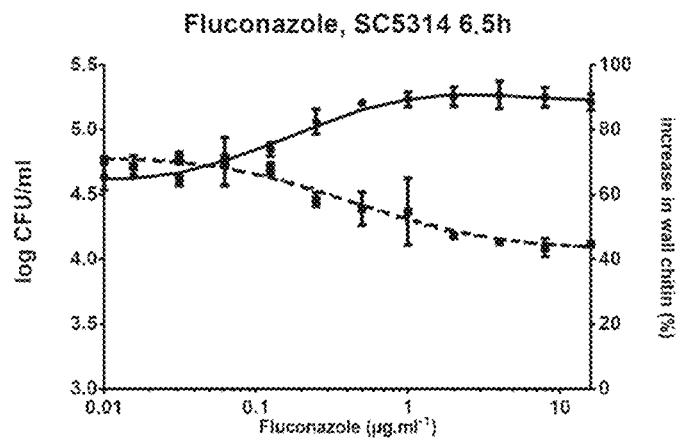
Figure 2: Test of sensitivity of the strain SC5314 of *C. albicans* to voriconazole
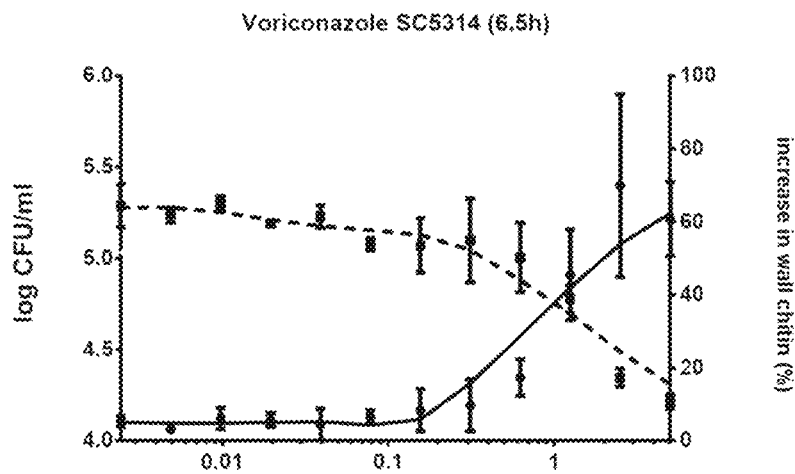
Figure 3: Test of sensitivity of the strain DSY296 of *C. albicans* to fluconazole
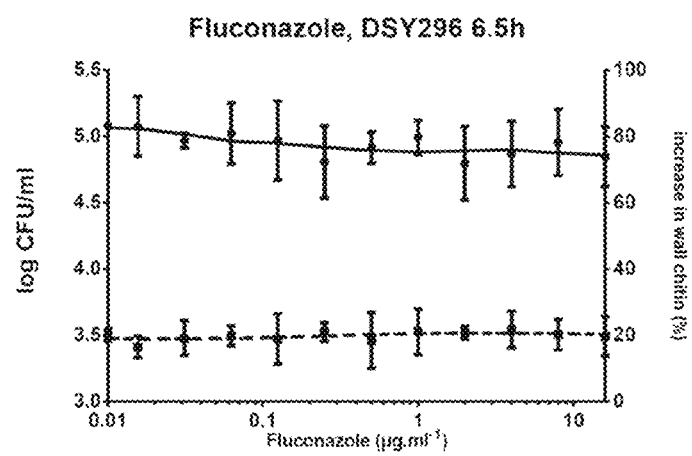

Figure 4: Test of sensitivity of the strain DSY296 of *C. albicans* to voriconazole
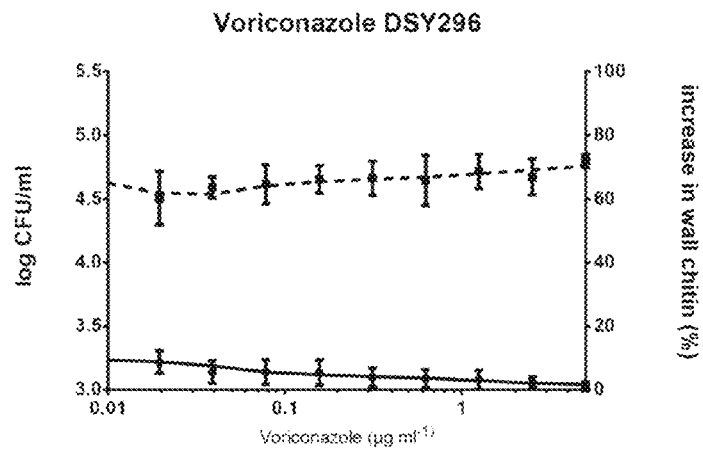
Figure 5: Test of sensitivity of the strain TOP of *C. albicans* to micafungin
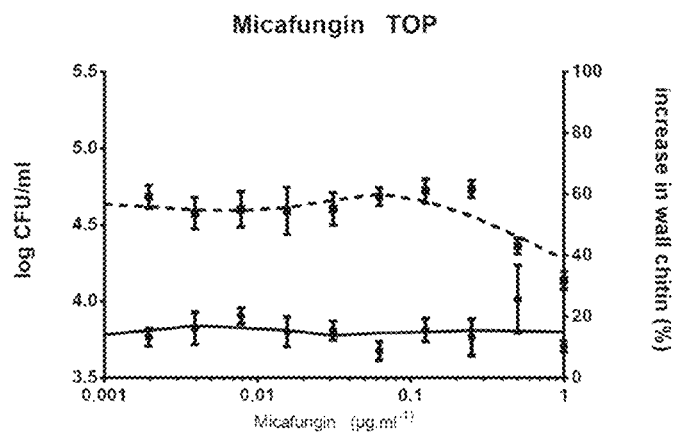
Figure 6: Test of sensitivity of the strain Tg5 of *C. glabrata* to fluconazole
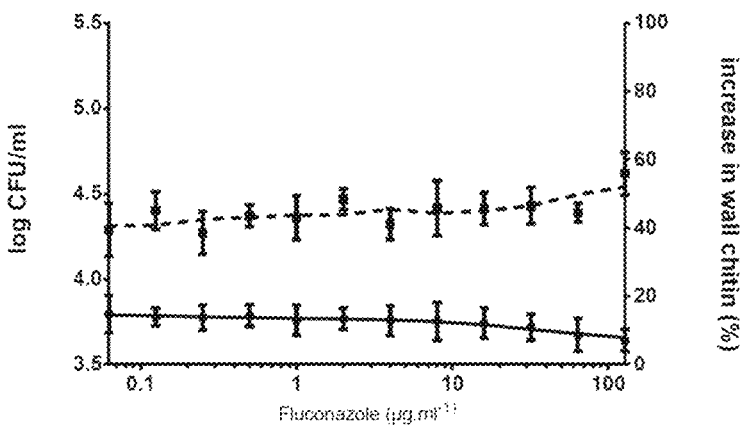

Figure 7: Test of sensitivity of the strain Tg5 of *C. glabrata* to voriconazole
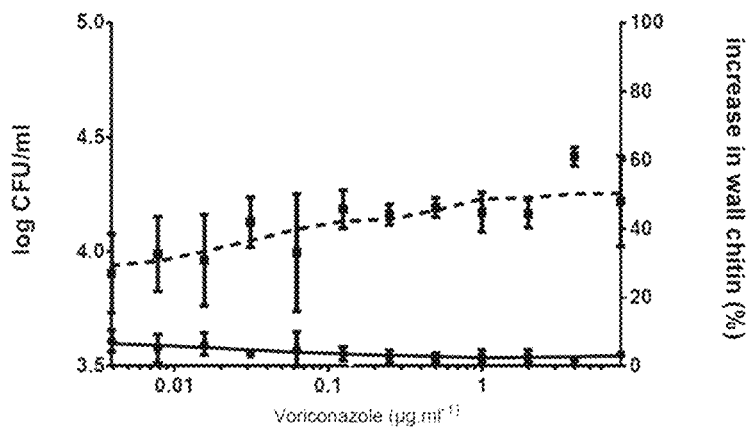
Figure 8: Test of sensitivity of the strain ATCC®7349 of *C. tropicalis* to fluconazole
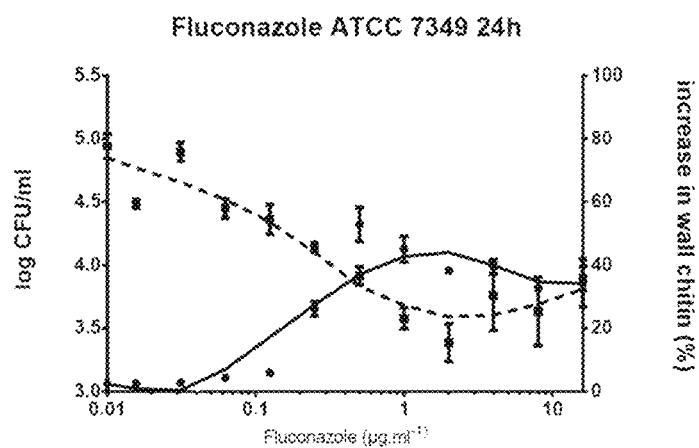
Figure 9: Test of sensitivity of the strain ATCC®7349 of *C. tropicalis* to voriconazole
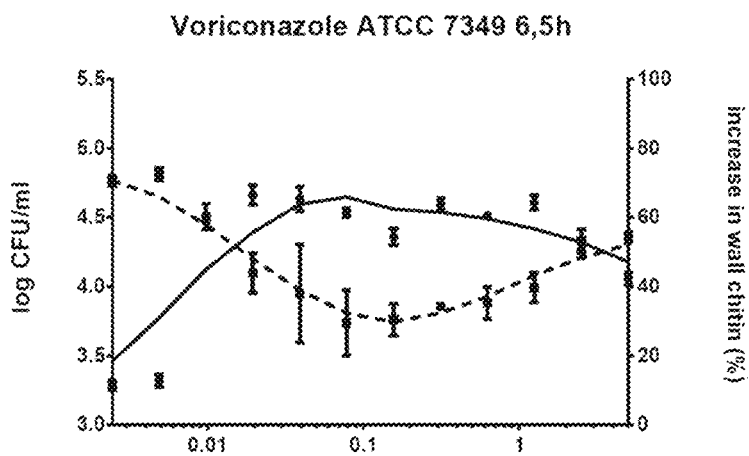

Figure 10: Test of sensitivity of the strain ATCC®7349 of *C. tropicalis* to micafungin
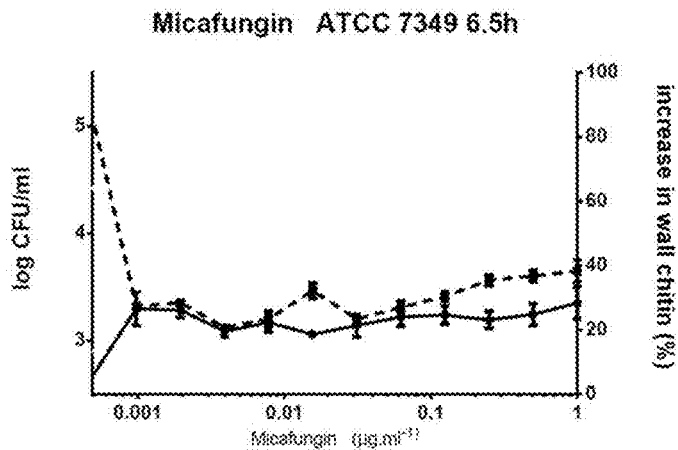
Figure 11: Test of sensitivity of the strain 13/5 of *C. tropicalis* to micafungin
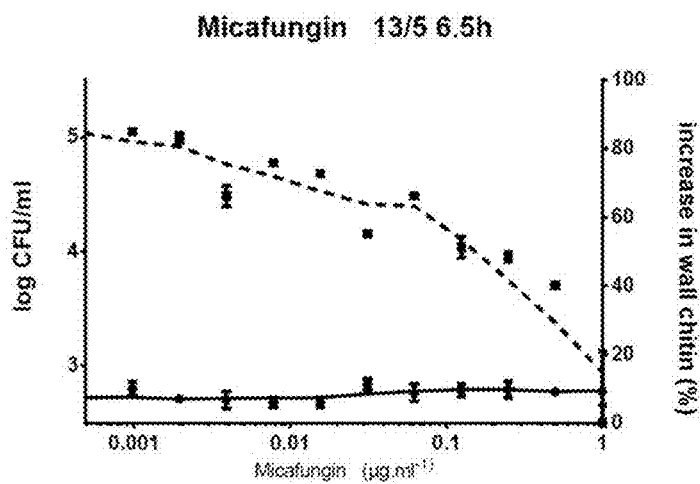
Figure 12: Test of sensitivity of the strain ATCC®22019 of *C. parapsilosis* to fluconazole
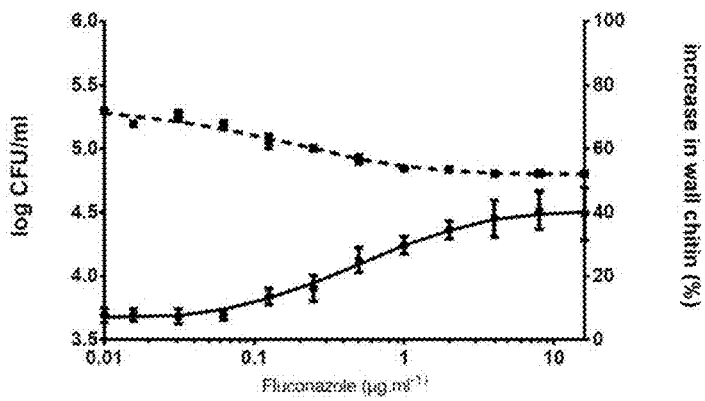

Figure 13: Test of sensitivity of the strain ATCC®22019 of *C. parapsilosis* to voriconazole
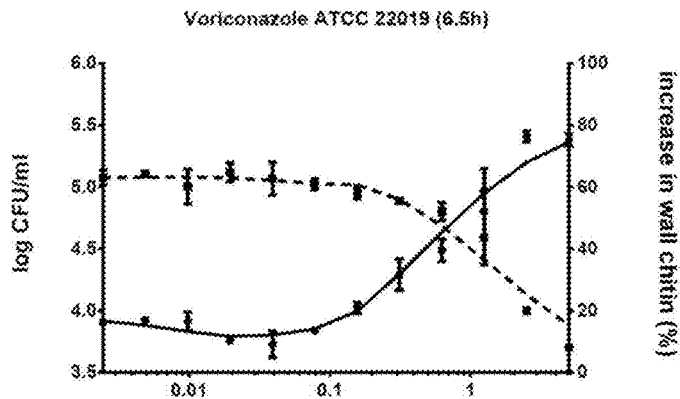
Figure 14: Test of sensitivity of the strain ATCC®22019 of *C. parapsilosis* to micafungin
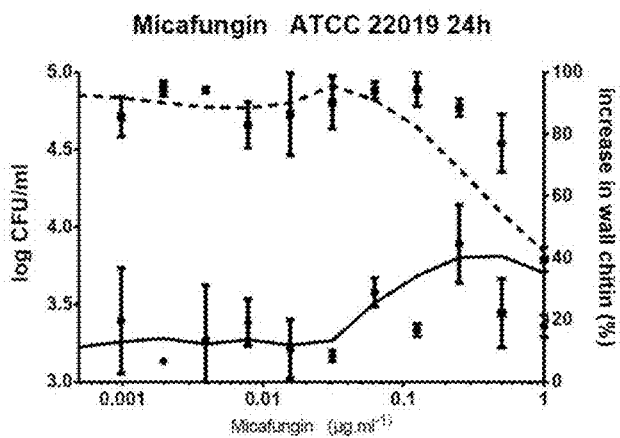
Figure 15: Test of sensitivity of the strain 8/21 of *C. parapsilosis* to fluconazole
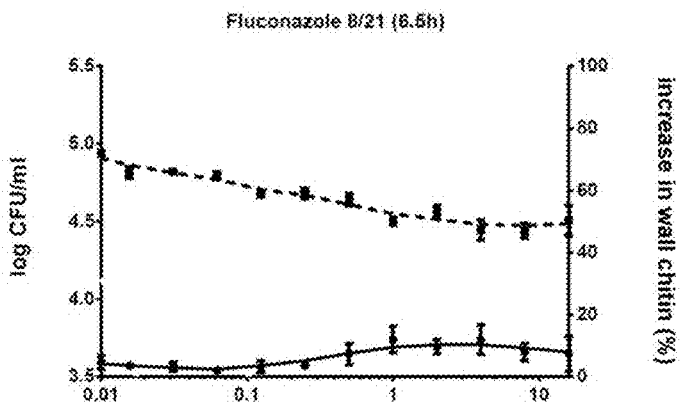

**Figure 16: Test of sensitivity of the strain 8/21 of *C. parapsilosis* to voriconazole**
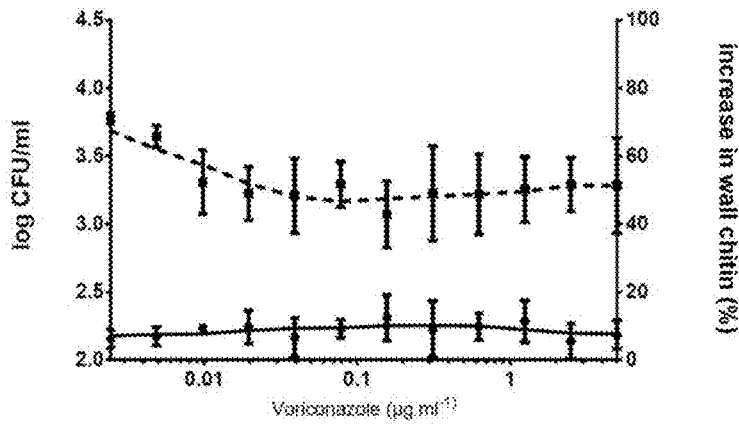
**Figure 17: Test of sensitivity of the strain ATCC®6258 of *C. krusei* to fluconazole**
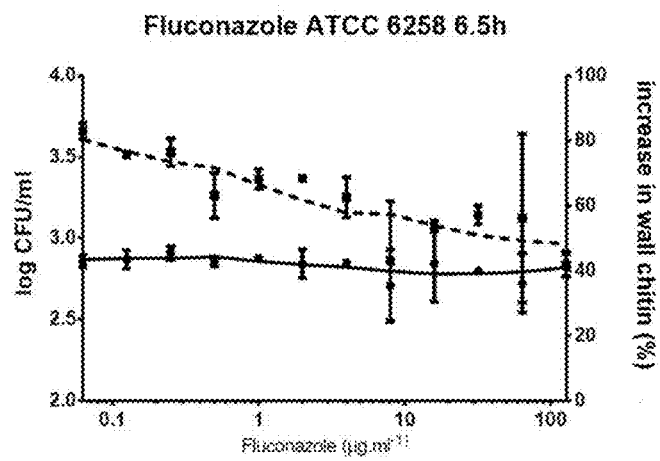
**Figure 18: Test of sensitivity of the strain ATCC®6258 of *C. krusei* to voriconazole**
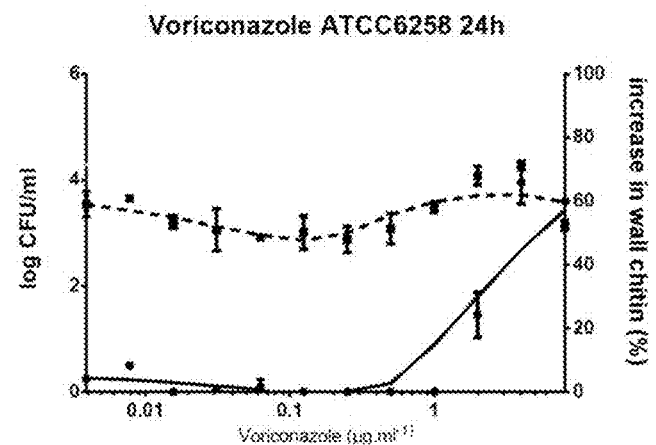

**Figure 19: Test of sensitivity of the strain GRE32 of *C. krusei* to fluconazole**
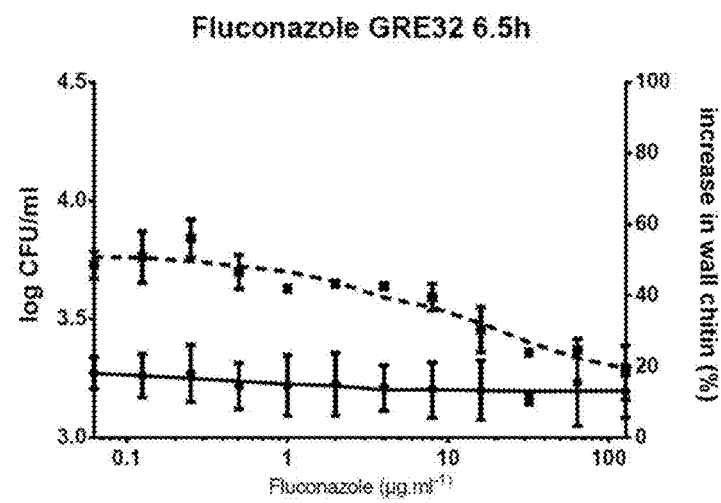
**Figure 20: Test of sensitivity of the strain GRE32 of *C. krusei* to voriconazole**
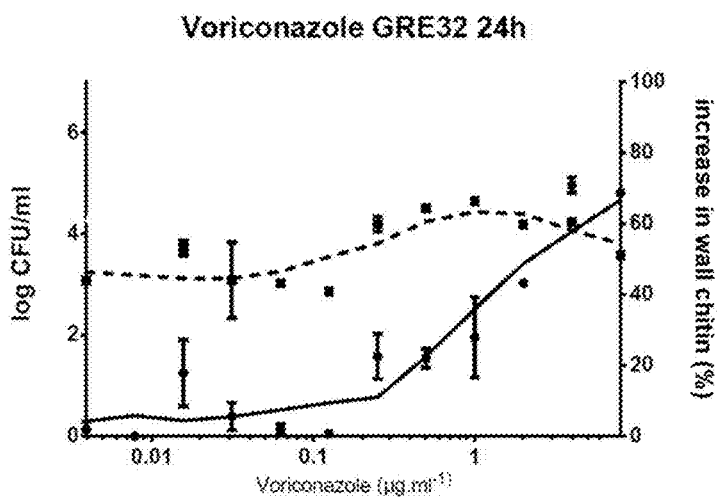

METHOD FOR DETERMINING THE DEGREE OF SENSITIVITY OF A STRAIN OF FUNGUS TO AN ANTIFUNGAL AGENT

The invention relates to a method for determining the degree of sensitivity of a strain of fungus to an antifungal agent.

Since the 1980s, fungi have been considered to be a major source of pathologies in humans.

Invasive candidiasis, caused by different species of yeast, is the fourth leading cause of nosocomial blood infections in the United States, and is associated with a mortality rate of approximately 40%. These septicaemia are primarily related to immunodeficiencies, or surgical or invasive procedures.

The increase in the appearance of strains resistant to antifungal molecules, especially among *Candida* spp. yeasts, is leading to an increase in clinical failures. The precise and rapid characterisation of resistant isolates has become a key concern in order to tailor the treatment based on the phenotype of the strain as soon as possible after the onset of infection.

The antifungal agent susceptibility tests that are currently available are based on the evaluation of the inhibition of fungus growth in the presence of an antifungal agent and make it possible to determine the minimum inhibitory concentration (MIC).

This value can then be interpreted in relation to clinical thresholds (clinical breakpoints, CBPs) defined by the Clinical and Laboratory Standards Institute (CLSI) and the European Committee on Antimicrobial Susceptibility Testing (EUCAST). These clinical thresholds make it possible to establish a sensitive, resistant or intermediate phenotype of the strain of fungus and so predict patient response to antifungal treatment in order to adapt it according to the phenotype of the infecting strain.

The CLSI or EUCAST reference methods for MIC determination are based on microdilution and are therefore unsuitable for routine clinical practice.

Other tests that are easier to implement have been developed and marketed for medical use. Fungitest™ (Biorad) is a method for determining the sensitivity of yeast strains produced from a cell suspension in the presence of six antifungal agents (amphotericin B, flucytosine, fluconazole, itraconazole, ketoconazole and miconazole) at two different concentrations. It is provided in the form of microplates comprising wells with said antifungal agents. It allows the determination of the sensitivity of the strain by colorimetric reading, after incubation between 48 and 72 h of the microplates and the placement in the presence of a redox indicator.

Sensititre Yeast One® (Trek Diagnostic Systems) is a method for in vitro diagnosis of the sensitivity of yeast strains, also including the species *Candida*, *Cryptococcus* and *Aspergillus* and developed for voriconazole, caspofungin, anidulafungin and micafungin. This method is provided in the form of microplates comprising wells and allows the determination of the MIC on the basis of microdilutions and with the aid of a colorimetric indicator after incubation of the microplate between 24 and 72 h depending on the species.

Etest® (Biomérieux) is a method for determining the MIC of microorganisms (bacteria, fungi) developed for more than 100 reference molecules including antibiotics, antifungal agents, antimycobacterial agents, and antimicrobial agents. It is provided in the form of strips having a predetermined exponential gradient of 15 concentrations of antifungal agent or antibiotic, which is applied to a seeded agar plate.

After incubation for about 24 h, the MIC value is determined visually by reading the value indicated on the strip and corresponding to the edge of the inhibition ellipse. This intersection between the ellipse of inhibition and the test strip indicates the concentration at which the tested molecule inhibits the growth of the microorganism. The Etest® method is the most used routinely because of its simple implementation.

Vitek 2 (Biomérieux) is an automated system for identifying bacteria or yeasts and for creating antibiograms from an inoculum in liquid medium, using plates of reaction wells comprising different colorimetric tests. It makes it possible both to identify the microorganism and to determine the MIC compared to one or more antifungal agents or antibiotics within 3 to 7 hours. (Ling et al., 2003, *Evaluation of the VITEK 2 System for Rapid Direct Identification and Susceptibility Testing of Gram-Negative Bacilli from Positive Blood Cultures*).

Methods using flow cytometry and the cell viability dyes have also been developed primarily for *Candida* spp. These have shown a good correlation with the CLSI and EUCAST reference methods, but only for a few specific antifungal agent-species pairings.

Chemical tests have been created with, for example, quantification of ergosterol synthesis.

Most marketed sensitivity tests are based on colorimetric tests or growth tests for determining the MIC of a given strain.

Visual interpretation of the results can be a source of error, knowing that the effect of lagging growth in the presence of azoles can also distort the interpretation of the test and corresponds to a minimum growth in the inhibition zone.

All existing tests have drawbacks, the biggest being the test response time (at least 24 h) and the subjectivity of the reading of the result.

The development of new, faster and more reliable tests enabling determination of the phenotype of a strain of fungus with respect to an antifungal agent in order to adapt the treatment as quickly as possible after the onset of infection is thus necessary due to the increased development of resistances of different fungus species.

Among the antifungal agents commonly used to form the basis of treatments, reference is made especially to the class of echinocandins, including micafungin, caspofungin and anidulafungin. This class of antifungal agents acts directly on the wall of fungi. These agents inhibit the synthesis of β-1,3-glucan of the cell wall by binding to the β-1,3-glucan synthase, an enzyme bound to the membrane and composed of regulatory subunits (Rho) and catalytic subunits (Fks), the inhibition of which thus causes inhibition of the formation of the wall.

The main alternative to echinocandins are antifungal agents that have inhibitory action with regard to the synthesis of sterols present in the cell membrane. Among these, the class of azoles or azole antifungal agents is distinguished, which includes especially fluconazole, posaconazole, voriconazole and itraconazole, which are the most commonly used. Azole antifungal agents target the cytochrome P450-Erg11p, also called Cyp51p, which is involved in the biosynthetic pathway of ergosterol, which is a major component of the fungal membrane. Blocking the pathway of ergosterol synthesis results in the production of toxic methylated sterols and damage in the cell membrane. Azoles have shown that they lead to an increase in production of proteins of the wall as a compensatory phenomenon, which suggests that azoles are not only membrane inhibitors but also cell wall inhibitors.

Polyenes, represented fundamentally by amphotericin B, have high toxicity; pyrimidines are also used as antifungal agents but usually in combination with an antifungal agent from another class because of the development of resistance to pyrimidine analogues.

The mechanism of action of azoles and echinocandins thus involves the membrane and/or cell wall. Some stress response signalling pathways such as those of PKC (protein kinase C), the HOG (high glycerol osmolarity) pathway, MAPK (MAP kinase) pathway, and the pathway of calcineurins are activated in response to wall stress and coordinate an increase in the synthesis of chitin to compensate for damage caused to the wall and/or cell membrane.

In the publication of Costa de Oliveira et al. (2013), the authors found that some species of yeast that have the ability to grow to high concentrations of caspofungin (above the MIC) also have a high amount of chitin in their cell wall.

Walker et al. (2013) described a paradoxical effect of fungus growth in the presence of echinocandins which occurs most frequently during treatment with caspofungin. They demonstrated that C. albicans growth is inhibited at low concentrations and at very high concentrations, but growth is observed at intermediate concentrations.

One aspect of the invention is to provide a reliable test for determining the degree of sensitivity of a strain of fungus.

Another aspect of the invention is to provide a reliable test for determining the degree of sensitivity of a strain of fungus, the response time of which is less than 48 h or 24 h, more especially 6.5 h.

Another aspect of the invention is to provide a reliable test for determining the degree of sensitivity of a strain of fungus, the interpretation of which is objective and is not subject to the lagging effect.

Another aspect of the invention is to provide a reliable test for determining the degree of sensitivity of a strain of fungus that can be used clinically.

The present invention relates to the use of the possible change in the chitin level in a population of cells of a strain of fungus to determine the degree of sensitivity of said strain of fungus to an antifungal agent, said change being determined in relation to the chitin level of a population of cells of said strain of fungus in the absence of antifungal agent.

The inventors have found that the possible change in the chitin level appears to make it possible to determine the sensitivity of a strain of fungus with respect to an antifungal agent.

The possible change in the chitin level used to determine the degree of sensitivity means that the chitin level can change, that is to say can increase or decrease, and that this change is possible however, which means that there may be a change in the chitin level or no change, depending on the conditions.

The inventors have thus demonstrated that a change or an absence of change in the chitin level in a population of cells of a strain of fungus in the presence of an antifungal agent compared to the same population of cells in the absence of antifungal agent was significant for determining the degree of sensitivity of this strain of fungus to this antifungal agent.

The degree of sensitivity of a strain of fungus to an antifungal agent corresponds to the ability of this antifungal agent to kill or sufficiently inhibit the growth of this strain.

The term "antifungal agent" means any molecule that helps fight against fungi. Antifungal agents may also be referred to as "antimycotic agents".

The invention relates to the determination of the degree of sensitivity of a strain of fungus to an antifungal agent, which means that the sensitivity of said strain is determined with respect to a single specific antifungal agent and not with respect to a mixture of antifungal agents.

In fungi, chitin is a major component of the wall that surrounds and protects the fungal cells with respect to the environment. Chitin also appears to contribute to the rigidity of the cell wall in fungi. Chitin is a nitrogen-containing polysaccharide of formula $(C_8H_{13}NO_5)_n$, of the carbohydrate family, derived from the polymerisation of N-acetyl-glucosamine linked together by a glycosidic bond of the β-1,4 type, and synthesised by a number of enzymes: chitin synthases (CHS).

The term "fungi" refers to multicellular or unicellular eukaryotic organisms which are motionless and feed by absorption of organic molecules directly in their environment. Fungus cells have the particular feature of the presence of a wall enclosing the chitin, and the absence of chlorophylls and/or of plastids because these organisms are heterotrophic with respect to carbon. The term "fungus" refers to the fungi kingdom.

The term "population of cells of a strain of fungus" refers to a homogeneous set of cells, that is to say having a homogeneity at genotype and phenotype level.

The term "absence of antifungal agent" means that the population of cells of the strain of fungus is in the absence of the antifungal agent tested within the scope of the determination of the degree of sensitivity of said strain of fungus, but is also in the total absence of any other molecule of the class of antifungal agents.

"Chitin level in a population of fungus cells" means the average amount estimated by the method explained below in a population of specific fungus cells.

The degree of sensitivity assesses the efficacy of the antifungal agent, that is to say the ability of the antifungal agent to inhibit the multiplication of the fungus or to kill the fungus in laboratory conditions mimicking the in vivo conditions.

Three categories were selected for the interpretation of degree of sensitivity in vitro: sensitive, resistant and intermediate.

According to an especial embodiment, the present invention relates to the use of the possible change in the chitin level in a population of cells of a strain of fungus to determine the degree of sensitivity of said strain of fungus to an antifungal agent, wherein the degree of sensitivity corresponds to a sensitive phenotype, or a resistant phenotype, or an intermediate phenotype of said strain of fungus with respect to an antifungal agent.

Strains categorised as sensitive are those for which the probability of therapeutic success is high (90%) in the case of a systemic treatment with the recommended dosage in the summary of product characteristics (SmPC), written by the French Agency for the Safety of Health Products (AFSSAPS).

Strains categorised as resistant are those for which there is a high probability (40%) of treatment failure regardless of the type of treatment and dose of antifungal agent used.

Strains categorised as intermediate are those for which therapeutic success is unpredictable. These strains form a heterogeneous set for which the results obtained in vitro are not predictive of therapeutic success. In fact, these strains:

May have a mechanism of resistance of which the expression in vitro is low, resulting in their classification in the sensitive category. However, in vivo, some of these strains appear resistant to treatment and lead to treatment failure;

May have a mechanism of resistance of which the expression is not sufficient to justify a classification in the resistant category, but is low enough to expect a therapeutic effect in certain conditions (high local concentrations or increased doses).

Fungi are organisms that can be multicellular or unicellular.

In an especial case, fungi can be unicellular and their vegetative system then consists of a single cell.

According to an especial embodiment, the present invention relates to the use of the possible change in the chitin level in a population of cells of a strain of fungus to determine the degree of sensitivity of said strain of fungus to an antifungal agent, wherein the fungus is an unicellular fungus.

Other fungi are multicellular, and their multicellular vegetative system appears similar to filaments, called hyphae, hence the name of filamentous fungi to denote multicellular fungi. These hyphae may be branched to a greater or lesser extent and interleaved with each other. The totality of hyphae form the mycelium.

According to an especial embodiment, the present invention relates to the use of the possible change in the chitin level in a population of cells of a strain of fungus to determine the degree of sensitivity of said strain of fungus to an antifungal agent, wherein the fungus is a multicellular fungus.

To determine the degree of sensitivity of a strain to an anti-fungal agent the growth parameter of said strain of fungus may be taken into account in addition to the possible change in the chitin level.

In the case of determining the degree of sensitivity of a strain of unicellular fungus, cells of said strain constitute the living material on the basis of which the degree of sensitivity is determined.

Thus, in the case of a strain of unicellular fungus, the growth of said strain is assessed by quantifying the number of cells of said strain of fungus in the medium.

According to an especial embodiment, the present invention relates to the use of the possible change in the chitin level in a population of cells of a strain of fungus, said fungus being an unicellular fungus, and the possible change in the number of cells of a population of cells of said strain of fungus to determine the degree of sensitivity of said strain of fungus to an antifungal agent, said change in the number of cells being determined compared to the number of cells of a population of cells of said strain of fungus in the absence of antifungal agent.

In the case of determining the degree of sensitivity of a strain of multicellular fungus, conidia of said strain constitute the living material on the basis of which the degree of sensitivity is determined.

Thus, in the case of a strain of multicellular fungus, the growth of said strain is assessed by quantifying the length of the vegetative germination hypha produced by the cells of said strain of fungus.

In the case of a strain of multicellular fungus, the growth of said strain is assessed by quantifying the length of the vegetative germination hypha produced by the conidia.

According to an especial embodiment, the present invention relates to the use of the possible change in the chitin level in a population of cells of a strain of fungus, said fungus being a multicellular fungus, and the possible change in the length of the vegetative germination hypha in said population of cells of said strain of fungus to determine the degree of sensitivity of said strain to an antifungal agent, said change in the length of the vegetative germination hypha being determined with respect to the length of the vegetative germination hypha of a population of cells of said strain of fungus in the absence of antifungal agent.

"Vegetative germination hypha" means the first vegetative hypha produced by a spore during germination thereof.

Fungi reproduce and disseminate in the form of cells called conidia. The term "conidia" means a spore ensuring the asexual multiplication of fungi and incapable of autonomous movement.

In the case of a strain of unicellular or multicellular fungus, the use solely of the possible change in the chitin level is sufficient for determining the resistant phenotype of the strain with respect to an antifungal agent in the case of a lack of increase in the chitin level or an increase in the chitin level less than 10% in a population of cells of a strain of fungus in the presence of said antifungal agent compared to the chitin level of a population of cells of said strain of fungus in the absence of antifungal agent.

According to an especial embodiment, the present invention relates to the use of the possible change in the chitin level in a population of cells of a strain of fungus, wherein the resistant phenotype of said strain of fungus with respect to an antifungal agent is determined by a lack of increase in the chitin level or an increase in the chitin level of less than 10% compared to the chitin level of a population of cells of said strain of fungus in the absence of antifungal agent.

The term "increase in the chitin level of less than 10%" means that an increase in the chitin level is observed in a population of cells of a strain of fungus in the presence of antifungal agent compared to a population of cells of said strain of fungus in the absence of antifungal agent and that said increase can assume any value greater than 0 and strictly less than 10%.

The term "lack of increase in the chitin level" means that the chitin level in a population of cells of a strain of fungus in the presence of an antifungal agent does not increase compared to a population of cells of said strain of fungus in the absence of antifungal agent, that is to say it can either be unchanged or can decrease.

According to an especial embodiment, the present invention relates to the use of the possible change in the chitin level in a population of cells of a strain of fungus, wherein the resistant phenotype of said strain of fungus with respect to an antifungal agent is determined by an increase in the chitin level of less than 10% or by a decrease in the chitin level or by an unchanged chitin level compared to the chitin level of a population of cells of said strain of fungus in the absence of antifungal agent.

According to an especial embodiment, the present invention relates to the use of the possible change in the chitin level in a population of cells of a strain of fungus, wherein the resistant phenotype of said strain of fungus with respect to an antifungal agent is determined by an increase in the chitin level of less than 10% or by a decrease in the chitin level of less than 20% or by an unchanged chitin level compared to the chitin level of a population of cells of said strain of fungus in the absence of antifungal agent.

In the case of a strain of unicellular or multicellular fungus, the use solely of the possible change in the chitin level is sufficient for determining the intermediate phenotype of the strain with respect to an antifungal agent in the case of an increase in the chitin level of from 10% to a value less than 20% in a population of cells of a strain of fungus in the presence of said antifungal agent compared to the chitin level of a population of cells of said strain of fungus in the absence of antifungal agent.

According to an especial embodiment, the present invention relates to the use of the possible change in the chitin level in a population of cells of a strain of fungus, wherein the intermediate phenotype of said strain of fungus with respect to an antifungal agent is determined by an increase in the chitin level of from 10% to a value less than 20% compared to the chitin level of a population of cells of said strain of fungus in the absence of antifungal agent.

The term "increase in the chitin level of from 10% to a value less than 20%" means that an increase of the chitin level is observed and that this increase may assume the value of 10% or any value greater than 10% and strictly less than 20%.

In the case of a strain of unicellular or multicellular fungus, the use solely of the possible change in the chitin level is sufficient for determining the degree of sensitivity of the strain not corresponding to a resistant phenotype, but to a sensitive or intermediate phenotype with respect to an antifungal agent in the case of an increase in the chitin level greater than or equal to 20% in a population of cells of a strain of fungus in the presence of said antifungal agent compared to the chitin level of a population of cells of said strain of fungus in the absence of antifungal agent.

According to an especial embodiment, the present invention relates to the use of the possible change in the chitin level in a population of cells of a strain of fungus, wherein the sensitive or intermediate phenotype of said strain of fungus with respect to an antifungal agent is determined by an increase in the chitin level greater than or equal to 20% compared to the chitin level of a population of cells of said strain of fungus in the absence of antifungal agent.

The term "increase in the chitin level greater than or equal to 20%" means that an increase of the chitin level is observed in a population of cells of a strain of fungus compared to a population of cells of said strain of fungus in the absence of antifungal agent and that this increase can assume the value of 20% or any other value greater than 20%.

However, the use solely of the possible change in the chitin level is not sufficient for determining whether the degree of sensitivity of said strain with respect to an antifungal agent corresponds to a sensitive or intermediate phenotype in the case of an increase in the chitin level greater than or equal to 20% in a population of cells of a strain of fungus in the presence of antifungal agent compared to the chitin level of a population of cells of said strain of fungus in the absence of antifungal agent.

In the case of a strain of unicellular fungus, the use of the possible change in the chitin level combined with the possible change in the number of cells in a population of cells of a strain of fungus in the presence of antifungal agent compared to a population of cells of said strain of fungus in the absence of antifungal agent allows the determination of the intermediate or sensitive phenotype with respect to said antifungal agent in the case of an increase in the chitin level greater than or equal to 20%.

More especially, in the case of a strain of unicellular fungus, the use of the possible change in the chitin level combined with the change in the number of cells in a population of cells of a strain of fungus in the presence of antifungal agent compared to a population of cells of said strain of fungus in the absence of antifungal agent allows the determination of the sensitive phenotype with respect to said antifungal agent in the case of an increase in the chitin level greater than or equal to 20% and a decrease in the number of cells of at least 0.3 log.

According to an especial embodiment, the present invention relates to the use of the possible change in the chitin level in a population of cells of a strain of fungus, said fungus being an unicellular fungus, wherein the sensitive phenotype of said strain of fungus with respect to an antifungal agent is determined by an increase in the chitin level greater than or equal to 20% compared to the chitin level of a population of cells of said strain of fungus in the absence of antifungal agent, and by determining the change in the number of cells in said population of cells of said strain of fungus in the presence of antifungal agent, said change being a decrease in the number of cells of at least 0.3 log compared to the number of cells of a population of cells of said strain of fungus in the absence of antifungal agent.

The term "decrease in the number of cells of at least 0.3 log" means that a decrease in the number of cells is observed in a population of cells of a strain of fungus in the presence of antifungal agent compared to a population of cells of said strain of fungus in the absence of said antifungal agent and that this decrease can assume the value of 0.3 log or any value greater than 0.3 log.

In the case of a strain of unicellular fungus, the use of the possible change in the chitin level combined with the possible change in the number of cells in a population of cells of a strain of fungus in the presence of antifungal agent compared to a population of cells of said strain of fungus in the absence of antifungal agent allows the determination of the intermediate phenotype with respect to said antifungal agent in the case of an increase in the chitin level greater than or equal to 20% and a decrease in the number of cells of less than 0.3 log or an unchanged number of cells. The possible change in the number of cells in a population of cells of a strain of fungus in the presence of antifungal agent compared to a population of cells of said strain of fungus in the absence of antifungal agent means that the number of cells may change, that is to say can increase or decrease. This change is possible, which means that there may be a change in the number of cells, that is to say an increase or decrease, or there may be no change, the number of cells then being unchanged.

The term "decrease in the number of cells of less than 0.3 log" means that a decrease in the number of cells is observed in a population of cells of a strain of fungus in the presence of antifungal agent compared to a population of cells of said strain of fungus in the absence of said antifungal agent and that this decrease can assume positive values strictly lower than 0.3 log.

According to an especial embodiment, the present invention relates to the use of the possible change in the chitin level in a population of cells of a strain of fungus, said fungus being an unicellular fungus, wherein the intermediate phenotype of said strain of fungus with respect to an antifungal agent is determined by an increase in the chitin level greater than or equal to 20% compared to the chitin level of a population of cells of said strain of fungus in the absence of antifungal agent, and by the possible change in the number of cells in said population of cells compared to the number of cells in a population of cells of said strain of fungus in the absence of antifungal agent, said possible change being a decrease in the number of cells of less than 0.3 log or an unchanged number of cells compared to the number of cells of a population of cells of said strain of fungus in the absence of antifungal agent.

In the case of a strain of multicellular fungus, the use solely of the possible change in the chitin level is sufficient for determining the resistant phenotype of the strain with respect to said antifungal agent in the case of an increase in the chitin level of less than 10% or a lack of increase in the chitin level in a population of cells of a strain of fungus in the presence of said antifungal agent compared to the chitin level of a population of cells of said strain of fungus in the absence of antifungal agent.

According to an especial embodiment, the present invention relates to the use of the possible change in the chitin level in a population of cells of a strain of fungus, said fungus being a multicellular fungus, wherein the resistant phenotype of said strain of fungus with respect to an antifungal agent is determined by an increase in the chitin level of less than 10% or a lack of increase in the chitin level compared to the chitin level of a population of cells of said strain of fungus in the absence of antifungal agent.

According to an especial embodiment, the present invention relates to the use of the possible change in the chitin level in a population of cells of a strain of fungus, said fungus being a multicellular fungus, wherein the resistant phenotype of said strain of fungus with respect to said antifungal agent is determined by an increase in the chitin level of less than 10% or by a decrease in the chitin level or by an unchanged chitin level compared to the chitin level of a population of cells of said strain of fungus in the absence of antifungal agent.

According to an especial embodiment, the present invention relates to the use of the possible change in the chitin level in a population of cells of a strain of fungus, said fungus being a multicellular fungus, wherein the resistant phenotype of said strain of fungus with respect to said antifungal agent is determined by an increase in the chitin level of less than 10% or by a decrease in the chitin level of less than 20% or by an unchanged chitin level compared to the chitin level of a population of cells of said strain of fungus in the absence of antifungal agent.

In the case of a strain of multicellular fungus, the use solely of the possible change in the chitin level is sufficient for determining whether the degree of sensitivity of the strain to an antifungal agent corresponds to an intermediate phenotype in the case of an increase in the chitin level of from 10% to a value less than 20% in a population of cells of a strain of fungus in the presence of said antifungal agent compared to the chitin level of a population of cells of said strain of fungus in the absence of antifungal agent.

According to an especial embodiment, the present invention relates to the use of the possible change in the chitin level in a population of cells of a strain of fungus, said strain of fungus being a multicellular fungus, wherein the intermediate phenotype of said strain of fungus with respect to an antifungal agent is determined by an increase in the chitin level of from 10% to a value less than 20% compared to the chitin level of a population of cells of said strain of fungus in the absence of antifungal agent.

In the case of a strain of multicellular fungus, the use of the possible change in the chitin level combined with the possible change in the length of the vegetative germination hypha produced by the cells of said strain of fungus in a population of cells of a strain of fungus in the presence of antifungal agent compared to a population of cells of said strain of fungus in the absence of antifungal agent allows the determination of the intermediate or sensitive phenotype of the strain with respect to said antifungal agent in the case of an increase in the chitin level greater than or equal to 20% and a decrease in the length of said hypha or an unchanged length of said hypha.

According to an especial embodiment, the present invention relates to the use of the possible change in the chitin level in a population of cells of a strain of fungus, said fungus being a multicellular fungus, wherein the sensitive or intermediate phenotype of said strain of fungus with respect to an antifungal agent is determined by an increase in the chitin level greater than or equal to 20% compared to the chitin level of a population of cells of said strain of fungus in the absence of antifungal agent, and by the possible change in the length of the vegetative germination hypha in said population of cells compared to the length of said hypha in a population of cells of said strain of fungus in the absence of antifungal agent, said possible change being a decrease in the length of said hypha or an unchanged length of said hypha compared to the length of the vegetative germination hypha of a population of cells of said strain of fungus in the absence of antifungal agent.

In multicellular and unicellular fungi, chitin is a constituent of the cell wall. Thus, the chitin level is determined in the wall of fungus cells by the following technique.

According to an especial embodiment, the present invention relates to the use of the possible change in the chitin level in a population of cells of a strain of fungus to determine the degree of sensitivity of said strain of fungus to an antifungal agent, wherein the possible change in the chitin level is determined in the wall of said fungus cells.

The minimum threshold of cells in said population of cells of said strain of fungus demonstrating an increase in the chitin level is at least 10%.

According to an especial embodiment, the present invention relates to the use of the possible change in the chitin level in a population of cells of a strain of fungus to determine the degree of sensitivity of said strain of fungus to an antifungal agent, said fungus being an unicellular fungus, wherein the minimum threshold of cells in said population of cells of said strain of fungus demonstrating an increased chitin level is at least 10%.

The term "increase in the chitin level of at least 10%" means that an increase of the chitin level is observed in a population of cells of a strain of fungus compared to a population of cells of said strain of fungus in the absence of antifungal agent and that this increase can assume the value of 10% or any other value greater than 10%.

According to an especial embodiment, the present invention relates to the use of the possible change in the chitin level in a population of cells of a strain of fungus to determine the degree of sensitivity of said strain of fungus to an antifungal agent, wherein the minimum threshold of cells in said population of cells of said strain of fungus demonstrating an increase in the chitin level is at least 10%, especially 20%, 25%, 30%, 35%, 40%, 45%, 50%, 55%, 60%, 65%, 70%, 75%, 80%, 85%, 90%, 95% and 100%.

According to an especial embodiment, the present invention relates to the use of the possible change in the number of cells in a population of cells of a strain of fungus to determine the degree of sensitivity of said strain of fungus to an antifungal agent, wherein the minimum level of decrease in the number of cells in said population of cells of said strain of fungus is at least 0.3 log, especially 0.4; 0.5; 0.6; 0.7; 0.8; 0.9; 1; 1.1; 1.2; 1.3; 1.4; 1.5; 1.6; 1.7; 1.8; 1.9; 2; 2.1; 2.2; 2.3; 2.4; 2.5; 2.6; 2.7; 2.8; 2.9; 3.

The degree of sensitivity of the strain of fungus to an antifungal agent is determined by means of the possible change in the chitin level of cells of said strain of fungus cultivated in the presence of a gradient of concentrations of antifungal agent in the liquid culture medium compared to said strain of fungus in the absence of antifungal agent in its culture medium.

According to an especial embodiment, the present invention relates to the use of the possible change in the chitin level in a population of cells of a strain of fungus to determine the degree of sensitivity of said strain of fungus to an antifungal agent, wherein said possible change in the chitin level is determined in the presence of a gradient of concentrations of an antifungal agent.

According to an especial embodiment, the present invention relates to the use of the possible change in the chitin level in a population of cells of a strain of fungus to determine the degree of sensitivity of said strain of fungus to an antifungal agent, wherein the gradient of concentrations of an antifungal agent is from 0.0009 to 130 µg/ml.

The chitin level in the cells of a strain of fungus can be measured by different methods, such as chemical dosage or fluorescence measurement.

According to an especial embodiment, the present invention relates to the use of the possible change in the chitin level in a population of cells of a strain of fungus to determine the degree of sensitivity of said strain of fungus to an antifungal agent, wherein the possible change in the chitin level is determined by fluorescence.

According to an especial embodiment, the present invention relates to the use of the possible change in the chitin level in a population of cells of a strain of fungus to determine the degree of sensitivity of said strain of fungus to an antifungal agent, wherein the possible change in the chitin level is determined by a method of fluorescence microscopy.

The chitin level in the cells of a strain of unicellular or multicellular fungus is measured by a method of fluorescence microscopy, such as a method of fluorescence microscopy measuring the total amount of fluorescence or by a high-content analysis (HCA) microscopy method, which measures the total amount of fluorescence per cell.

According to an especial embodiment, the present invention relates to the use of the possible change in the chitin level in a population of cells of a strain of fungus to determine the degree of sensitivity of said strain of fungus to an antifungal agent, wherein said method of fluorescence microscopy is high-content analysis (HCA) microscopy.

In the case of unicellular or multicellular fungi, the chitin is measured in the walls of the unicellular or multicellular fungus cells by a method of fluorescence microscopy with the aid of a fluorescent marker.

According to an especial embodiment, the present invention relates to the use of the possible change in the chitin level in a population of cells of a strain of fungus to determine the degree of sensitivity of said strain of fungus to an antifungal agent, wherein the possible change in the chitin level is determined with the aid of a fluorescent marker.

More especially, the fluorescent marker used to measure the chitin in the walls of unicellular or multicellular fungus cells by the HCA microscopy method is Calcofluor White.

According to an especial embodiment, the present invention relates to the use of the possible change in the chitin level in a population of cells of a strain of fungus to determine the degree of sensitivity of said strain of fungus to an antifungal agent, wherein said fluorescent marker is Calcofluor White.

The degree of sensitivity of a strain of unicellular or multicellular fungus to an antifungal agent is determined. Antifungal agents can have different modes of action.

According to an especial embodiment, the present invention relates to the use of the possible change in the chitin level in a population of cells of a strain of fungus to determine the degree of sensitivity of said strain of fungus to an antifungal agent, wherein the antifungal agent acts directly on the wall by action on the beta-glucans or mannoproteins or indirectly by means of action on the membrane or on any other constituent of the fungal cell.

According to an especial embodiment, the present invention relates to the use of the possible change in the chitin level in a population of cells of a strain of fungus to determine the degree of sensitivity of said strain of fungus to an antifungal agent, wherein the antifungal agent is selected from the group comprising or consisting of azole antifungal agents or other molecules that inhibit the synthesis of ergosterol, such as allylamines, for example terbinafine or morpholines, or echinocandins.

According to an especial embodiment, the present invention relates to the use of the possible change in the chitin level in a population of cells of a strain of fungus to determine the degree of sensitivity of said strain of fungus to an antifungal agent, the group of antifungal agents being free from polyenes such as amphotericin B and nystatin and antifungal agents that act directly on chitin.

According to an especial embodiment, the present invention relates to the use of the possible change in the chitin level in a population of cells of a strain of fungus to determine the degree of sensitivity of said strain of fungus to an antifungal agent, wherein the azole antifungal agent is selected from the group comprising or consisting to date of fluconazole, voriconazole, posaconazole, itraconazole and isavuconazole.

According to an especial embodiment, the present invention relates to the use of the possible change in the chitin level in a population of cells of a strain of fungus to determine the degree of sensitivity of said strain of fungus to an antifungal agent, wherein the echinocandin is selected from the group comprising or consisting to date of anidulafungin, caspofungin and micafungin.

According to an especial embodiment, the present invention relates to the use of the possible change in the chitin level in a population of cells of a strain of fungus to determine the degree of sensitivity of said strain of fungus to an antifungal agent, wherein the antifungal agent is selected from the group of antifungal agents free from polyenes such as amphotericin B and nystatin, and free from antifungal agents that act directly on chitin, more especially:
  from the group comprising or consisting azole antifungal agents, such as fluconazole, voriconazole, posaconazole, itraconazole and isavuconazole, or other molecules that inhibit the synthesis of ergosterol, such as allylamines, for example terbinafine or morpholines,
  or from echinocandins, the echinocandin being more especially selected from the group comprising or consisting of anidulafungin, caspofungin and micafungin.

According to an especial embodiment, the present invention relates to the use of the possible change in the chitin level in a population of cells of a strain of fungus to determine the degree of sensitivity of said strain of fungus to an antifungal agent, the group of antifungal agents additionally comprising polyenes such as amphotericin B and nystatin and being free from antifungal agents that act directly on chitin.

According to an especial embodiment, the present invention relates to the use of the possible change in the chitin level in a population of cells of a strain of fungus to determine the degree of sensitivity of said strain of fungus to an antifungal agent, wherein the antifungal agent to be tested is selected from the group formed of fluconazole, posaconazole, voriconazole, itraconazole, isavuconazole for the class of azoles; caspofungin, micafungin and anidulafungin for the class of echinocandins; and nystatin and amphotericin B for the class of polyenes, said group being free from antifungal agents that act directly on chitin.

In an especial embodiment the degree of sensitivity to an antifungal agent is determined for unicellular fungi.

The unicellular fungi are represented for the most part by yeasts.

According to an especial embodiment, the present invention relates to the use of the possible change in the chitin level in a population of cells of a strain of fungus to determine the degree of sensitivity of said strain of fungus to an antifungal agent, wherein the fungus is a yeast.

According to an especial embodiment, the present invention relates to the use of the possible change in the chitin level in a population of cells of a strain of fungus to determine the degree of sensitivity of said strain of fungus to an antifungal agent, wherein the population of yeast cells is selected from the group comprising or consisting of the genera *Candida, Cryptococcus, Saccharomyces, Trichosporon, Rhodotorula, Malassezia*.

According to an especial embodiment, the present invention relates to the use of the possible change in the chitin level in a population of cells of a strain of fungus to determine the degree of sensitivity of said strain of fungus to an antifungal agent, wherein the population of yeast cells is of the genus *Candida*.

According to an especial embodiment, the present invention relates to the use of the possible change in the chitin level in a population of cells of a strain of fungus to determine the degree of sensitivity of said strain of fungus to an antifungal agent, wherein the yeast of the genus *Candida* is selected from the group comprising or consisting of the species: *Candida albicans, C. glabatra, C. tropicalis, C. parapsilosis, C. krusei, C. dubliniensis, C. kefyr, C. lusitaniae, C. zeylanoides, C. rugosa, C. inconspicua, C. norvegensis, C. guilliermondii, C. utilis*.

According to an especial embodiment, the present invention relates to the use of the possible change in the chitin level in a population of cells of a strain of fungus to determine the degree of sensitivity of said strain of fungus to an antifungal agent, wherein the fungus is selected from the group comprising or consisting of the genera: *Aspergillus, Fusarium, Scedosporium, Lichteimia, Rhizopus, Rhizomucor, Mucor, Paecylomyces, Geotrichum*.

According to an especial embodiment, the present invention relates to the use of the possible change in the chitin level in a population of cells of a strain of fungus to determine the degree of sensitivity of said strain of fungus to an antifungal agent, wherein the fungus is of the genus *Aspergillus*.

According to an especial embodiment, the present invention relates to the use of the possible change in the chitin level in a population of cells of a strain of fungus to determine the degree of sensitivity of said strain of fungus to an antifungal agent, wherein the fungus of the genus *Aspergillus* is selected from the group comprising or consisting of the species: *A. fumigatus, A. flavus, A. nidulans, A. terreus, A. versicolor, A. niger*.

According to an especial embodiment, the present invention relates to the use of the possible change in the chitin level in a population of cells of a strain of fungus to determine the degree of sensitivity of said strain of fungus to an antifungal agent, wherein the fungus is of the genus *Fusarium*, and especially belongs to one of the species: *Fusarium solani, Fusarium oxysporum*.

According to an especial embodiment, the present invention relates to the use of the possible change in the chitin level in a population of cells of a strain of fungus to determine the degree of sensitivity of said strain of fungus to an antifungal agent, wherein the fungus is of the genus *Scedosporium*, and especially belongs to one of the species: *Scedosporium apiospermum, Scedosporium prolificans*.

According to an especial embodiment, the present invention relates to the use of the possible change in the chitin level in a population of cells of a strain of fungus to determine the degree of sensitivity of said strain of fungus to an antifungal agent, wherein the fungus is of the genus *Mucorales*, and especially belongs to one of the species: *Mucor, Lichteimia, Rhizopus, Rhizomucor*.

According to an especial embodiment, the present invention relates to the use of the possible change in the chitin level in a population of cells of a strain of fungus to determine the degree of sensitivity of said strain of fungus to an antifungal agent, wherein the fungus of the genus *Mucorales* is selected from the group comprising or consisting of the species: *Lichteimia corymbifera, Rhizopus oryzae, Rhizomucor pusillus, Mucor racemosa*.

According to an especial embodiment, the present invention relates to the use of the possible change in the chitin level in a population of cells of a strain of fungus to determine the degree of sensitivity of said strain of fungus to an antifungal agent, wherein the fungus is of the genus *Geotrichum*.

According to an especial embodiment, the present invention relates to the use of the possible change in the chitin level in a population of cells of a strain of fungus to determine the degree of sensitivity of said strain of fungus to an antifungal agent, wherein the fungus is of the genus *Paecylomyces*.

According to an especial embodiment, the present invention relates to the use of the possible change in the chitin level in a population of cells of a strain of fungus to determine the degree of sensitivity of said strain of fungus to an antifungal agent, wherein the fungus is selected from the group comprising or consisting of the genera: *Aspergillus, Fusarium, Scedosporium, Lichteimia, Rhizopus, Rhizomucor, Mucor, Geotrichum, Paecylomyces*, and species *Aspergillus fumigatus, Aspergillus flavus, Aspergillus niger, Aspergillus nidulans, Aspergillus terreus, Fusarium solani, Fusarium oxysporum, Scedosporium apiospermum, Scedosporium prohficans, Lichteimia corymbifera, Rhizopus oryzae, Rhizomucor pusillus, Mucor racemosa*.

The present invention also relates to a method for determining the degree of sensitivity of a population of cells of a strain of fungus to an antifungal agent.

In an especial embodiment the present invention relates to a method for determining the degree of sensitivity of a population of cells of a strain of fungus to an antifungal agent, comprising a step of determining the possible change in the chitin level in the population of cells of said strain of fungus in the presence of said antifungal agent compared to the chitin level of a population of cells of said strain of fungus in the absence of antifungal agent.

According to an especial embodiment the present invention relates to a method for determining the degree of sensitivity, corresponding to a sensitive, resistant or intermediate phenotype, of a population of cells of a strain of fungus to an antifungal agent, comprising a step of determining the possible change in the chitin level in the population of cells of said strain of fungus in the presence of said antifungal agent compared to the chitin level of a population of cells of said strain of fungus in the absence of antifungal agent.

In an especial embodiment the present invention relates to a method for determining the degree of sensitivity of a population of cells of a strain of fungus, said fungus being an unicellular fungus, to an antifungal agent, comprising a step of determining the possible change in the chitin level in the population of cells of said strain of fungus in the presence of said antifungal agent compared to the chitin level of a population of cells of said strain of fungus in the absence of antifungal agent.

In an especial embodiment the present invention relates to a method for determining the degree of sensitivity of a population of cells of a strain of fungus, said fungus being a multicellular fungus, to an antifungal agent, comprising a step of determining the possible change in the chitin level in the population of cells of said strain of fungus in the presence of said antifungal agent compared to the chitin level of a population of cells of said strain of fungus in the absence of antifungal agent.

According to an especial embodiment, the present invention relates to a method for determining the degree of sensitivity of a population of cells of a strain of fungus, said fungus being an unicellular fungus, to an antifungal agent, comprising a step of determining the possible change in the chitin level in the population of cells of said strain of fungus in the presence of said antifungal agent compared to the chitin level of a population of cells of said strain of fungus in the absence of antifungal agent, and a step of determining the possible change in the number of cells in said population of cells of said strain of fungus in the presence of said antifungal agent, said change in the number of cells being determined compared to the number of cells of a population of cells of said strain of fungus in the absence of antifungal agent.

According to an especial embodiment, the present invention relates to a method for determining the degree of sensitivity of a population of cells of a strain of fungus, said fungus being a multicellular fungus, to an antifungal agent, comprising a step of determining the possible change in the chitin level in the population of cells of said strain of fungus in the presence of said antifungal agent compared to the chitin level of a population of cells of said strain of fungus in the absence of antifungal agent, and a step of determining the possible change in the length of the vegetative germination hypha in said population of fungus cells in the presence of said antifungal agent, said possible change in the length of the vegetative germination hypha being determined compared to the length of the vegetative germination hypha in a population of cells of said strain of fungus in the absence of antifungal agent.

According to an especial embodiment the present invention relates to a method for determining the degree of sensitivity, corresponding to a resistant phenotype, of a population of cells of a strain of fungus to an antifungal agent, comprising a step of determining the possible change in the chitin level in the population of cells of said strain of fungus in the presence of said antifungal agent, said possible change being an increase in the chitin level of less than 10% or a lack of increase in the chitin level compared to the chitin level of a population of cells of said strain of fungus in the absence of antifungal agent.

According to an especial embodiment the present invention relates to a method for determining the degree of sensitivity, corresponding to a resistant phenotype, of a population of cells of a strain of fungus to an antifungal agent, comprising a step of determining the possible change in the chitin level in the population of cells of said strain of fungus in the presence of said antifungal agent, said possible change being an increase in the chitin level of less than 10% or a decrease in the chitin level or an unchanged chitin level compared to the chitin level of a population of cells of said strain of fungus in the absence of antifungal agent.

According to an especial embodiment the present invention relates to a method for determining the degree of sensitivity, corresponding to a resistant phenotype, of a population of cells of a strain of fungus to an antifungal agent, comprising a step of determining the possible change in the chitin level in the population of cells of said strain of fungus in the presence of said antifungal agent, said possible change being an increase in the chitin level of less than 10% or a decrease in the chitin level of less than 20% or an unchanged chitin level compared to the chitin level of a population of cells of said strain of fungus in the absence of antifungal agent.

According to an especial embodiment the present invention relates to a method for determining the degree of sensitivity, corresponding to an intermediate phenotype, of a population of cells of a strain of fungus to an antifungal agent, comprising a step of determining the change in the chitin level in the population of cells of said strain of fungus in the presence of said antifungal agent, said change being an increase in the chitin level of from 10% to a value less than 20% compared to the chitin level of a population of cells of said strain of fungus in the absence of antifungal agent.

According to an especial embodiment the present invention relates to a method for determining the degree of sensitivity, corresponding to a sensitive or intermediate phenotype, of a population of cells of a strain of fungus to an antifungal agent, comprising a step of determining the change in the chitin level in the population of cells of said strain of fungus in the presence of said antifungal agent, said change being an increase in the chitin level greater than or equal to 20% compared to the chitin level of a population of cells of said strain of fungus in the absence of antifungal agent.

According to an especial embodiment, the present invention relates to a method for determining the degree of sensitivity, corresponding to a sensitive phenotype, of a population of cells of a strain of fungus, said fungus being an unicellular fungus, to an antifungal agent, comprising a step of determining the change in the chitin level in the population of cells of said strain of fungus in the presence of said antifungal agent, said change being an increase in the chitin level greater than or equal to 20% compared to the chitin level of a population of cells of said strain of fungus in the absence of antifungal agent, and a step of determining the change in the number of cells in said population of cells of said strain of fungus in the presence of said antifungal agent, said change being a decrease in the number of cells of at least 0.3 log compared to the number of cells of a population of cells of said strain of fungus in the absence of antifungal agent.

According to an especial embodiment, the present invention relates to a method for determining the degree of sensitivity, corresponding to an intermediate phenotype, of a population of cells of a strain of fungus, said fungus being an unicellular fungus, to an antifungal agent, comprising a step of determining the change in the chitin level in the population of cells of said strain of fungus in the presence of said antifungal agent, said change being an increase in the chitin level greater than or equal to 20% compared to the chitin level of a population of cells of said strain of fungus in the absence of antifungal agent, and a step of determining the possible change in the number of cells in said strain of fungus in the presence of said antifungal agent, said possible change being a decrease in the number of cells of less than 0.3 log or an unchanged number of cells compared to the number of cells in a population of cells of said strain of fungus in the absence of antifungal agent.

According to an especial embodiment, the present invention relates to a method for determining the degree of sensitivity, corresponding to a sensitive or intermediate phenotype, of a population of cells of a strain of fungus, said fungus being a multicellular fungus, to an antifungal agent, comprising a step of determining the change in the chitin level in the population of cells of said strain of fungus in the presence of said antifungal agent, said change being an increase in the chitin level greater than or equal to 20% compared to the chitin level of a population of cells of said strain of fungus in the absence of antifungal agent, and a step of determining the possible change in the length of the vegetative germination hypha in said population of cells of said strain of fungus in the presence of said antifungal agent, said possible change in the length of the vegetative germination hypha being a decrease in the length of said hypha or an unchanged length of said hypha compared to the length of the vegetative germination hypha in a population of cells of said strain of fungus in the absence of antifungal agent.

According to an especial embodiment the present invention relates to a method for determining the degree of sensitivity, corresponding to a sensitive phenotype, of a population of cells of a strain of fungus to an antifungal agent, comprising a step of determining an increase in the chitin level in the population of cells of said strain of fungus in the presence of said antifungal agent compared to the chitin level of a population of cells of said strain of fungus in the absence of antifungal agent, said increase being at least 20%, especially 20%, 25%, 30%, 35%, 40%, 45%, 50%, 55%, 60%, 65%, 70%, 75%, 80%, 85%, 90%, 95% and 100%.

According to an especial embodiment the present invention relates to a method for determining the degree of sensitivity of a population of cells of a strain of fungus to an antifungal agent, comprising a step of determining the possible change in the chitin level performed in the presence of a gradient of concentrations of said antifungal agent.

According to an especial embodiment the present invention relates to a method for determining the degree of sensitivity of a population of cells of a strain of fungus to an antifungal agent, wherein the gradient of concentrations of antifungal agent is from 0.0009 to 130 µg/ml, from 0.0009 to 1 µg/ml, from 0.0009 to 5 µg/ml, from 0.0009 to 8 µg/ml or from 0.0009 to 16 µg/ml.

According to an especial embodiment the present invention relates to a method for determining the degree of sensitivity of a population of cells of a strain of fungus to an antifungal agent, wherein the possible change in the chitin level in the population of cells of said strain of fungus in the presence of said antifungal agent compared to the chitin level of a population of cells of said strain of fungus in the absence of antifungal agent is determined by a fluorescence method.

According to an especial embodiment the present invention relates to a method for determining the degree of sensitivity of a population of cells of a strain of fungus to an antifungal agent, wherein the fluorescence method is a method of fluorescence microscopy.

According to an especial embodiment the present invention relates to a method for determining the degree of sensitivity of a population of cells of a strain of fungus to an antifungal agent, wherein the method of fluorescence microscopy is high content analysis (HCA) microscopy.

According to an especial embodiment the present invention relates to a method for determining the degree of sensitivity of a population of cells of a strain of fungus to an antifungal agent, comprising a step of determining the fluorescent labelling of the cells of said strain of fungus making it possible to determine the possible change in the chitin level.

According to an especial embodiment the present invention relates to a method for determining the degree of sensitivity of a population of cells of a strain of fungus to an antifungal agent, comprising a step of fluorescent labelling of the cells of said strain of fungus performed with the aid of Calcofluor White.

According to an especial embodiment the present invention relates to a method for determining the degree of sensitivity of a population of cells of a strain of fungus to an antifungal agent, wherein the possible change in the chitin level in the population of cells of said strain of fungus in the presence of said antifungal agent is determined compared to the chitin level of a population of cells of said strain of fungus in the absence of antifungal agent, and wherein said antifungal agent acts on the wall directly on the beta-glucans or mannoproteins or indirectly by means of action on the membrane or on any other constituent of the fungal cell.

According to an especial embodiment, the present invention relates to a method for determining the degree of sensitivity of a population of cells of a strain of fungus to an antifungal agent, wherein the antifungal agent is selected from the group comprising or consisting of azole antifungal agents or other molecules that inhibit the synthesis of ergosterol, such as allylamines, for example terbinafine or morpholines, or echinocandins.

According to an especial embodiment, the present invention relates to a method for determining the degree of sensitivity of a population of cells of a strain of fungus to an antifungal agent, wherein the antifungal agent is selected from the group free from polyenes such as amphotericin B and nystatin and antifungal agents that act directly on chitin.

According to an especial embodiment the present invention relates to a method for determining the degree of sensitivity of a population of cells of a strain of fungus to an antifungal agent, wherein said antifungal agent is an azole antifungal agent selected from the group comprising voriconazole, posaconazole, itraconazole and isavuconazole.

According to an especial embodiment, the present invention relates to a method for determining the degree of sensitivity of a population of cells of a strain of fungus to an antifungal agent, wherein the antifungal agent is an echinocandin selected from the group comprising anidulafungin, caspofungin, and micafungin.

According to an especial embodiment, the present invention relates to a method for determining the degree of sensitivity of a population of cells of a strain of fungus to an antifungal agent, wherein the antifungal agent is selected from the group of antifungal agents free from polyenes such as amphotericin B and nystatin and free from antifungal agents that act directly on chitin, more especially:
  from the group comprising or consisting azole antifungal agents, such as fluconazole, voriconazole, posaconazole, itraconazole and isavuconazole, or other molecules that inhibit the synthesis of ergosterol, such as allylamines, for example terbinafine or morpholines;
  or from echinocandins, the echinocandin being more especially selected from the group comprising or consisting of anidulafungin, caspofungin and micafungin.

According to an especial embodiment the present invention relates to a method for determining the degree of sensitivity of a population of cells of a strain of fungus to an antifungal agent, wherein said fungus us a multicellular fungus.

According to an especial embodiment, the present invention relates to a method for determining the degree of sensitivity of a population of cells of a strain of fungus to an antifungal agent, wherein said fungus is selected from the group comprising *Aspergillus, Fusarium, Scedosporium, Lichteimia, Rhizopus, Mucor, Paecylomyces, Rhizomucor, Geotrichum*.

According to an especial embodiment the present invention relates to a method for determining the degree of sensitivity of a population of cells of a strain of fungus to an antifungal agent, wherein said fungus is of the genus *Aspergillus*.

According to an especial embodiment, the present invention relates to a method for determining the degree of sensitivity of a population of cells of a strain of fungus to an antifungal agent, wherein said fungus of the genus *Aspergillus* is selected from the group comprising *A. fumigatus, A. flavus, A. nidulans, A. terreus, A. versicolor, A. niger*.

According to an especial embodiment, the present invention relates to a method for determining the degree of sensitivity of a population of cells of a strain of fungus to an antifungal agent, wherein said fungus of the genus *Aspergillus*, selected from the group comprising the species *A. fumigatus, A. flavus, A. nidulans, A. terreus, A. versicolor, A. niger*, and wherein said antifungal agent is selected from the group of voriconazole, posaconazole, itraconazole, isavuconazole, micafungin, anidulafungin, caspofungin, amphotericin B, and nystatin.

According to an especial embodiment, the present invention relates to a method for determining the degree of sensitivity of a population of cells of a strain of fungus to an antifungal agent, wherein said antifungal agent is voriconazole, and wherein said fungus of the genus *Aspergillus* is selected from the group comprising the species *A. fumigatus, A. flavus, A. nidulans, A. terreus, A. versicolor, A. niger*.

According to an especial embodiment, the present invention relates to a method for determining the degree of sensitivity of a population of cells of a strain of fungus to an antifungal agent, wherein said antifungal agent is posaconazole, and wherein said fungus of the genus *Aspergillus* is selected from the group comprising the species *A. fumigatus, A. flavus, A. nidulans, A. terreus, A. versicolor, A. niger*.

According to an especial embodiment, the present invention relates to a method for determining the degree of sensitivity of a population of cells of a strain of fungus to an antifungal agent, wherein said antifungal agent is itraconazole, and wherein said fungus of the genus *Aspergillus* is selected from the group comprising the species *A. fumigatus, A. flavus, A. nidulans, A. terreus, A. versicolor, A. niger*.

According to an especial embodiment, the present invention relates to a method for determining the degree of sensitivity of a population of cells of a strain of fungus to an antifungal agent, wherein said antifungal agent is isavuconazole, and wherein said fungus of the genus *Aspergillus* is selected from the group comprising the species *A. fumigatus, A. flavus, A. nidulans, A. terreus, A. versicolor, A. niger*.

According to an especial embodiment, the present invention relates to a method for determining the degree of sensitivity of a population of cells of a strain of fungus to an antifungal agent, wherein said antifungal agent is micafungin, and wherein said fungus of the genus *Aspergillus* is selected from the group comprising the species *A. fumigatus, A. flavus, A. nidulans, A. terreus, A. versicolor, A. niger*.

According to an especial embodiment, the present invention relates to a method for determining the degree of sensitivity of a population of cells of a strain of fungus to an antifungal agent, wherein said antifungal agent is anidulafungin, and wherein said fungus of the genus *Aspergillus* is selected from the group comprising the species *A. fumigatus, A. flavus, A. nidulans, A. terreus, A. versicolor, A. niger*.

According to an especial embodiment, the present invention relates to a method for determining the degree of sensitivity of a population of cells of a strain of fungus to an antifungal agent, wherein said antifungal agent is caspofungin, and wherein said fungus of the genus *Aspergillus* is selected from the group comprising the species *A. fumigatus, A. flavus, A. nidulans, A. terreus, A. versicolor, A. niger*.

According to an especial embodiment, the present invention relates to a method for determining the degree of sensitivity of a population of cells of a strain of fungus to an antifungal agent, wherein said antifungal agent is amphotericin B, and wherein said fungus of the genus *Aspergillus* is selected from the group comprising the species *A. fumigatus, A. flavus, A. nidulans, A. terreus, A. versicolor, A. niger*.

According to an especial embodiment, the present invention relates to a method for determining the degree of sensitivity of a population of cells of a strain of fungus to an antifungal agent, wherein said antifungal agent is nystatin, and wherein said fungus of the genus *Aspergillus* is selected from the group comprising the species *A. fumigatus, A. flavus, A. nidulans, A. terreus, A. versicolor, A. niger*.

According to an especial embodiment, the present invention relates to a method for determining the degree of sensitivity of a population of cells of a strain of fungus to an antifungal agent, wherein said fungus is of the species *A. fumigatus*, and wherein said antifungal agent is selected from the group of voriconazole, posaconazole, itraconazole, isavuconazole, micafungin, anidulafungin, caspofungin, amphotericin B, and nystatin.

According to an especial embodiment, the present invention relates to a method for determining the degree of sensitivity of a population of cells of a strain of fungus to an antifungal agent, wherein said fungus is of the species *A. flavus*, and wherein said antifungal agent is selected from the group of voriconazole, posaconazole, itraconazole, isavuconazole, micafungin, anidulafungin, caspofungin, amphotericin B, and nystatin.

According to an especial embodiment, the present invention relates to a method for determining the degree of sensitivity of a population of cells of a strain of fungus to an antifungal agent, wherein said fungus is of the species *A. nidulans*, and wherein said antifungal agent is selected from the group of voriconazole, posaconazole, itraconazole, isavuconazole, micafungin, anidulafungin, caspofungin, amphotericin B, and nystatin.

According to an especial embodiment, the present invention relates to a method for determining the degree of sensitivity of a population of cells of a strain of fungus to an antifungal agent, wherein said fungus is of the species *A. terreus*, and wherein said antifungal agent is selected from the group of voriconazole, posaconazole, itraconazole, isavuconazole, micafungin, anidulafungin, caspofungin, amphotericin B, and nystatin.

According to an especial embodiment, the present invention relates to a method for determining the degree of sensitivity of a population of cells of a strain of fungus to an antifungal agent, wherein said fungus is of the species *A. versicolor*, and wherein said antifungal agent is selected from the group of voriconazole, posaconazole, itraconazole, isavuconazole, micafungin, anidulafungin, caspofungin, amphotericin B, and nystatin.

According to an especial embodiment, the present invention relates to a method for determining the degree of sensitivity of a population of cells of a strain of fungus to an antifungal agent, wherein said fungus is of the species *A. niger*, and wherein said antifungal agent is selected from the group of voriconazole, posaconazole, itraconazole, isavuconazole, micafungin, anidulafungin, caspofungin, amphotericin B, and nystatin.

According to an especial embodiment the present invention relates to a method for determining the degree of sensitivity of a population of cells of a strain of fungus to an antifungal agent, wherein said fungus is of the genus *Fusarium*.

According to an especial embodiment the present invention relates to a method for determining the degree of sensitivity of a population of cells of a strain of fungus to an antifungal agent, wherein said fungus is of the genus *Fusarium*, selected from the group comprising the species: *Fusarium solani, F. oxysporum*.

According to an especial embodiment, the present invention relates to a method for determining the degree of sensitivity of a population of cells of a strain of fungus to an antifungal agent, wherein said fungus is of the genus *Fusarium*, selected from the group comprising the species *Fusarium solani, F. oxysporum*, and wherein said antifungal agent is selected from the group of voriconazole, isavuconazole, amphotericin B, and nystatin.

According to an especial embodiment the present invention relates to a method for determining the degree of sensitivity of a population of cells of a strain of fungus to an antifungal agent, wherein said antifungal agent is voriconazole, and wherein said fungus is of the genus *Fusarium*, selected from the group comprising the species *Fusarium solani, F. oxysporum*.

According to an especial embodiment the present invention relates to a method for determining the degree of sensitivity of a population of cells of a strain of fungus to an antifungal agent, wherein said antifungal agent is isavuconazole, and wherein said fungus is of the genus *Fusarium*, selected from the group comprising the species *Fusarium solani, F. oxysporum*.

According to an especial embodiment the present invention relates to a method for determining the degree of sensitivity of a population of cells of a strain of fungus to an antifungal agent, wherein said antifungal agent is amphotericin B, and wherein said fungus is of the genus *Fusarium*, selected from the group comprising the species *Fusarium solani, F. oxysporum*.

According to an especial embodiment the present invention relates to a method for determining the degree of sensitivity of a population of cells of a strain of fungus to an antifungal agent, wherein said antifungal agent is nystatin, and wherein said fungus is of the genus *Fusarium*, selected from the group comprising the species *Fusarium solani, F. oxysporum*.

According to an especial embodiment, the present invention relates to a method for determining the degree of sensitivity of a population of cells of a strain of fungus to an antifungal agent, wherein said fungus is of the species *F. solani*, and wherein said antifungal agent is selected from the group of voriconazole, isavuconazole, micafungin, amphotericin B, and nystatin.

According to an especial embodiment, the present invention relates to a method for determining the degree of sensitivity of a population of cells of a strain of fungus to an antifungal agent, wherein said fungus is of the species *F. oxysporum*, and wherein said antifungal agent is selected from the group of voriconazole, isavuconazole, micafungin, amphotericin B, and nystatin.

According to an especial embodiment the present invention relates to a method for determining the degree of sensitivity of a population of cells of a strain of fungus to an antifungal agent, wherein said fungus is of the genus *Scedosporium*.

According to an especial embodiment the present invention relates to a method for determining the degree of sensitivity of a population of cells of a strain of fungus to an antifungal agent, wherein said fungus is of the genus *Scedosporium*, selected from the group comprising the species: *Scedosporium apiospermum, S. prolificans*.

According to an especial embodiment the present invention relates to a method for determining the degree of sensitivity of a population of cells of a strain of fungus to an antifungal agent, wherein said fungus is of the genus *Scedosporium*, selected from the group comprising the species: *Scedosporium apiospermum, S. prolificans*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said antifungal agent is voriconazole, and wherein said fungus is of the genus *Scedosporium*, selected from the group comprising the species. *Scedosporium apiospermum, S. prolificans*.

According to an especial embodiment the present invention relates to a method for determining the degree of sensitivity of a population of cells of a strain of fungus to an antifungal agent, wherein said antifungal agent is posaconazole, and wherein said fungus is of the genus *Scedosporium*, selected from the group comprising the species. *Scedosporium apiospermum, S. prolificans*.

According to an especial embodiment the present invention relates to a method for determining the degree of sensitivity of a population of cells of a strain of fungus to an antifungal agent, wherein said antifungal agent is isavuconazole, and wherein said fungus is of the genus *Scedosporium*, selected from the group comprising the species. *Scedosporium apiospermum, S. prolificans*.

According to an especial embodiment the present invention relates to a method for determining the degree of sensitivity of a population of cells of a strain of fungus to an antifungal agent, wherein said antifungal agent is amphotericin B, and wherein said fungus is of the genus *Scedosporium*, selected from the group comprising the species. *Scedosporium apiospermum, S. prolificans*.

According to an especial embodiment, the present invention relates to a method for determining the degree of sensitivity of a population of cells of a strain of fungus to an antifungal agent, wherein said fungus is of the species *S. apiospermum*, and wherein said antifungal agent is selected from the group of voriconazole, posaconazole, isavuconazole, and amphotericin B.

According to an especial embodiment, the present invention relates to a method for determining the degree of sensitivity of a population of cells of a strain of fungus to an antifungal agent, wherein said fungus is of the species *S. prolificans*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said fungus is of the genus *Mucor*.

According to an especial embodiment the present invention relates to a method for determining the degree of sensitivity of a population of cells of a strain of fungus to an antifungal agent, wherein said fungus is of the genus *Mucor*, selected from the group comprising the species *Mucor racemosa*.

According to an especial embodiment, the present invention relates to a method for determining the degree of sensitivity of a population of cells of a strain of fungus to an antifungal agent, wherein said fungus is of the genus *Mucor*, selected from the group comprising the species *Mucor racemosa*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said antifungal agent is voriconazole, and wherein said fungus is of the genus *Mucor*, selected from the group comprising the species *Mucor racemosa*.

According to an especial embodiment the present invention relates to a method for determining the degree of sensitivity of a population of cells of a strain of fungus to an antifungal agent, wherein said antifungal agent is posaconazole, and wherein said fungus is of the genus *Mucor*, selected from the group comprising the species *Mucor racemosa*.

According to an especial embodiment the present invention relates to a method for determining the degree of sensitivity of a population of cells of a strain of fungus to an antifungal agent, wherein said antifungal agent is isavuconazole, and wherein said fungus is of the genus *Mucor*, selected from the group comprising the species *Mucor racemosa*.

According to an especial embodiment the present invention relates to a method for determining the degree of sensitivity of a population of cells of a strain of fungus to an antifungal agent, wherein said antifungal agent is amphotericin B, and wherein said fungus is of the genus *Mucor*, selected from the group comprising the species *Mucor racemosa*.

According to an especial embodiment, the present invention relates to a method for determining the degree of sensitivity of a population of cells of a strain of fungus to an antifungal agent, wherein said fungus is of the species *M. racemosa*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said fungus is of the genus *Lichteimia*.

According to an especial embodiment the present invention relates to a method for determining the degree of sensitivity of a population of cells of a strain of fungus to an antifungal agent, wherein said fungus is of the genus *Lichteimia*, selected from the group comprising the species *Lichteimia* corymbifera.

According to an especial embodiment, the present invention relates to a method for determining the degree of sensitivity of a population of cells of a strain of fungus to an antifungal agent, wherein said fungus is of the genus *Lichteimia*, selected from the group comprising the species *Lichteimia corymbifera*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said antifungal agent is voriconazole, and wherein said fungus is of the genus *Lichteimia*, selected from the group comprising the species *Lichteimia corymbifera*.

According to an especial embodiment the present invention relates to a method for determining the degree of sensitivity of a population of cells of a strain of fungus to an antifungal agent, wherein said antifungal agent is posaconazole, and wherein said fungus is of the genus *Lichteimia*, selected from the group comprising the species *Lichteimia corymbifera*.

According to an especial embodiment the present invention relates to a method for determining the degree of sensitivity of a population of cells of a strain of fungus to an antifungal agent, wherein said antifungal agent is isavuconazole, and wherein said fungus is of the genus *Lichteimia*, selected from the group comprising the species *Lichteimia corymbifera*.

According to an especial embodiment the present invention relates to a method for determining the degree of sensitivity of a population of cells of a strain of fungus to an antifungal agent, wherein said antifungal agent is amphotericin B, and wherein said fungus is of the genus *Lichteimia*, selected from the group comprising the species *Lichteimia corymbifera*.

According to an especial embodiment, the present invention relates to a method for determining the degree of sensitivity of a population of cells of a strain of fungus to an antifungal agent, wherein said fungus is of the species *L. corymbifera*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said fungus is of the genus *Rhizopus*.

According to an especial embodiment the present invention relates to a method for determining the degree of sensitivity of a population of cells of a strain of fungus to an antifungal agent, wherein said fungus is of the genus *Rhizopus*, selected from the group comprising the species *Rhizopus oryzae*.

According to an especial embodiment, the present invention relates to a method for determining the degree of sensitivity of a population of cells of a strain of fungus to an antifungal agent, wherein said fungus is of the genus *Rhizopus*, selected from the group comprising the species *Rhizopus oryzae*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said antifungal agent is voriconazole, and wherein said fungus is of the genus *Rhizopus*, selected from the group comprising the species *Rhizopus oryzae*.

According to an especial embodiment the present invention relates to a method for determining the degree of sensitivity of a population of cells of a strain of fungus to an antifungal agent, wherein said antifungal agent is posaconazole, and wherein said fungus is of the genus *Rhizopus*, selected from the group comprising the species *Rhizopus oryzae*.

According to an especial embodiment the present invention relates to a method for determining the degree of sensitivity of a population of cells of a strain of fungus to an antifungal agent, wherein said antifungal agent is isavuconazole, and wherein said fungus is of the genus *Rhizopus*, selected from the group comprising the species *Rhizopus oryzae*.

According to an especial embodiment the present invention relates to a method for determining the degree of sensitivity of a population of cells of a strain of fungus to an antifungal agent, wherein said antifungal agent is amphotericin B, and wherein said fungus is of the genus *Rhizopus*, selected from the group comprising the species *Rhizopus oryzae*.

According to an especial embodiment, the present invention relates to a method for determining the degree of sensitivity of a population of cells of a strain of fungus to an antifungal agent, wherein said fungus is of the species *R. oryzae*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said fungus is of the genus *Rhizomucor*.

According to an especial embodiment the present invention relates to a method for determining the degree of sensitivity of a population of cells of a strain of fungus to an antifungal agent, wherein said fungus is of the genus *Rhizomucor*, selected from the group comprising the species *Rhizomucor pusillus*.

According to an especial embodiment, the present invention relates to a method for determining the degree of sensitivity of a population of cells of a strain of fungus to an antifungal agent, wherein said fungus is of the genus *Rhizomucor*, selected from the group comprising the species *Rhizomucor pusillus*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said antifungal agent is voriconazole, and wherein said fungus is of the genus *Rhizomucor*, selected from the group comprising the species *Rhizomucor pusillus*.

According to an especial embodiment the present invention relates to a method for determining the degree of sensitivity of a population of cells of a strain of fungus to an antifungal agent, wherein said antifungal agent is posaconazole, and wherein said fungus is of the genus *Rhizomucor*, selected from the group comprising the species *Rhizomucor pusillus*.

According to an especial embodiment the present invention relates to a method for determining the degree of sensitivity of a population of cells of a strain of fungus to an antifungal agent, wherein said antifungal agent is isavuconazole, and wherein said fungus is of the genus *Rhizomucor*, selected from the group comprising the species *Rhizomucor pusillus*.

According to an especial embodiment the present invention relates to a method for determining the degree of sensitivity of a population of cells of a strain of fungus to an antifungal agent, wherein said antifungal agent is amphotericin B, and wherein said fungus is of the genus *Rhizomucor*, selected from the group comprising the species *Rhizomucor pusillus*.

According to an especial embodiment, the present invention relates to a method for determining the degree of sensitivity of a population of cells of a strain of fungus to an antifungal agent, wherein said fungus is of the species *R. pusillis*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said fungus is of the genus *Geotrichum*.

According to an especial embodiment, the present invention relates to a method for determining the degree of sensitivity of a population of cells of a strain of fungus to an antifungal agent, wherein said fungus is of the genus *Geotrichum*, and wherein said antifungal agent is selected from the group of fluconazole, voriconazole, posaconazole, isavuconazole, and amphotericin B.

According to an especial embodiment the present invention relates to a method for determining the degree of sensitivity of a population of cells of a strain of fungus to an antifungal agent, wherein said antifungal agent is fluconazole, and wherein said fungus is of the genus *Geotrichum*.

According to an especial embodiment the present invention relates to a method for determining the degree of sensitivity of a population of cells of a strain of fungus to an antifungal agent, wherein said antifungal agent is voriconazole, and wherein said fungus is of the genus *Geotrichum*.

According to an especial embodiment the present invention relates to a method for determining the degree of sensitivity of a population of cells of a strain of fungus to an antifungal agent, wherein said antifungal agent is posaconazole, and wherein said fungus is of the genus *Geotrichum*.

According to an especial embodiment the present invention relates to a method for determining the degree of sensitivity of a population of cells of a strain of fungus to an antifungal agent, wherein said antifungal agent is isavuconazole, and wherein said fungus is of the genus *Geotrichum*.

According to an especial embodiment the present invention relates to a method for determining the degree of sensitivity of a population of cells of a strain of fungus to an antifungal agent, wherein said antifungal agent is amphotericin B, and wherein said fungus is of the genus *Geotrichum*.

According to an especial embodiment the present invention relates to a method for determining the degree of sensitivity of a population of cells of a strain of fungus to an antifungal agent, wherein said fungus is of the genus *Paecylomyces*.

According to an especial embodiment, the present invention relates to a method for determining the degree of sensitivity of a population of cells of a strain of fungus to an antifungal agent, wherein said fungus is of the genus *Paecylomyces*, and wherein said antifungal agent is selected from the group of voriconazole, posaconazole, isavuconazole, and amphotericin B.

According to an especial embodiment the present invention relates to a method for determining the degree of sensitivity of a population of cells of a strain of fungus to an antifungal agent, wherein said antifungal agent is voriconazole, and wherein said fungus is of the genus *Paecylomyces*.

According to an especial embodiment the present invention relates to a method for determining the degree of sensitivity of a population of cells of a strain of fungus to an antifungal agent, wherein said antifungal agent is posaconazole, and wherein said fungus is of the genus *Paecylomyces*.

According to an especial embodiment the present invention relates to a method for determining the degree of sensitivity of a population of cells of a strain of fungus to an antifungal agent, wherein said antifungal agent is isavuconazole, and wherein said fungus is of the genus *Paecylomyces*.

According to an especial embodiment the present invention relates to a method for determining the degree of sensitivity of a population of cells of a strain of fungus to an antifungal agent, wherein said antifungal agent is amphotericin B, and wherein said fungus is of the genus *Paecylomyces*.

According to an especial embodiment the present invention relates to a method for determining the degree of sensitivity of a population of cells of a strain of fungus to an antifungal agent, wherein said fungus is an unicellular fungus.

According to an especial embodiment the present invention relates to a method for determining the degree of sensitivity of a population of cells of a strain of fungus to an antifungal agent, wherein said fungus is a yeast.

According to an especial embodiment, the present invention relates to a method for determining the degree of sensitivity of a population of cells of a strain of fungus to an antifungal agent, wherein said fungus is a yeast selected from the group *Candida, Cryptococcus, Saccharomyces, Trichosporon, Rhodotorula, Malassezia*.

According to an especial embodiment the present invention relates to a method for determining the degree of sensitivity of a population of cells of a strain of fungus to an antifungal agent, wherein said fungus is a yeast of the genus *Candida*.

According to an especial embodiment the present invention relates to a method for determining the degree of sensitivity of a population of cells of a strain of fungus to an antifungal agent, wherein said fungus is a yeast of the genus *Candida*, selected from the group comprising the species: *Candida albicans, C. glabatra, C. tropicalis, C. parapsilosis, C. krusei, C. dubliniensis, C. kefyr, C. lusitaniae, C. zeylanoides, C. rugosa, C. inconspicua, C. norvegensis, C. guilliermondii, C. utilis*.

According to an especial embodiment, the present invention relates to a method for determining the degree of sensitivity of a population of cells of a strain of fungus to an antifungal agent, wherein said fungus is a yeast of the genus *Candida*, selected from the group comprising the species *Candida albicans, C. glabatra, C. tropicalis, C. parapsilosis, C. krusei*, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a strain of yeast of the genus *Candida*, selected from the group comprising the strains SC5314, DSY296, TOP of *Candida albicans*, ATCC®2001, Tg5 of *C. glabatra*, ATCC®7349, 13/5 of *C. tropicalis*, ATCC®22019, 8/21 of *C. parapsilosis*, ATCC®6258, GRE32 of *C. krusei*, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a yeast of the species *Candida albicans*, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a strain of yeast of the species *Candida albicans*, selected from the group SC5314, DSY296, TOP, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a yeast of the species *Candida glabrata*, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a strain of yeast of the species *Candida glabrata*, selected from the group ATCC®2001, Tg5, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a yeast of the species *Candida tropicalis*, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a strain of yeast of the species *Candida tropicalis*, selected from the group ATTCC®7349, 13/5, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a yeast of the species *Candida parapsilosis*, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a strain of yeast of the species *Candida parapsilosis*, selected from the group ATCC®22019, 8/21, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a yeast of the species *Candida krusei*, and wherein said antifungal agent is selected from the group of fluconazole, voriconazole, posaconazole, micafungin, and anidulafungin.

According to an especial embodiment, the present invention relates to a method for determining the degree of sensitivity of a population of cells of a strain of fungus to an antifungal agent, wherein said fungus is a strain of yeast of the species *Candida krusei*, selected from the group ATCC®6258, GRE32, and wherein said antifungal agent is selected from the group of fluconazole, voriconazole, posaconazole, micafungin, and anidulafungin.

According to an especial embodiment the present invention relates to a method for determining the degree of sensitivity of a population of cells of a strain of fungus to an antifungal agent, wherein said antifungal agent is fluconazole, and wherein said fungus is a yeast of the genus *Candida*, selected from the group comprising the species *Candida albicans, C. glabatra, C. tropicalis, C. parapsilosis, C. krusei*.

According to an especial embodiment, the present invention relates to a method for determining the degree of sensitivity of a population of cells of a strain of fungus to an antifungal agent, wherein said antifungal agent is fluconazole, and wherein said fungus is a strain of yeast of the genus *Candida*, selected from the group comprising the strains SC5314, DSY296, TOP of *Candida albicans*, ATCC®2001, Tg5 of *C. glabatra*, ATCC®7349, 13/5 of *C. tropicalis*, ATCC®22019, 8/21 of *C. parapsilosis*, ATCC®6258, GRE32 of *C. krusei*.

According to an especial embodiment the present invention relates to a method for determining the degree of sensitivity of a population of cells of a strain of fungus to an antifungal agent, wherein said antifungal agent is voriconazole, and wherein said fungus is a yeast of the genus *Candida*, selected from the group comprising the species *Candida albicans, C. glabatra, C. tropicalis, C. parapsilosis, C. krusei*.

According to an especial embodiment, the present invention relates to a method for determining the degree of sensitivity of a population of cells of a strain of fungus to an antifungal agent, wherein said antifungal agent is voriconazole, and wherein said fungus is a strain of yeast of the genus *Candida*, selected from the group comprising the strains SC5314, DSY296, TOP of *Candida albicans*, ATCC®2001, Tg5 of *C. glabatra*, ATCC®7349, 13/5 of *C. tropicalis*, ATCC®22019, 8/21 of *C. parapsilosis*, ATCC®6258, GRE32 of *C. krusei*.

According to an especial embodiment the present invention relates to a method for determining the degree of sensitivity of a population of cells of a strain of fungus to an antifungal agent, wherein said antifungal agent is posaconazole, and wherein said fungus is a yeast of the genus *Candida*, selected from the group comprising the species *Candida albicans, C. glabatra, C. tropicalis, C. parapsilosis, C. krusei*.

According to an especial embodiment, the present invention relates to a method for determining the degree of sensitivity of a population of cells of a strain of fungus to an antifungal agent, wherein said antifungal agent is posaconazole, and wherein said fungus is a strain of yeast of the genus *Candida*, selected from the group comprising the strains SC5314, DSY296, TOP of *Candida albicans*, ATCC®2001, Tg5 of *C. glabatra*, ATCC®7349, 13/5 of *C. tropicalis*, ATCC®22019, 8/21 of *C. parapsilosis*, ATCC®6258, GRE32 of *C. krusei*.

According to an especial embodiment the present invention relates to a method for determining the degree of sensitivity of a population of cells of a strain of fungus to an antifungal agent, wherein said antifungal agent is micafungin, and wherein said fungus is a yeast of the genus *Candida*, selected from the group comprising the species *Candida albicans, C. glabatra, C. tropicalis, C. parapsilosis, C. krusei*.

According to an especial embodiment, the present invention relates to a method for determining the degree of sensitivity of a population of cells of a strain of fungus to an antifungal agent, wherein said antifungal agent is micafungin, and wherein said fungus is a strain of yeast of the genus *Candida*, selected from the group comprising the strains SC5314, DSY296, TOP of *Candida albicans*, ATCC®2001, Tg5 of *C. glabatra*, ATCC®7349, 13/5 of *C. tropicalis*, ATCC®22019, 8/21 of *C. parapsilosis*, ATCC®6258, GRE32 of *C. krusei*.

According to an especial embodiment the present invention relates to a method for determining the degree of sensitivity of a population of cells of a strain of fungus to an antifungal agent, wherein said antifungal agent is anidulafungin, and wherein said fungus is a yeast of the genus *Candida*, selected from the group comprising the species *Candida albicans, C. glabatra, C. tropicalis, C. parapsilosis, C. krusei*.

According to an especial embodiment, the present invention relates to a method for determining the degree of sensitivity of a population of cells of a strain of fungus to an antifungal agent, wherein said antifungal agent is anidulafungin, and wherein said fungus is a strain of yeast of the genus *Candida*, selected from the group comprising the strains SC5314, DSY296, TOP of *Candida albicans*, ATCC®2001, Tg5 of *C. glabatra*, ATCC®7349, 13/5 of *C. tropicalis*, ATCC®22019, 8/21 of *C. parapsilosis*, ATCC®6258, GRE32 of *C. krusei*.

According to an especial embodiment the present invention relates to a method for determining the degree of sensitivity of a population of cells of a strain of fungus to an antifungal agent, comprising a step of contacting said antifungal agent and cells of said strain of fungus prior to the step of determining the possible change in the chitin level.

According to an especial embodiment the present invention relates to a method for determining the degree of sensitivity of a population of cells of a strain of fungus to an antifungal agent, wherein said contacting step lasts for a period of time less than or equal to 48 h.

According to an especial embodiment the present invention relates to a method for determining the degree of sensitivity of a population of cells of a strain of fungus to an antifungal agent, wherein said contacting step lasts for a period of time less than or equal to 24 h.

According to an especial embodiment the present invention relates to a method for determining the degree of sensitivity of a population of cells of a strain of fungus to an antifungal agent, wherein said contacting step lasts for at least 6.5 h.

According to an especial embodiment the present invention relates to a method for determining the degree of sensitivity of a population of cells of a strain of fungus to an antifungal agent, wherein said contacting step lasts for 6.5 h to 24 h.

According to an especial embodiment the present invention relates to a method for determining the degree of sensitivity of a population of cells of a strain of fungus to an antifungal agent, wherein said contacting step lasts for 6.5 h to 24 h, especially 6.5 h to 8 h, 6.5 h to 10 h, 6.5 h to 12 h, 6.5 h to 14 h, 6. h to 16 h, 6.5 h to 18 h, 6.5 h to 20 h, 6.5 h to 22 h.

According to an especial embodiment the present invention relates to a method for determining the degree of sensitivity of a population of cells of a strain of fungus to an antifungal agent, wherein said contacting step lasts for 6.5 h.

According to an especial embodiment the present invention relates to a method for determining the degree of sensitivity of a population of cells of a strain of fungus to an antifungal agent, wherein said contacting step lasts for 24 h.

According to an especial embodiment the present invention relates to a method for determining the degree of sensitivity of a population of cells of a strain of fungus to an antifungal agent, wherein said contacting step is performed at a temperature of from 30 to 35° C.

According to an especial embodiment the present invention relates to a method for determining the degree of sensitivity of a population of cells of a strain of fungus to an antifungal agent, wherein said contacting step is performed at a temperature of from 30 to 35° C., especially from 30° C. to 31° C., from 30° C. to 32° C., from 30° C. to 33° C., from 30° C. to 34° C.

According to an especial embodiment the present invention relates to a method for determining the degree of sensitivity of a population of cells of a strain of fungus to an antifungal agent, wherein said contacting step is performed at a temperature of 30° C.

According to an especial embodiment the present invention relates to a method for determining the degree of sensitivity of a population of cells of a strain of fungus to an antifungal agent, wherein said contacting step is performed at a temperature of 35° C.

According to an especial embodiment the present invention relates to a method for determining the degree of sensitivity of a population of cells of a strain of fungus to an antifungal agent, comprising a step of fluorescent labelling of the cells of said strain of fungus by a fluorescent marker.

According to an especial embodiment the present invention relates to a method for determining the degree of sensitivity of a population of cells of a strain of fungus to an antifungal agent, comprising a step of fluorescent labelling of the cells of said strain of fungus by a fluorescent marker, said step being performed during or after the step of contacting said antifungal agent with cells of said strain of fungus.

According to an especial embodiment the present invention relates to a method for determining the degree of sensitivity of a population of cells of a strain of fungus to an antifungal agent, comprising a step of fluorescent labelling of the cells of said strain of fungus by a fluorescent marker, said step being performed before the step of contacting said antifungal agent with cells of said strain of fungus.

According to an especial embodiment the present invention relates to a method for determining the degree of sensitivity of a population of cells of a strain of fungus to an antifungal agent, comprising a step of fluorescent labelling of the cells of said strain of fungus by a fluorescent marker, said step being performed simultaneously with the step of contacting said antifungal agent with cells of said strain of fungus.

According to an especial embodiment the present invention relates to a method for determining the degree of sensitivity of a population of cells of a strain of fungus to an antifungal agent, comprising a step of fluorescent labelling of the cells of said strain of fungus by a fluorescent marker, said step being performed after the step of contacting said antifungal agent with cells of said strain of fungus.

According to an especial embodiment the present invention relates to a method for determining the degree of sensitivity of a population of cells of a strain of fungus to an antifungal agent, comprising a step of contacting said antifungal agent and cells of said strain of fungus and a step of labelling of cells of said strain of fungus by a fluorescent marker, said marker being Calcofluor White.

According to an especial embodiment the present invention relates to a method for determining the degree of sensitivity of a population of cells of a strain of fungus to an antifungal agent, comprising a step of determining the possible change in the chitin level by quantification of the chitin level in the cells of said strain of fungus by fluorescence microscopy.

According to an especial embodiment, the present invention relates to a method for determining the degree of sensitivity, corresponding to a sensitive phenotype, of a population of cells of a strain of fungus, said fungus being an unicellular fungus, to an antifungal agent, comprising a step of determining the change in the chitin level, said change being an increase in the chitin level greater than or equal to 20% in the population of cells of said strain of fungus in the presence of said antifungal agent compared to the chitin level of a population of cells of said strain of fungus in the absence of antifungal agent, by quantification of the chitin level by fluorescence microscopy, followed by a step of determining the possible change in the number of cells in said population of cells of said strain of fungus in the presence of said antifungal agent compared to the number of cells of a population of cells of said strain of fungus in the absence of antifungal agent.

According to an especial embodiment, the present invention relates to a method for determining the degree of sensitivity, corresponding to an intermediate phenotype, of a population of cells of a strain of fungus, said fungus being an unicellular fungus, to an antifungal agent, comprising a step of determining the change in the chitin level, said change being an increase in the chitin level greater than or equal to 20% in the population of cells of said strain of fungus in the presence of said antifungal agent compared to the chitin level of a population of cells of said strain of fungus in the absence of antifungal agent, by quantification of the chitin level by fluorescence microscopy, followed by a step of determining the possible change in the number of cells in said population of cells of said strain of fungus in the presence of said antifungal agent compared to the number of cells of a population of cells of said strain of fungus in the absence of antifungal agent.

According to an especial embodiment, the present invention relates to a method for determining the degree of sensitivity, corresponding to a sensitive phenotype, of a population of cells of a strain of fungus, said fungus being a multicellular fungus, to an antifungal agent, comprising a step of determining the change in the chitin level, said change being an increase in the chitin level greater than or equal to 20% in the population of cells of said strain of fungus in the presence of said antifungal agent compared to the chitin level of a population of cells of said strain of fungus in the absence of antifungal agent, by quantification of the chitin level by fluorescence microscopy, followed by a step of determining the possible change in the length of the vegetative germination hypha in said population of cells of said strain of fungus in the presence of said antifungal agent compared to the length of the vegetative germination hypha in a population of cells of said strain of fungus in the absence of antifungal agent.

According to an especial embodiment, the present invention relates to a method for determining the degree of sensitivity, corresponding to an intermediate phenotype, of a population of cells of a strain of fungus, said fungus being a multicellular fungus, to an antifungal agent, comprising a step of determining the change in the chitin level, said change being an increase in the chitin level greater than or equal to 20% in the population of cells of said strain of fungus in the presence of said antifungal agent compared to the chitin level of a population of cells of said strain of fungus in the absence of antifungal agent, by quantification of the chitin level by fluorescence microscopy, followed by a step of determining the possible change in the length of the vegetative germination hypha in said population of cells of said strain of fungus in the presence of said antifungal agent compared to the length of the vegetative germination hypha in a population of cells of said strain of fungus in the absence of antifungal agent.

According to an especial embodiment the present invention relates to a method for determining the degree of sensitivity of a population of cells of a strain of fungus, said fungus being an unicellular or multicellular fungus, to an antifungal agent, comprising:
- a. a step of contacting cells of said strain of fungus with a concentration of antifungal agent varying from 0.0009 to 130 μg/ml, so as to obtain a mixture of cells of said strain of fungus with the antifungal agent;
- b. a step of adding a fluorescent marker to the mixture of cells of said strain of fungus and antifungal agent obtained previously, so as to obtain a mixture of cells of said strain of fungus, labelled by the fluorescent marker, and antifungal agent;
- c. a step of quantifying the chitin level by fluorescence microscopy of the labelled cells of said strain of fungus in the mixture obtained in the previous step;
- d. a step of determining the possible change in the chitin level in the mixture of cells of said strain of fungus labelled by the fluorescent marker and antifungal agent compared to the chitin level of a population of cells of said strain of fungus in the absence of antifungal agent;

when said possible change in the chitin level of said step d. is an increase of less than 10% or when there is no increase, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment the present invention relates to a method for determining the degree of sensitivity of a population of cells of a strain of fungus, said fungus being an unicellular or multicellular fungus, to an antifungal agent, comprising:
- a. a step of contacting cells of said strain of fungus with a concentration of antifungal agent varying from 0.0009 to 130 μg/ml, so as to obtain a mixture of cells of said strain of fungus with the antifungal agent;
- b. a step of adding a fluorescent marker to the mixture of cells of said strain of fungus and antifungal agent obtained previously, so as to obtain a mixture of cells of said strain of fungus labelled by the fluorescent marker and antifungal agent;
- c. a step of quantifying the chitin level by fluorescence microscopy of the labelled cells of said strain of fungus in the mixture obtained in the previous step;
- d. a step of determining the possible change in the chitin level in the mixture of cells of said strain of fungus labelled by the fluorescent marker and antifungal agent compared to the chitin level of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment the present invention relates to a method for determining the degree of sensitivity of a population of cells of a strain of fungus, said fungus being an unicellular fungus, to an antifungal agent, comprising:
- a. a step of contacting cells of said strain of fungus with a concentration of antifungal agent varying from 0.0009 to 130 μg/ml, so as to obtain a mixture of cells of said strain of fungus with the antifungal agent;
- b. a step of adding a fluorescent marker to the mixture of cells of said strain of fungus and antifungal agent obtained previously, so as to obtain a mixture of cells of said strain of fungus labelled by the fluorescent marker and antifungal agent;
- c. a step of quantifying the chitin level by fluorescence microscopy of the labelled cells of said strain of fungus in the mixture obtained in the previous step;
- d. a step of determining the possible change in the chitin level in the mixture of cells of said strain of fungus labelled by the fluorescent marker and antifungal agent compared to the chitin level of a population of cells of said strain of fungus in the absence of antifungal agent;

and in the case in which said possible change in the chitin level is an increase in the chitin level greater than or equal to 20%, said step d is followed by
- e. a step of counting the cells in the mixture of cells of said strain of fungus labelled by the fluorescent marker and antifungal agent; then by
- f. a step of determining the possible change in the number of cells in the population of cells of said strain of fungus in the presence of antifungal agent compared to the number of cells in a population of cells of said strain of fungus in the absence of antifungal agent;

when said possible change in the chitin level of said step d. is an increase of less than 10% or when there is no increase, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. increases by a value greater than or equal to 20%, and when said possible change in the number of cells of said step f. is a decrease in the number of cells of less than 0.3 log or the number of cells is unchanged, it is concluded that said strain of fungus has an intermediate phenotype;

when said change in the chitin level of said step d. is an increase by a value greater than or equal to 20%, and when said change in the number of cells of said step f is a decrease of at least 0.3 log, it is concluded that said strain of fungus has a sensitive phenotype;

According to an especial embodiment the present invention relates to a method for determining the degree of sensitivity of a population of cells of a strain of fungus, said fungus being an unicellular fungus, to an antifungal agent, comprising:
- a. a step of contacting cells of said strain of fungus with a concentration of antifungal agent varying from 0.0009 to 130 µg/ml, so as to obtain a mixture of cells of said strain of fungus with the antifungal agent;
- b. a step of adding a fluorescent marker to the mixture of cells of said strain of fungus and antifungal agent obtained previously, so as to obtain a mixture of cells of said strain of fungus labelled by the fluorescent marker and antifungal agent;
- c. a step of quantifying the chitin level by fluorescence microscopy of the labelled cells of said strain of fungus in the mixture obtained in the previous step;
- d. a step of determining the possible change in the chitin level in the mixture of cells of said strain of fungus labelled by the fluorescent marker and antifungal agent compared to the chitin level of a population of cells of said strain of fungus in the absence of antifungal agent;

and in the case in which said possible change in the chitin level is an increase in the chitin level greater than or equal to 20%, said step d is followed by
- e. a step of counting the cells in the mixture of cells of said strain of fungus labelled by the fluorescent marker and antifungal agent; then by
- f. a step of determining the possible change in the number of cells in the population of cells of said strain of fungus in the presence of antifungal agent compared to the number of cells in a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. increases by a value greater than or equal to 20%, and when said possible change in the number of cells of said step f. is a decrease in the number of cells of less than 0.3 log or the number of cells is unchanged, it is concluded that said strain of fungus has an intermediate phenotype;

when said change in the chitin level of said step d. is an increase by a value greater than or equal to 20%, and when said change in the number of cells of said step f is a decrease of at least 0.3 log, it is concluded that said strain of fungus has a sensitive phenotype;

According to an especial embodiment the present invention relates to a method for determining the degree of sensitivity of a population of cells of a strain of fungus, said fungus being a multicellular fungus, to an antifungal agent, comprising:
- a. a step of contacting cells of said strain of fungus with a concentration of antifungal agent varying from 0.0009 to 130 µg/ml, so as to obtain a mixture of cells of said strain of fungus with the antifungal agent;
- b. a step of adding a fluorescent marker to the mixture of cells of said strain of fungus and antifungal agent obtained previously, so as to obtain a mixture of cells of said strain of fungus labelled by the fluorescent marker and antifungal agent;
- c. a step of quantifying the chitin level by fluorescence microscopy of the labelled cells of said strain of fungus in the mixture obtained in the previous step;
- d. a step of determining the possible change in the chitin level in the mixture of cells of said strain of fungus labelled by the fluorescent marker and antifungal agent compared to the chitin level of a population of cells of said strain of fungus in the absence of antifungal agent;

and in the case in which said possible change in the chitin level is an increase in the chitin level greater than or equal to 20%, said step d is followed by
- e. a step of measuring the length of the vegetative germination hypha in the mixture of cells of said strain of fungus labelled by the fluorescent marker and antifungal agent; then by
- f. a step of determining the possible change in the length of the vegetative germination hypha in the population of cells of said strain of fungus in the presence of antifungal agent compared to the length of the vegetative germination hypha in a population of cells of said strain of fungus in the absence of antifungal agent;

when said possible change in the chitin level of said step d. reveals no increase or an increase of less than 10%, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease in the length of said hypha or an unchanged length of said hypha, it is concluded that said strain of fungus has a sensitive or intermediate phenotype;

According to an especial embodiment the present invention relates to a method for determining the degree of sensitivity of a population of cells of a strain of fungus, said fungus being a multicellular fungus, to an antifungal agent, comprising:
- a. a step of contacting cells of said strain of fungus with a concentration of antifungal agent varying from 0.0009 to 130 µg/ml, so as to obtain a mixture of cells of said strain of fungus with the antifungal agent;
- b. a step of adding a fluorescent marker to the mixture of cells of said strain of fungus and antifungal agent obtained previously, so as to obtain a mixture of cells of said strain of fungus labelled by the fluorescent marker and antifungal agent;
- c. a step of quantifying the chitin level by fluorescence microscopy of the labelled cells of said strain of fungus in the mixture obtained in the previous step;
- d. a step of determining the possible change in the chitin level in the mixture of cells of said strain of fungus labelled by the fluorescent marker and antifungal agent compared to the chitin level of a population of cells of said strain of fungus in the absence of antifungal agent;

and in the case in which said possible change in the chitin level is an increase in the chitin level greater than or equal to 20%, said step d is followed by e. a step of measuring the length of the vegetative germination hypha in the mixture of cells of said strain of fungus labelled by the fluorescent marker and antifungal agent; then by f. a step of determining the possible change in the length of the vegetative germination hypha in the population of cells of said strain of fungus in the presence of antifungal agent compared to the length of the vegetative germination hypha in a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease in the length of said hypha or an unchanged length of said hypha, it is concluded that said strain of fungus has a sensitive or intermediate phenotype;

According to an especial embodiment the present invention relates to a method for determining the degree of sensitivity of a population of cells of a strain of fungus to an antifungal agent, wherein said step of contacting cells of said strain of fungus with a range of concentration of said antifungal agent from 0.0009 to 130 µg/ml, is performed at a temperature of from 30 to 35° C. for a period of time less than or equal to 48 h, especially for a period of time of from 6.5 h to 24 h, so as to obtain a mixture of cells of said strain of fungus and said antifungal agent.

According to an especial embodiment the present invention relates to a method for determining the degree of sensitivity of a population of cells of a strain of fungus to an antifungal agent, wherein the step of adding the fluorescent marker to the mixture of cells of said strain of fungus and said antifungal agent, obtained after the contacting step, is performed with the aid of Calcofluor White, so as to obtain a mixture of cells of said strain of fungus, labelled by Calcofluor White, and said antifungal agent.

According to an especial embodiment the present invention relates to a method for determining the degree of sensitivity of a population of cells of a strain of fungus, said fungus being an unicellular or multicellular fungus, to an antifungal agent, comprising:

a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

when said possible change in the chitin level of said step d. is an increase of less than 10% or when there is no increase, it is concluded that said strain has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment the present invention relates to a method for determining the degree of sensitivity of a population of cells of a strain of fungus, said fungus being an unicellular or multicellular fungus, to an antifungal agent, comprising:

a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment the present invention relates to a method for determining the degree of sensitivity of a population of cells of a strain of fungus, said fungus being an unicellular fungus, to an antifungal agent, comprising:

a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
c. a step of quantifying the chitin level, by high-content analysis fluorescence microscopy, of the labelled cells of said strain of fungus in the mixture obtained in the previous step;
d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by
  e. a step of counting the cells in the mixture of cells of said strain of fungus, labelled by Calcofluor White, and antifungal agent; then by
  f. a step of determining the possible change in the number of cells as a function of the concentration of antifungal agent in the population of cells of said strain of fungus compared to the number of cells in a population of cells of said strain of fungus in the absence of antifungal agent;

when said possible change in the chitin level of said step d. is an increase of less than 10% or when there is no increase in the chitin level, it is concluded that said strain of fungus has a resistant phenotype;
when said change in the chitin level of said step d. is an increase of from 10% to a value less than 20%, it is concluded that said strain of fungus has an intermediate phenotype;
when said change in the chitin level of said step d. in creases by a value greater than or equal to 20%, and when said possible change in the number of cells of said step f is a decrease in the number of cells of less than 0.3 log or the number of cells is unchanged, it is concluded that said strain of fungus has an intermediate phenotype;
when said change in the chitin level of said step d. is an increase by a value greater than or equal to 20%, and when said change in the number of cells of said step f is a decrease of at least 0.3 log, it is concluded that said strain of fungus has a sensitive phenotype;

According to an especial embodiment the present invention relates to a method for determining the degree of sensitivity of a population of cells of a strain of fungus, said fungus being an unicellular fungus, to an antifungal agent, comprising:
  a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
  b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
  c. a step of quantifying the chitin level, by high-content analysis fluorescence microscopy, of the labelled cells of said strain of fungus in the mixture obtained in the previous step;
  d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by
  e. a step of counting the cells in the mixture of cells of said strain of fungus, labelled by Calcofluor White, and antifungal agent; then by
  f. a step of determining the possible change in the number of cells as a function of the concentration of antifungal agent in the population of cells of said strain of fungus compared to the number of cells in a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;
when said change in the chitin level of said step d. is an increase of from 10% to a value less than 20%, it is concluded that said strain of fungus has an intermediate phenotype;
when said change in the chitin level of said step d. in creases by a value greater than or equal to 20%, and when said possible change in the number of cells of said step f is a decrease in the number of cells of less than 0.3 log or the number of cells is unchanged, it is concluded that said strain of fungus has an intermediate phenotype;
when said change in the chitin level of said step d. is an increase by a value greater than or equal to 20%, and when said change in the number of cells of said step f is a decrease of at least 0.3 log, it is concluded that said strain of fungus has a sensitive phenotype;

According to an especial embodiment the present invention relates to a method for determining the sensitivity or resistance of a population of cells of a strain of fungus, said fungus being a multicellular fungus, to an antifungal agent, comprising:
  a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
  b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
  c. a step of quantifying the chitin level, by high-content analysis fluorescence microscopy, of the labelled cells of said strain of fungus in the mixture obtained in the previous step;
  d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by

- e. a step of measuring the length of the vegetative germination hypha in the mixture of cells of said strain of fungus, labelled by Calcofluor White, and antifungal agent; then by
- f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or when there is no increase, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease in the length of said hypha or an unchanged length of said hypha, it is concluded that said strain of fungus has a sensitive or intermediate phenotype;

According to an especial embodiment the present invention relates to a method for determining the sensitivity or resistance of a population of cells of a strain of fungus, said fungus being a multicellular fungus, to an antifungal agent, comprising:

- a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
- b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
- c. a step of quantifying the chitin level, by high-content analysis fluorescence microscopy, of the labelled cells of said strain of fungus in the mixture obtained in the previous step;
- d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by

- e. a step of measuring the length of the vegetative germination hypha in the mixture of cells of said strain of fungus, labelled by Calcofluor White, and antifungal agent; then by
- f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease in the length of said hypha or an unchanged length of said hypha, it is concluded that said strain of fungus has a sensitive or intermediate phenotype;

According to an especial embodiment the present invention relates to a method for determining the degree of sensitivity, corresponding to a resistant phenotype, of a population of cells of a strain of fungus, said fungus being an unicellular or multicellular fungus, to an antifungal agent, comprising:

- a. a step of contacting cells of said strain of fungus with a concentration of antifungal agent varying from 0.0009 to 130 µg/ml, so as to obtain a mixture of cells of said strain of fungus with the antifungal agent;
- b. a step of adding a fluorescent marker to the mixture of cells of said strain of fungus and antifungal agent obtained previously, so as to obtain a mixture of cells of said strain of fungus, labelled by the fluorescent marker, and antifungal agent;
- c. a step of quantifying the chitin level by fluorescence microscopy of the labelled cells of said strain of fungus in the mixture obtained in the previous step;
- d. a step of determining a lack of any increase in the chitin level or an increase in the chitin level of less than 10% in the mixture of cells of said strain of fungus, labelled by the fluorescent marker, and antifungal agent compared to the chitin level of a population of cells of said strain of fungus in the absence of antifungal agent;

According to an especial embodiment the present invention relates to a method for determining the degree of sensitivity, corresponding to a resistant phenotype, of a population of cells of a strain of fungus, said fungus being an unicellular or multicellular fungus, to an antifungal agent, comprising:

- a. a step of contacting cells of said strain of fungus with a concentration of antifungal agent varying from 0.0009 to 130 µg/ml, so as to obtain a mixture of cells of said strain of fungus with the antifungal agent;
- b. a step of adding a fluorescent marker to the mixture of cells of said strain of fungus and antifungal agent obtained previously, so as to obtain a mixture of cells of said strain of fungus, labelled by the fluorescent marker, and antifungal agent;
- c. a step of quantifying the chitin level by fluorescence microscopy of the labelled cells of said strain of fungus in the mixture obtained in the previous step;
- d. a step of determining a lack of any increase in the chitin level, or an increase in the chitin level of less than 10%, or a decrease in the chitin level especially of less than 20%, or an unchanged level in the mixture of cells of said strain of fungus, labelled by the fluorescent marker, and antifungal agent compared to the chitin level of a population of cells of said strain of fungus in the absence of antifungal agent;

According to an especial embodiment the present invention relates to a method for determining the degree of sensitivity, corresponding to a resistant phenotype, of a population of cells of a strain of fungus, said fungus being an unicellular or multicellular fungus, to an antifungal agent, comprising:
  a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
  b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
  c. a step of quantifying the chitin level, by high-content analysis fluorescence microscopy, of the labelled cells of said strain of fungus in the mixture obtained in the previous step;
  d. a step of determining a lack of any increase in the chitin level or an increase in the chitin level of less than 10% in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent.

According to an especial embodiment the present invention relates to a method for determining the degree of sensitivity, corresponding to a resistant phenotype, of a population of cells of a strain of fungus, said fungus being an unicellular or multicellular fungus, to an antifungal agent, comprising:
  a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
  b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
  c. a step of quantifying the chitin level, by high-content analysis fluorescence microscopy, of the labelled cells of said strain of fungus in the mixture obtained in the previous step;
  d. a step of determining an increase in the chitin level of less than 10%, or a decrease in the chitin level especially of less than 20%, or an unchanged level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent.

According to an especial embodiment the present invention relates to a method for determining the degree of sensitivity, corresponding to an intermediate phenotype, of a population of cells of a strain of fungus, said fungus being an unicellular fungus, to an antifungal agent, comprising:
  a. a step of contacting cells of said strain of fungus with a concentration of antifungal agent varying from 0.0009 to 130 µg/ml, so as to obtain a mixture of cells of said strain of fungus with the antifungal agent;
  b. a step of adding a fluorescent marker to the mixture of cells of said strain of fungus and antifungal agent obtained previously, so as to obtain a mixture of cells of said strain of fungus, labelled by the fluorescent marker, and antifungal agent;
  c. a step of quantifying the chitin level by fluorescence microscopy of the labelled cells of said strain of fungus in the mixture obtained in the previous step;
  d. a step of determining an increase in the chitin level of from 10% to a value less than 20% in the mixture of cells of said strain of fungus, labelled by the fluorescent marker, and antifungal agent compared to the chitin level of a population of cells of said strain of fungus in the absence of antifungal agent; or
  e. a step of determining an increase in the chitin level greater than or equal to 20% in the mixture of cells of said strain of fungus, labelled by the fluorescent marker, and antifungal agent compared to the chitin level of a population of cells of said strain of fungus in the absence of antifungal agent; followed by
  f. a step of counting the cells in the mixture of cells of said strain of fungus labelled by the fluorescent marker and antifungal agent; then by
  g. a step of determining a decrease in the number of cells of less than 0.3 log, or an unchanged number of cells as a function of the concentrations of antifungal agent in the population of cells of said strain of fungus compared to the number of cells in a population of cells of said strain of fungus in the absence of antifungal agent.

According to an especial embodiment the present invention relates to a method for determining the degree of sensitivity, corresponding to an intermediate phenotype, of a population of cells of a strain of fungus, said fungus being a multicellular fungus, to an antifungal agent, comprising:
  a. a step of contacting cells of said strain of fungus with a concentration of antifungal agent varying from 0.0009 to 130 µg/ml, so as to obtain a mixture of cells of said strain of fungus with the antifungal agent;
  b. a step of adding a fluorescent marker to the mixture of cells of said strain of fungus and antifungal agent obtained previously, so as to obtain a mixture of cells of said strain of fungus, labelled by the fluorescent marker, and antifungal agent;
  c. a step of quantifying the chitin level by fluorescence microscopy of the labelled cells of said strain of fungus in the mixture obtained in the previous step;
  d. a step of determining an increase in the chitin level between 10% and a value less than 20% in the mixture of cells of said strain of fungus, labelled by the fluorescent marker, and antifungal agent compared to the chitin level of a population of cells of said strain of fungus in the absence of antifungal agent; or
  e. a step of determining an increase in the chitin level greater than or equal to 20% in the mixture of cells of said strain of fungus, labelled by the fluorescent marker, and antifungal agent compared to the chitin level of a population of cells of said strain of fungus in the absence of antifungal agent; followed by f. a step of measuring the length of the vegetative germination hypha in the mixture of cells of said strain of fungus labelled by the fluorescent marker and antifungal agent; then by g. a step of determining a decrease in the length of the vegetative germination hypha, or an unchanged length of said hypha as a function of the concentrations of antifungal agent in the population of cells of said strain of fungus compared to the length of vegetative germination hypha of a population of cells of said strain of fungus in the absence of antifungal agent;

According to an especial embodiment the present invention relates to a method for determining the degree of sensitivity, corresponding to an intermediate phenotype, of a population of cells of a strain of fungus, said fungus being an unicellular fungus, to an antifungal agent, comprising:

a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining an increase in the chitin level of from 10% to a value less than 20% in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent; or e. a step of determining an increase in the chitin level greater than or equal to 20% in the mixture of cells of said strain of fungus, labelled by the fluorescent marker, and antifungal agent compared to the chitin level of a population of cells of said strain of fungus in the absence of antifungal agent; followed by f. a step of counting the cells in the mixture of cells of said strain of fungus, labelled by Calcofluor White, and antifungal agent after said step of quantifying the chitin level; then by g. a step of determining a decrease in the number of cells of less than 0.3 log, or an unchanged number of cells as a function of the concentration of antifungal agent in the population of cells of said strain of fungus compared to the number of cells in a population of cells of said strain of fungus in the absence of antifungal agent.

According to an especial embodiment the present invention relates to a method for determining the degree of sensitivity, corresponding to an intermediate phenotype, of a population of cells of a strain of fungus, said fungus being a multicellular fungus, to an antifungal agent, comprising:

a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining an increase in the chitin level between 10% and a value less than 20% in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent; or e. a step of determining an increase in the chitin level greater than or equal to 20% in the mixture of cells of said strain of fungus, labelled by the fluorescent marker, and antifungal agent compared to the chitin level of a population of cells of said strain of fungus in the absence of antifungal agent; followed by f. a step of measuring the length of the vegetative germination hypha in the mixture of cells of said strain of fungus, labelled by Calcofluor White, and antifungal agent, then by g. a step of determining a decrease in the length of the vegetative germination hypha, or an unchanged length of said hypha as a function of the concentration of antifungal agent in the population of cells of said strain of fungus compared to the length of vegetative germination hypha of a population of cells of said strain of fungus in the absence of antifungal agent.

According to an especial embodiment the present invention relates to a method for determining the degree of sensitivity, corresponding to a sensitive phenotype, of a population of cells of a strain of fungus, said fungus being an unicellular fungus, to an antifungal agent, comprising:

a. a step of contacting cells of said strain of fungus with a concentration of antifungal agent varying from 0.0009 to 130 µg/ml, so as to obtain a mixture of cells of said strain of fungus with the antifungal agent;

b. a step of adding a fluorescent marker to the mixture of cells of said strain of fungus and antifungal agent obtained previously, so as to obtain a mixture of cells of said strain of fungus, labelled by the fluorescent marker, and antifungal agent;

c. a step of quantifying the chitin level by fluorescence microscopy of the labelled cells of said strain of fungus in the mixture obtained in the previous step;

d. a step of determining an increase in the chitin level having a value greater than or equal to 20% in the mixture of cells of said strain of fungus, labelled by the fluorescent marker, and antifungal agent compared to the chitin level of a population of cells of said strain of fungus in the absence of antifungal agent; followed by e. a step of counting the cells in the mixture of cells of said strain of fungus labelled by the fluorescent marker and antifungal agent; then by f. a step of determining a decrease in the number of cells of at least 0.3 log as a function of the concentrations of antifungal agent in the population of cells of said strain of fungus compared to the number of cells in a population of cells of said strain of fungus in the absence of antifungal agent.

According to an especial embodiment the present invention relates to a method for determining the degree of sensitivity, corresponding to a sensitive phenotype, of a population of cells of a strain of fungus, said fungus being a multicellular fungus, to an antifungal agent, comprising:
a. a step of contacting cells of said strain of fungus with a concentration of antifungal agent varying from 0.0009 to 130 µg/ml, so as to obtain a mixture of cells of said strain of fungus with the antifungal agent;
b. a step of adding a fluorescent marker to the mixture of cells of said strain of fungus and antifungal agent obtained previously, so as to obtain a mixture of cells of said strain of fungus, labelled by the fluorescent marker, and antifungal agent;
c. a step of quantifying the chitin level by fluorescence microscopy of the labelled cells of said strain of fungus in the mixture obtained in the previous step;
d. a step of determining an increase in the chitin level having a value greater than or equal to 20% in the mixture of cells of said strain of fungus, labelled by the fluorescent marker, and antifungal agent compared to the chitin level of a population of cells of said strain of fungus in the absence of antifungal agent; followed by
e. a step of measuring the length of the vegetative germination hypha in the mixture of cells of said strain of fungus labelled by the fluorescent marker and antifungal agent, then by
f. a step of determining a decrease in the length of the vegetative germination hypha, or an unchanged length of said hypha as a function of the concentrations of antifungal agent in the population of cells of said strain of fungus compared to the length of vegetative germination hypha of a population of cells of said strain of fungus in the absence of antifungal agent.

According to an especial embodiment the present invention relates to a method for determining the degree of sensitivity, corresponding to a sensitive phenotype, of a population of cells of a strain of fungus, said fungus being an unicellular fungus, to an antifungal agent, comprising:
a. a step of contacting cells of said strain of fungus with a gradient of concentrations of antifungal agent varying from 0.0009 to 130 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
c. a step of quantifying the chitin level, by high-content analysis fluorescence microscopy, of the labelled cells of said strain of fungus in the mixture obtained in the previous step;
d. a step of determining an increase in the chitin level of at least 20% in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent; followed by
e. a step of counting the cells in the mixture of cells of said strain of fungus, labelled by Calcofluor White, and antifungal agent, then by
f. a step of determining a decrease in the number of cells of at least 0.3 log as a function of the concentration of antifungal agent in the population of cells of said strain of fungus compared to the number of cells in a population of cells of said strain of fungus in the absence of antifungal agent.

According to an especial embodiment the present invention relates to a method for determining the degree of sensitivity, corresponding to a sensitive phenotype, of a population of cells of a strain of fungus, said fungus being a multicellular fungus, to an antifungal agent, comprising:
a. a step of contacting cells of said strain of fungus with a gradient of concentrations of antifungal agent varying from 0.0009 to 130 µg/ml, at a temperature of from 30 to 35° C., for a period of time less than or equal to 48 h, especially for a period of time of from 6.5 h to 24 h, so as to obtain a mixture of cells of said strain of fungus and antifungal agent;
b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
c. a step of quantifying the chitin level, by high-content analysis fluorescence microscopy, of the labelled cells of said strain of fungus in the mixture obtained in the previous step;
d. a step of determining an increase in the chitin level having a value greater than or equal to 20% in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent; followed by
e. a step of measuring the length of the vegetative germination hypha in the mixture of cells of said strain of fungus, labelled by Calcofluor White, and antifungal agent; then by
f. a step of determining a decrease in the length of the vegetative germination hypha, or an unchanged length of said hypha as a function of the concentration of antifungal agent in the population of cells of said strain of fungus compared to the length of vegetative germination hypha in a population of cells of said strain of fungus in the absence of antifungal agent.

According to an especial embodiment the present invention relates to a method for determining the degree of sensitivity, corresponding to a sensitive phenotype, of a population of cells of the strain SC5314 of *C. albicans* to fluconazole, comprising:
a. a step of contacting cells of said strain SC5314 of *C. albicans* with a gradient of concentrations of fluconazole varying from 0.015 to 16 µg/ml, more especially from 0.015 to 0.031 µg/ml, from 0.015 to 0.062 µg/ml, from 0.015 to 0.125 µg/ml, from 0.015 to 0.25 µg/ml, from 0.015 to 0.5 µg/ml, from 0.015 to 1 µg/ml, from 0.015 to 2 µg/ml, from 0.015 to 4 µg/ml, from 0.015 to 8 µg/ml, from 0.015 to 16 µg/ml, for a period of time of 6.5 h, at a temperature of 30° C.; so as to obtain a mixture of cells of said strain SC5314 of *C. albicans* and fluconazole;
b. a step of adding the fluorescent marker Calcofluor White to the mixture of cells of said strain SC5314 of C. albicans and fluconazole obtained previously, so as to obtain a mixture of cells of said strain SC5314 of C. albicans, labelled by the fluorescent marker Calcofluor White, and fluconazole;

c. a step of quantifying the chitin level, by high-content analysis fluorescence microscopy, of the labelled cells of said strain SC5314 of C. albicans in the mixture obtained in the previous step;

d. a step of determining an increase in the chitin level having a value greater than or equal to 20% in the mixture of cells of said strain of fungus, labelled by the fluorescent marker Calcofluor White, and fluconazole as a function of the concentration of fluconazole in the population of cells of said strain SC5314 of C. albicans compared to the chitin level of a population of cells of said strain SC5314 of C. albicans in the absence of fluconazole;

e. a step of counting the cells in the mixture of cells of said strain SC5314 of C. albicans, labelled by the fluorescent marker Calcofluor White, and fluconazole after said step of quantifying the chitin level;

f. a step of determining a decrease in the number of cells of at least 0.3 log as a function of the concentration of fluconazole in the population of cells of said strain SC5314 of C. albicans compared to the number of cells in a population of cells of said strain SC5314 of C. albicans in the absence of fluconazole.

According to an especial embodiment the present invention relates to a method for determining the degree of sensitivity, corresponding to a sensitive phenotype, of a population of cells of the strain SC5314 of C. albicans to voriconazole, comprising:

a. a step of contacting cells of said strain SC5314 of C. albicans with a gradient of concentrations of voriconazole varying from 0.004 to 5 µg/ml, more especially from 0.004 to 0.009 µg/ml, from 0.004 to 0.019 µg/ml, from 0.004 to 0.039 µg/ml, from 0.004 to 0.078 µg/ml, from 0.004 to 0.156 µg/ml, from 0.004 to 0.312 µg/ml, from 0.004 to 0.0625 µg/ml, from 0.004 to 1.25 µg/ml, from 0.004 to 2.5 µg/ml, from 0.004 to 5 µg/ml, for a period of time of 6.5 h, at a temperature of 30° C.; so as to obtain a mixture of cells of said strain SC5314 of C. albicans and voriconazole;

b. a step of adding the fluorescent marker Calcofluor White to the mixture of cells of said strain SC5314 of C. albicans and voriconazole obtained previously, so as to obtain a mixture of cells of said strain SC5314 of C. albicans, labelled by the fluorescent marker Calcofluor White, and voriconazole;

c. a step of quantifying the chitin level, by high-content analysis fluorescence microscopy, of the labelled cells of said strain SC5314 of C. albicans in the mixture obtained in the previous step;

d. a step of determining an increase in the chitin level having a value greater than or equal to 20% in the mixture of cells of said strain SC5314 of C. albicans, labelled by the fluorescent marker Calcofluor White, and voriconazole as a function of the concentration of voriconazole in the population of cells of said strain SC5314 of C. albicans compared to the chitin level of a population of cells of said strain SC5314 of C. albicans in the absence of voriconazole; followed by e. a step of counting the cells in the mixture of cells of said strain SC5314 of C. albicans, labelled by the fluorescent marker Calcofluor White, and voriconazole, then by f. a step of determining a decrease in the number of cells of at least 0.3 log as a function of the concentration of voriconazole in the population of cells of said strain SC5314 of C. albicans compared to the number of cells in a population of cells of said strain SC5314 of C. albicans in the absence of voriconazole.

According to an especial embodiment the present invention relates to a method for determining the degree of sensitivity, corresponding to a sensitive phenotype, of a population of cells of the strain SC5314 of C. albicans to micafungin, comprising:

a. a step of contacting cells of said strain SC5314 of C. albicans with a gradient of concentrations of micafungin varying from 0.0009 to 1 µg/ml, more especially from 0.0009 to 0.0019 µg/ml, from 0.0009 to 0.0039 µg/ml, from 0.0009 to 0.007 µg/ml, from 0.0009 to 0.015 µg/ml, from 0.0009 to 0.031 µg/ml, from 0.0009 to 0.062 µg/ml, from 0.0009 to 0.125 µg/ml, from 0.0009 to 0.25 µg/ml, from 0.0009 to 0.5 µg/ml, from 0.0009 to 1 µg/ml, for a period of time of 6.5 h, at a temperature of 30° C.; so as to obtain a mixture of cells of said strain SC5314 of C. albicans and micafungin;

b. a step of adding the fluorescent marker Calcofluor White to the mixture of cells of said strain SC5314 of C. albicans and micafungin obtained previously, so as to obtain a mixture of cells of said strain SC5314 of C. albicans, labelled by the fluorescent marker Calcofluor White, and micafungin;

c. a step of quantifying the chitin level, by high-content analysis fluorescence microscopy, of the labelled cells of said strain SC5314 of C. albicans in the mixture obtained in the previous step;

d. a step of determining an increase in the chitin level having a value greater than or equal to 20% in the mixture of cells of said strain SC5314 of C. albicans, labelled by the fluorescent marker Calcofluor White, and micafungin as a function of the concentration of micafungin in the population of cells of said strain SC5314 of C. albicans compared to the chitin level of a population of cells of said strain SC5314 of C. albicans in the absence of micafungin; followed by e. a step of counting the cells in the mixture of cells of said strain SC5314 of C. albicans, labelled by the fluorescent marker Calcofluor White, and micafungin; then by f. a step of determining a decrease in the number of cells of at least 0.3 log as a function of the concentration of micafungin in the population of cells of said strain SC5314 of C. albicans compared to the number of cells in a population of cells of said strain SC5314 of C. albicans in the absence of micafungin.

According to an especial embodiment the present invention relates to a method for determining the degree of sensitivity, corresponding to a resistant phenotype, of a population of cells of the strain DSY296 of C. albicans to fluconazole, comprising:

a. a step of contacting cells of said strain DSY296 of C. albicans with a gradient of concentrations of fluconazole varying from 0.015 to 16 µg/ml, more especially from 0.015 to 0.031 µg/ml, from 0.015 to 0.062 µg/ml, from 0.015 to 0.125 µg/ml, from 0.015 to 0.25 µg/ml, from 0.015 to 0.5 µg/ml, from 0.015 to 1 µg/ml, from 0.015 to 2 µg/ml, from 0.015 to 4 µg/ml, from 0.015 to 8 µg/ml, from 0.015 to 16 µg/ml, for a period of time of 6.5 h, at a temperature of 30° C.; so as to obtain a mixture of cells of said strain DSY296 of C. albicans and fluconazole;

b. a step of adding the fluorescent marker Calcofluor White to the mixture of cells of said strain DSY296 of *C. albicans* and fluconazole obtained previously, so as to obtain a mixture of cells of said strain DSY296 of *C. albicans*, labelled by the fluorescent marker Calcofluor White, and fluconazole;
c. a step of quantifying the chitin level, by high-content analysis fluorescence microscopy, of the labelled cells of said strain DSY296 of *C. albicans* in the mixture obtained in the previous step;
d. a step of determining a lack of any increase in the chitin level or an increase in the chitin level of less than 10% in the mixture of cells of said strain of fungus, labelled by the fluorescent marker Calcofluor White, and fluconazole as a function of the concentration of fluconazole in the population of cells of said strain DSY296 of *C. albicans* compared to the chitin level of a population of cells of said strain DSY296 of *C. albicans* in the absence of fluconazole.

According to an especial embodiment the present invention relates to a method for determining the degree of sensitivity, corresponding to a resistant phenotype, of a population of cells of the strain DSY296 of *C. albicans* to fluconazole, comprising:
  a. a step of contacting cells of said strain DSY296 of *C. albicans* with a gradient of concentrations of fluconazole varying from 0.015 to 16 µg/ml, more especially from 0.015 to 0.031 µg/ml, from 0.015 to 0.062 µg/ml, from 0.015 to 0.125 µg/ml, from 0.015 to 0.25 µg/ml, from 0.015 to 0.5 µg/ml, from 0.015 to 1 µg/ml, from 0.015 to 2 µg/ml, from 0.015 to 4 µg/ml, from 0.015 to 8 µg/ml, from 0.015 to 16 µg/ml, for a period of time of 6.5 h, at a temperature of 30° C.; so as to obtain a mixture of cells of said strain DSY296 of *C. albicans* and fluconazole;
  b. a step of adding the fluorescent marker Calcofluor White to the mixture of cells of said strain DSY296 of *C. albicans* and fluconazole obtained previously, so as to obtain a mixture of cells of said strain DSY296 of *C. albicans*, labelled by the fluorescent marker Calcofluor White, and fluconazole;
  c. a step of quantifying the chitin level, by high-content analysis fluorescence microscopy, of the labelled cells of said strain DSY296 of *C. albicans* in the mixture obtained in the previous step;
  d. a step of determining an increase in the chitin level of less than 10%, or a decrease in the chitin level especially of less than 20%, or an unchanged chitin level, in the mixture of cells of said strain of fungus, labelled by the fluorescent marker Calcofluor White, and fluconazole as a function of the concentration of fluconazole in the population of cells of said strain DSY296 of *C. albicans* compared to the chitin level of a population of cells of said strain DSY296 of *C. albicans* in the absence of fluconazole.

According to an especial embodiment the present invention relates to a method for determining the degree of sensitivity, corresponding to a resistant phenotype, of a population of cells of the strain DSY296 of *C. albicans* to fluconazole, comprising:
  a. a step of contacting cells of said strain DSY296 of *C. albicans* with a gradient of concentrations of voriconazole varying from 0.004 to 5 µg/ml, more especially from 0.004 to 0.009 µg/ml, from 0.004 to 0.019 µg/ml, from 0.004 to 0.039 µg/ml, from 0.004 to 0.078 µg/ml, from 0.004 to 0.156 µg/ml, from 0.004 to 0.312 µg/ml, from 0.004 to 0.0625 µg/ml, from 0.004 to 1.25 µg/ml, from 0.004 to 2.5 µg/ml, from 0.004 to 5 µg/ml, for a period of time of 6.5 h, at a temperature of 30° C.; so as to obtain a mixture of cells of said strain DSY296 of *C. albicans* and voriconazole;
  b. a step of adding the fluorescent marker Calcofluor White to the mixture of cells of said strain DSY296 of *C. albicans* and voriconazole obtained previously, so as to obtain a mixture of cells of said strain DSY296 of *C. albicans*, labelled by the fluorescent marker Calcofluor White, and voriconazole;
  c. a step of quantifying the chitin level, by high-content analysis fluorescence microscopy, of the labelled cells of said strain DSY296 of *C. albicans* in the mixture obtained in the previous step;
  d. a step of determining a lack of any increase in the chitin level or an increase in the chitin level of less than 10% in the mixture of cells of said strain DSY296 of *C. albicans*, labelled by the fluorescent marker Calcofluor White, and voriconazole as a function of the concentration of voriconazole in the population of cells of said strain DSY296 of *C. albicans* compared to the chitin level of a population of cells of said strain DSY296 of *C. albicans* in the absence of voriconazole.

According to an especial embodiment the present invention relates to a method for determining the degree of sensitivity, corresponding to a resistant phenotype, of a population of cells of the strain DSY296 of *C. albicans* to voriconazole, comprising:
  a. a step of contacting cells of said strain DSY296 of *C. albicans* with a gradient of concentrations of voriconazole varying from 0.004 to 5 µg/ml, more especially from 0.004 to 0.009 µg/ml, from 0.004 to 0.019 µg/ml, from 0.004 to 0.039 µg/ml, from 0.004 to 0.078 µg/ml, from 0.004 to 0.156 µg/ml, from 0.004 to 0.312 µg/ml, from 0.004 to 0.0625 µg/ml, from 0.004 to 1.25 µg/ml, from 0.004 to 2.5 µg/ml, from 0.004 to 5 µg/ml, for a period of time of 6.5 h, at a temperature of 30° C.; so as to obtain a mixture of cells of said strain DSY296 of *C. albicans* and voriconazole;
  b. a step of adding the fluorescent marker Calcofluor White to the mixture of cells of said strain DSY296 of *C. albicans* and voriconazole obtained previously, so as to obtain a mixture of cells of said strain DSY296 of *C. albicans*, labelled by the fluorescent marker Calcofluor White, and voriconazole;
  c. a step of quantifying the chitin level, by high-content analysis fluorescence microscopy, of the labelled cells of said strain DSY296 of *C. albicans* in the mixture obtained in the previous step;
  d. a step of determining an increase in the chitin level of less than 10%, or a decrease in the chitin level especially of less than 20%, or an unchanged chitin level, in the mixture of cells of said strain DSY296 of *C. albicans*, labelled by the fluorescent marker Calcofluor White, and voriconazole as a function of the concentration of voriconazole in the population of cells of said strain DSY296 of *C. albicans* compared to the chitin level of a population of cells of said strain DSY296 of *C. albicans* in the absence of voriconazole.

According to an especial embodiment the present invention relates to a method for determining the degree of sensitivity, corresponding to a resistant phenotype, of a population of cells of the strain TOP of *C. albicans* to micafungin, comprising:
  a. a step of contacting cells of said strain TOP of *C. albicans* with a gradient of concentrations of micafungin varying from 0.0009 to 1 µg/ml, more especially from 0.0009 to 0.0019 µg/ml, from 0.0009 to 0.0039 µg/ml, from 0.0009 to 0.007 µg/ml, from 0.0009 to 0.015 µg/ml, from 0.0009 to 0.031 µg/ml, from 0.0009 to 0.062 µg/ml, from 0.0009 to 0.125 µg/ml, from 0.0009 to 0.25 µg/ml, from 0.0009 to 0.5 µg/ml, from 0.0009 to 1 µg/ml, for a period of time of 6.5 h, at a temperature of 30° C.; so as to obtain a mixture of cells of said strain TOP of *C. albicans* and micafungin;
b. a step of adding the fluorescent marker Calcofluor White to the mixture of cells of said strain TOP of *C. albicans* and micafungin obtained previously, so as to obtain a mixture of cells of said strain TOP of *C. albicans*, labelled by the fluorescent marker Calcofluor White, and micafungin;
c. a step of quantifying the chitin level, by high-content analysis fluorescence microscopy, of the labelled cells of said strain TOP of *C. albicans* in the mixture obtained in the previous step;
d. a step of determining a lack of any increase in the chitin level or an increase in the chitin level of less than 10% in the mixture of cells of said strain TOP of *C. albicans*, labelled by the fluorescent marker Calcofluor White, and micafungin as a function of the concentration of micafungin in the population of cells of said strain TOP of *C. albicans* compared to the chitin level of a population of cells of said strain TOP of *C. albicans* in the absence of micafungin.

According to an especial embodiment the present invention relates to a method for determining the degree of sensitivity, corresponding to a resistant phenotype, of a population of cells of the strain TOP of *C. albicans* to micafungin, comprising:
a. a step of contacting cells of said strain TOP of *C. albicans* with a gradient of concentrations of micafungin varying from 0.0009 to 1 µg/ml, more especially from 0.0009 to 0.0019 µg/ml, from 0.0009 to 0.0039 µg/ml, from 0.0009 to 0.007 µg/ml, from 0.0009 to 0.015 µg/ml, from 0.0009 to 0.031 µg/ml, from 0.0009 to 0.062 µg/ml, from 0.0009 to 0.125 µg/ml, from 0.0009 to 0.25 µg/ml, from 0.0009 to 0.5 µg/ml, from 0.0009 to 1 µg/ml, for a period of time of 6.5 h, at a temperature of 30° C.; so as to obtain a mixture of cells of said strain TOP of *C. albicans* and micafungin;
b. a step of adding the fluorescent marker Calcofluor White to the mixture of cells of said strain TOP of *C. albicans* and micafungin obtained previously, so as to obtain a mixture of cells of said strain TOP of *C. albicans*, labelled by the fluorescent marker Calcofluor White, and micafungin;
c. a step of quantifying the chitin level, by high-content analysis fluorescence microscopy, of the labelled cells of said strain TOP of *C. albicans* in the mixture obtained in the previous step;
d. a step of determining an increase in the chitin level of less than 10%, or a decrease in the chitin level especially of less than 20%, or an unchanged chitin level, in the mixture of cells of said strain TOP of *C. albicans*, labelled by the fluorescent marker Calcofluor White, and micafungin as a function of the concentration of micafungin in the population of cells of said strain TOP of *C. albicans* compared to the chitin level of a population of cells of said strain TOP of *C. albicans* in the absence of micafungin.

According to an especial embodiment the present invention relates to a method for determining the degree of sensitivity, corresponding to an intermediate phenotype, of a population of cells of the strain ATCC®2001 of *C. glabrata* to fluconazole, comprising:
a. a step of contacting cells of said strain ATCC®2001 of *C. glabrata* with a gradient of concentrations of fluconazole varying from 0.125 to 128 µg/ml, more especially from 0.125 to 0.250n/ml, from 0.125 to 0.5 µg/ml, from 0.125 to 1 µg/ml, from 0.125 to 2 µg/ml, from 0.125 to 4 µg/ml, from 0.125 to 8 µg/ml, from 0.125 to 16 µg/ml, from 0.125 to 32 µg/ml, from 0.125 to 64 µg/ml, from 0.125 to 128 µg/ml, for a period of time of 6.5 h, at a temperature of 35° C.; so as to obtain a mixture of cells of said strain ATCC®2001 of *C. glabrata* and fluconazole;
b. a step of adding the fluorescent marker Calcofluor White to the mixture of cells of said strain ATCC®2001 of *C. glabrata* and fluconazole obtained previously, so as to obtain a mixture of cells of said strain ATCC®2001 of *C. glabrata*, labelled by the fluorescent marker Calcofluor White, and fluconazole;
c. a step of quantifying the chitin level, by high-content analysis fluorescence microscopy, of the labelled cells of said strain ATCC®2001 of *C. glabrata* in the mixture obtained in the previous step;
d. a step of determining an increase in the chitin level of from 10% to a value less than 20% in the mixture of cells of said strain ATCC®2001 of *C. glabrata*, labelled by the fluorescent marker Calcofluor White, and fluconazole as a function of the concentration of fluconazole in the population of cells of said strain ATCC®2001 of *C. glabrata* compared to the chitin level of a population of cells of said strain ATCC®2001 of *C. glabrata* in the absence of fluconazole; or
e. a step of determining an increase in the chitin level greater than or equal to 20% in the mixture of cells of said strain ATCC®2001 of *C. glabrata*, labelled by the fluorescent marker Calcofluor White, and fluconazole compared to the chitin level of a population of cells of said strain ATCC®2001 of *C. glabrata* in the absence of fluconazole; followed by
f. a step of counting the cells in the mixture of cells of said strain ATCC®2001 of *C. glabrata*, labelled by the fluorescent marker Calcofluor White, and fluconazole after said step of quantifying the chitin level; then by
g. a step of determining a decrease in the number of cells of less than 0.3 log, or an unchanged number of cells as a function of the concentration of fluconazole in the population of cells of said strain ATCC®2001 of *C. glabrata* compared to the number of cells in a population of cells of said strain ATCC®2001 of *C. glabrata* in the absence of fluconazole.

According to an especial embodiment the present invention relates to a method for determining the degree of sensitivity, corresponding to a sensitive phenotype, of a population of cells of the strain ATCC®2001 of *C. glabrata* to voriconazole, comprising:
a. a step of contacting cells of said strain ATCC®2001 of *C. glabrata* with a gradient of concentrations of voriconazole varying from 0.007 to 8 µg/ml, more especially from 0.007 to 0.015 µg/ml, from 0.007 to 0.031 µg/ml, from 0.007 to 0.062 µg/ml, from 0.007 to 0.125 µg/ml, from 0.007 to 0.25 µg/ml, from 0.007 to 0.5 µg/ml, from 0.007 to 1 µg/ml, from 0.007 to 2 µg/ml, from 0.007 to 4 µg/ml, from 0.007 to 8 µg/ml, for a period of time of 6.5 h, at a temperature of 35° C.; so as to obtain a mixture of cells of said strain ATCC®2001 of *C. glabrata* and voriconazole;

b. a step of adding the fluorescent marker Calcofluor White to the mixture of cells of said strain ATCC®2001 of *C. glabrata* and voriconazole obtained previously, so as to obtain a mixture of cells of said strain ATCC®2001 of *C. glabrata*, labelled by the fluorescent marker Calcofluor White, and voriconazole;
c. a step of quantifying the chitin level, by high-content analysis fluorescence microscopy, of the labelled cells of said strain ATCC®2001 of *C. glabrata* in the mixture obtained in the previous step;
d. a step of determining an increase in the chitin level having a value greater than or equal to 20% in the mixture of cells of said strain ATCC®2001 of *C. glabrata*, labelled by the fluorescent marker Calcofluor White, and voriconazole as a function of the concentration of voriconazole in the population of cells of said strain ATCC®2001 of *C. glabrata* compared to the chitin level of a population of cells of said strain ATCC®2001 of *C. glabrata* in the absence of voriconazole; followed by
e. a step of counting the cells in the mixture of cells of said strain ATCC®2001 of *C. glabrata*, labelled by the fluorescent marker Calcofluor White, and voriconazole, then by
f. a step of determining a decrease in the number of cells of at least 0.3 log as a function of the concentration of voriconazole in the population of cells of said strain ATCC®2001 of *C. glabrata* compared to the number of cells in a population of cells of said strain ATCC®2001 of *C. glabrata* in the absence of voriconazole.

According to an especial embodiment the present invention relates to a method for determining the degree of sensitivity, corresponding to a sensitive phenotype, of a population of cells of the strain ATCC®2001 of *C. glabrata* to micafungin, comprising:
a. a step of contacting cells of said strain ATCC®2001 of *C. glabrata* with a gradient of concentrations of micafungin varying from 0.0009 to 1 µg/ml, more especially from 0.0009 to 0.0019 µg/ml, from 0.0009 to 0.0039 µg/ml, from 0.0009 to 0.007 µg/ml, from 0.0009 to 0.015 µg/ml, from 0.0009 to 0.031 µg/ml, from 0.0009 to 0.062 µg/ml, from 0.0009 to 0.125 µg/ml, from 0.0009 to 0.25 µg/ml, from 0.0009 to 0.5 µg/ml, from 0.0009 to 1 µg/ml, for a period of time of 6.5 h, at a temperature of 35° C.; so as to obtain a mixture of cells of said strain ATCC®2001 of *C. glabrata* and micafungin;
b. a step of adding the fluorescent marker Calcofluor White to the mixture of cells of said strain ATCC®2001 of *C. glabrata* and micafungin obtained previously, so as to obtain a mixture of cells of said strain ATCC®2001 of *C. glabrata*, labelled by the fluorescent marker Calcofluor White, and micafungin;
c. a step of quantifying the chitin level, by high-content analysis fluorescence microscopy, of the labelled cells of said strain ATCC®2001 of *C. glabrata* in the mixture obtained in the previous step;
d. a step of determining an increase in the chitin level having a value greater than or equal to 20% in the mixture of cells of said strain ATCC®2001 of *C. glabrata*, labelled by the fluorescent marker Calcofluor White, and micafungin as a function of the concentration of micafungin in the population of cells of said strain ATCC®2001 of *C. glabrata* compared to the chitin level of a population of cells of said strain ATCC®2001 of *C. glabrata* in the absence of micafungin; followed by
e. a step of counting the cells in the mixture of cells of said strain ATCC®2001 of *C. glabrata*, labelled by the fluorescent marker Calcofluor White, and micafungin; then by
f. a step of determining a decrease in the number of cells of at least 0.3 log as a function of the concentration of micafungin in the population of cells of said strain ATCC®2001 of *C. glabrata* compared to the number of cells in a population of cells of said strain ATCC®2001 of *C. glabrata* in the absence of micafungin.

According to an especial embodiment the present invention relates to a method for determining the degree of sensitivity, corresponding to a resistant phenotype, of a population of cells of the strain Tg5 of *C. glabrata* to fluconazole, comprising:
a. a step of contacting cells of said strain Tg5 of *C. glabrata* with a gradient of concentrations of fluconazole varying from 0 to 128 µg/ml, more especially from 0 to 0.250 µg/ml, from 0 to 0.5 µg/ml, from 0 to 1 µg/ml, from 0 to 2 µg/ml, from 0 to 4 µg/ml, from 0 to 8 µg/ml, from 0 to 16 µg/ml, from 0 to 32 µg/ml, from 0 to 64 µg/ml, from 0 to 128 µg/ml, for a period of time of 6.5 h, at a temperature of 35° C.; so as to obtain a mixture of cells of said strain Tg5 of *C. glabrata* and fluconazole;
b. a step of adding the fluorescent marker Calcofluor White to the mixture of cells of said strain Tg5 of *C. glabrata* and fluconazole obtained previously, so as to obtain a mixture of cells of said strain Tg5 of *C. glabrata*, labelled by the fluorescent marker Calcofluor White, and fluconazole;
c. a step of quantifying the chitin level, by high-content analysis fluorescence microscopy, of the labelled cells of said strain Tg5 of *C. glabrata* in the mixture obtained in the previous step;
d. a step of determining a lack of any increase in the chitin level or an increase in the chitin level of less than 10% in the mixture of cells of said strain Tg5 of *C. glabrata*, labelled by the fluorescent marker Calcofluor White, and fluconazole as a function of the concentration of fluconazole in the population of cells of said strain Tg5 of *C. glabrata* compared to the chitin level of a population of cells of said strain Tg5 of *C. glabrata* in the absence of fluconazole.

According to an especial embodiment the present invention relates to a method for determining the degree of sensitivity, corresponding to a resistant phenotype, of a population of cells of the strain Tg5 of *C. glabrata* to fluconazole, comprising:
a. a step of contacting cells of said strain Tg5 of *C. glabrata* with a gradient of concentrations of fluconazole varying from 0 to 128 µg/ml, more especially from 0 to 0.250n/ml, from 0 to 0.5 µg/ml, from 0 to 1 µg/ml, from 0 to 2 µg/ml, from 0 to 4 µg/ml, from 0 to 8 µg/ml, from 0 to 16 µg/ml, from 0 to 32 µg/ml, from 0 to 64 µg/ml, from 0 to 128 µg/ml, for a period of time of 6.5 h, at a temperature of 35° C.; so as to obtain a mixture of cells of said strain Tg5 of *C. glabrata* and fluconazole;
b. a step of adding the fluorescent marker Calcofluor White to the mixture of cells of said strain Tg5 of *C. glabrata* and fluconazole obtained previously, so as to obtain a mixture of cells of said strain Tg5 of *C. glabrata*, labelled by the fluorescent marker Calcofluor White, and fluconazole;

c. a step of quantifying the chitin level, by high-content analysis fluorescence microscopy, of the labelled cells of said strain Tg5 of *C. glabrata* in the mixture obtained in the previous step;

d. a step of determining an increase in the chitin level of less than 10%, or a decrease in the chitin level especially of less than 20%, or an unchanged chitin level, in the mixture of cells of said strain Tg5 of *C. glabrata*, labelled by the fluorescent marker Calcofluor White, and fluconazole as a function of the concentration of fluconazole in the population of cells of said strain Tg5 of *C. glabrata* compared to the chitin level of a population of cells of said strain Tg5 of *C. glabrata* in the absence of fluconazole.

According to an especial embodiment the present invention relates to a method for determining the degree of sensitivity, corresponding to a resistant phenotype, of a population of cells of the strain Tg5 of *C. glabrata* to fluconazole, comprising:

a. a step of contacting cells of said strain Tg5 of *C. glabrata* with a gradient of concentrations of voriconazole varying from 0.007 to 8 μg/ml, more especially from 0.007 to 0.015 μg/ml, from 0.007 to 0.031 μg/ml, from 0.007 to 0.062 μg/ml, from 0.007 to 0.125 μg/ml, from 0.007 to 0.25 μg/ml, from 0.007 to 0.5 μg/ml, from 0.007 to 1 μg/ml, from 0.007 to 2 μg/ml, from 0.007 to 4 μg/ml, from 0.007 to 8 μg/ml, for a period of time of 6.5 h, at a temperature of 35° C.; so as to obtain a mixture of cells of said strain Tg5 of *C. glabrata* and voriconazole;

b. a step of adding the fluorescent marker Calcofluor White to the mixture of cells of said strain Tg5 of *C. glabrata* and voriconazole obtained previously, so as to obtain a mixture of cells of said strain Tg5 of *C. glabrata*, labelled by the fluorescent marker Calcofluor White, and voriconazole;

c. a step of quantifying the chitin level, by high-content analysis fluorescence microscopy, of the labelled cells of said strain Tg5 of *C. glabrata* in the mixture obtained in the previous step;

d. a step of determining a lack of any increase in the chitin level or an increase in the chitin level of less than 10% in the mixture of cells of said strain Tg5 of *C. glabrata*, labelled by the fluorescent marker Calcofluor White, and voriconazole as a function of the concentration of voriconazole in the population of cells of said strain Tg5 of *C. glabrata* compared to the chitin level of a population of cells of said strain Tg5 of *C. glabrata* in the absence of voriconazole.

According to an especial embodiment the present invention relates to a method for determining the degree of sensitivity, corresponding to a resistant phenotype, of a population of cells of the strain Tg5 of *C. glabrata* to voriconazole, comprising:

a. a step of contacting cells of said strain Tg5 of *C. glabrata* with a gradient of concentrations of voriconazole varying from 0.007 to 8 μg/ml, more especially from 0.007 to 0.015 μg/ml, from 0.007 to 0.031 μg/ml, from 0.007 to 0.062 μg/ml, from 0.007 to 0.125 μg/ml, from 0.007 to 0.25 μg/ml, from 0.007 to 0.5 μg/ml, from 0.007 to 1 μg/ml, from 0.007 to 2 μg/ml, from 0.007 to 4 μg/ml, from 0.007 to 8 μg/ml, for a period of time of 6.5 h, at a temperature of 35° C.; so as to obtain a mixture of cells of said strain Tg5 of *C. glabrata* and voriconazole;

b. a step of adding the fluorescent marker Calcofluor White to the mixture of cells of said strain Tg5 of *C. glabrata* and voriconazole obtained previously, so as to obtain a mixture of cells of said strain Tg5 of *C. glabrata*, labelled by the fluorescent marker Calcofluor White, and voriconazole;

c. a step of quantifying the chitin level, by high-content analysis fluorescence microscopy, of the labelled cells of said strain Tg5 of *C. glabrata* in the mixture obtained in the previous step;

d. a step of determining an increase in the chitin level of less than 10%, or a decrease in the chitin level especially of less than 20%, or an unchanged chitin level, in the mixture of cells of said strain Tg5 of *C. glabrata*, labelled by the fluorescent marker Calcofluor White, and voriconazole as a function of the concentration of voriconazole in the population of cells of said strain Tg5 of *C. glabrata* compared to the chitin level of a population of cells of said strain Tg5 of *C. glabrata* in the absence of voriconazole.

According to an especial embodiment the present invention relates to a method for determining the degree of sensitivity, corresponding to a resistant phenotype, of a population of cells of the strain Tg5 of *C. glabrata* to micafungin, comprising:

a. a step of contacting cells of said strain Tg5 of *C. glabrata* with a gradient of concentrations of micafungin varying from 0.0009 to 1 μg/ml, more especially from 0.0009 to 0.0019 μg/ml, from 0.0009 to 0.0039 μg/ml, from 0.0009 to 0.007 μg/ml, from 0.0009 to 0.015 μg/ml, from 0.0009 to 0.031 μg/ml, from 0.0009 to 0.062 μg/ml, from 0.0009 to 0.125 μg/ml, from 0.0009 to 0.25 μg/ml, from 0.0009 to 0.5 μg/ml, from 0.0009 to 1 μg/ml, for a period of time of 6.5 h, at a temperature of 35° C.; so as to obtain a mixture of cells of said strain Tg5 of *C. glabrata* and micafungin;

b. a step of adding the fluorescent marker Calcofluor White to the mixture of cells of said strain Tg5 of *C. glabrata* and micafungin obtained previously, so as to obtain a mixture of cells of said strain Tg5 of *C. glabrata*, labelled by the fluorescent marker Calcofluor White, and micafungin;

c. a step of quantifying the chitin level, by high-content analysis fluorescence microscopy, of the labelled cells of said strain Tg5 of *C. glabrata* in the mixture obtained in the previous step;

d. a step of determining a lack of any increase in the chitin level or an increase in the chitin level of less than 10% in the mixture of cells of said strain Tg5 of *C. glabrata*, labelled by the fluorescent marker Calcofluor White, and micafungin as a function of the concentration of micafungin in the population of cells of said strain Tg5 of *C. glabrata* compared to the chitin level of a population of cells of said strain Tg5 of *C. glabrata* in the absence of micafungin.

According to an especial embodiment the present invention relates to a method for determining the degree of sensitivity, corresponding to a resistant phenotype, of a population of cells of the strain Tg5 of *C. glabrata* to micafungin, comprising:

a. a step of contacting cells of said strain Tg5 of *C. glabrata* with a gradient of concentrations of micafungin varying from 0.0009 to 1 μg/ml, more especially from 0.0009 to 0.0019 μg/ml, from 0.0009 to 0.0039 μg/ml, from 0.0009 to 0.007 μg/ml, from 0.0009 to 0.015 μg/ml, from 0.0009 to 0.031 μg/ml, from 0.0009 to 0.062 μg/ml, from 0.0009 to 0.125 μg/ml, from 0.0009 to 0.25 μg/ml, from 0.0009 to 0.5 μg/ml, from 0.0009 to 1 μg/ml, for a period of time of 6.5 h, at a temperature of 35° C.; so as to obtain a mixture of cells of said strain Tg5 of *C. glabrata* and micafungin;
b. a step of adding the fluorescent marker Calcofluor White to the mixture of cells of said strain Tg5 of *C. glabrata* and micafungin obtained previously, so as to obtain a mixture of cells of said strain Tg5 of *C. glabrata*, labelled by the fluorescent marker Calcofluor White, and micafungin;
c. a step of quantifying the chitin level, by high-content analysis fluorescence microscopy, of the labelled cells of said strain Tg5 of *C. glabrata* in the mixture obtained in the previous step;
d. a step of determining an increase in the chitin level of less than 10%, or a decrease in the chitin level especially of less than 20%, or an unchanged chitin level, in the mixture of cells of said strain Tg5 of *C. glabrata*, labelled by the fluorescent marker Calcofluor White, and micafungin as a function of the concentration of micafungin in the population of cells of said strain Tg5 of *C. glabrata* compared to the chitin level of a population of cells of said strain Tg5 of *C. glabrata* in the absence of micafungin.

According to an especial embodiment the present invention relates to a method for determining the degree of sensitivity, corresponding to a sensitive phenotype, of a population of cells of the strain ATCC®7349 of *C. tropicalis* to fluconazole, comprising:
a. a step of contacting cells of said strain ATCC®7349 of *C. tropicalis* with a gradient of concentrations of fluconazole varying from 0.015 to 16 µg/ml, more especially from 0.015 to 0.031 µg/ml, from 0.015 to 0.062 µg/ml, from 0.015 to 0.125 µg/ml, from 0.015 to 0.25 µg/ml, from 0.015 to 0.5 µg/ml, from 0.015 to 1 µg/ml, from 0.015 to 2 µg/ml, from 0.015 to 4 µg/ml, from 0.015 to 8 µg/ml, from 0.015 to 16 µg/ml, for a period of time of 6.5 h, at a temperature of 30° C.; so as to obtain a mixture of cells of said strain ATCC®7349 of *C. tropicalis* and fluconazole;
b. a step of adding the fluorescent marker Calcofluor White to the mixture of cells of said strain ATCC®7349 of *C. tropicalis* and fluconazole obtained previously, so as to obtain a mixture of cells of said strain ATCC®7349 of *C. tropicalis*, labelled by the fluorescent marker Calcofluor White, and fluconazole;
c. a step of quantifying the chitin level, by high-content analysis fluorescence microscopy, of the labelled cells of said strain ATCC®7349 of *C. tropicalis* in the mixture obtained in the previous step;
d. a step of determining an increase in the chitin level having a value greater than or equal to 20% in the mixture of cells of said strain ATCC®7349 of *C. tropicalis*, labelled by the fluorescent marker Calcofluor White, and fluconazole as a function of the concentration of micafungin in the population of cells of said strain ATCC®7349 of *C. tropicalis* compared to the chitin level of a population of cells of said strain ATCC®7349 of *C. tropicalis* in the absence of fluconazole; followed by
e. a step of counting the cells in the mixture of cells of said strain ATCC®7349 of *C. tropicalis*, labelled by the fluorescent marker Calcofluor White, and fluconazole; then by
f. a step of determining a decrease in the number of cells of at least 0.3 log as a function of the concentration of fluconazole in the population of cells of said strain ATCC®7349 of *C. tropicalis* compared to the number of cells in a population of cells of said strain ATCC®7349 of *C. tropicalis* in the absence of fluconazole.

According to an especial embodiment the present invention relates to a method for determining the degree of sensitivity, corresponding to a sensitive phenotype, of a population of cells of the strain ATCC®7349 of *C. tropicalis* to voriconazole, comprising:
a. a step of contacting cells of said strain ATCC®7349 of *C. tropicalis* with a gradient of concentrations of voriconazole varying from 0.004 to 5 µg/ml, more especially from 0.004 to 0.009 µg/ml, from 0.004 to 0.019 µg/ml, from 0.004 to 0.039 µg/ml, from 0.004 to 0.078 µg/ml, from 0.004 to 0.156 µg/ml, from 0.004 to 0.312 µg/ml, from 0.004 to 0.0625 µg/ml, from 0.004 to 1.25 µg/ml, from 0.004 to 2.5 µg/ml, from 0.004 to 5 µg/ml, for a period of time of 6.5 h, at a temperature of 30° C.; so as to obtain a mixture of cells of said strain ATCC®7349 of *C. tropicalis* and voriconazole;
b. a step of adding the fluorescent marker Calcofluor White to the mixture of cells of said strain ATCC®7349 of *C. tropicalis* and voriconazole obtained previously, so as to obtain a mixture of cells of said strain ATCC®7349 of *C. tropicalis*, labelled by the fluorescent marker Calcofluor White, and voriconazole;
c. a step of quantifying the chitin level, by high-content analysis fluorescence microscopy, of the labelled cells of said strain ATCC®7349 of *C. tropicalis* in the mixture obtained in the previous step;
d. a step of determining an increase in the chitin level having a value greater than or equal to 20% in the mixture of cells of said strain ATCC®7349 of *C. tropicalis*, labelled by the fluorescent marker Calcofluor White, and voriconazole as a function of the concentration of voriconazole in the population of cells of said strain ATCC®7349 of *C. tropicalis* compared to the chitin level of a population of cells of said strain ATCC®7349 of *C. tropicalis* in the absence of voriconazole; followed by
e. a step of counting the cells in the mixture of cells of said strain ATCC®7349 of *C. tropicalis*, labelled by the fluorescent marker Calcofluor White, and voriconazole, then by
f. a step of determining a decrease in the number of cells of at least 0.3 log as a function of the concentration of voriconazole in the population of cells of said strain ATCC®7349 of *C. tropicalis* compared to the number of cells in a population of cells of said strain ATCC®7349 of *C. tropicalis* in the absence of voriconazole.

According to an especial embodiment the present invention relates to a method for determining the degree of sensitivity, corresponding to a sensitive phenotype, of a population of cells of the strain ATCC®7349 of *C. tropicalis* to micafungin, comprising:
a. a step of contacting cells of said strain ATCC®7349 of *C. tropicalis* with a gradient of concentrations of micafungin varying from 0.0009 to 1 µg/ml, more especially from 0.0009 to 0.0019 µg/ml, from 0.0009 to 0.0039 µg/ml, from 0.0009 to 0.007 µg/ml, from 0.0009 to 0.015 µg/ml, from 0.0009 to 0.031 µg/ml, from 0.0009 to 0.062 µg/ml, from 0.0009 to 0.125 µg/ml, from 0.0009 to 0.25 µg/ml, from 0.0009 to 0.5 µg/ml, from 0.0009 to 1 µg/ml, for a period of time of 6.5 h, at a temperature of 30° C.; so as to obtain a mixture of cells of said strain ATCC®7349 of *C. tropicalis* and micafungin;

b. a step of adding the fluorescent marker Calcofluor White to the mixture of cells of said strain ATCC®7349 of *C. tropicalis* and micafungin obtained previously, so as to obtain a mixture of cells of said strain ATCC®7349 of *C. tropicalis*, labelled by the fluorescent marker Calcofluor White, and micafungin;

c. a step of quantifying the chitin level, by high-content analysis fluorescence microscopy, of the labelled cells of said strain ATCC®7349 of *C. tropicalis* in the mixture obtained in the previous step;

d. a step of determining an increase in the chitin level having a value greater than or equal to 20% in the mixture of cells of said strain ATCC®7349 of *C. tropicalis*, labelled by the fluorescent marker Calcofluor White, and micafungin as a function of the concentration of micafungin in the population of cells of said strain ATCC®7349 of *C. tropicalis* compared to the chitin level of a population of cells of said strain ATCC®7349 of *C. tropicalis* in the absence of micafungin; followed by e. a step of counting the cells in the mixture of cells of said strain ATCC®7349 of *C. tropicalis*, labelled by the fluorescent marker Calcofluor White, and micafungin, then by f. a step of determining a decrease in the number of cells of at least 0.3 log as a function of the concentration of micafungin in the population of cells of said strain ATCC®7349 of *C. tropicalis* compared to the number of cells in a population of cells of said strain ATCC®7349 of *C. tropicalis* in the absence of micafungin.

According to an especial embodiment the present invention relates to a method for determining the degree of sensitivity, corresponding to a resistant phenotype, of a population of cells of the strain 13/5 of *C. tropicalis* to micafungin, comprising:

a. a step of contacting cells of said strain 13/5 of *C. tropicalis* with a gradient of concentrations of micafungin varying from 0.0009 to 1 µg/ml, more especially from 0.0009 to 0.0019 µg/ml, from 0.0009 to 0.0039 µg/ml, from 0.0009 to 0.007 µg/ml, from 0.0009 to 0.015 µg/ml, from 0.0009 to 0.031 µg/ml, from 0.0009 to 0.062 µg/ml, from 0.0009 to 0.125 µg/ml, from 0.0009 to 0.25 µg/ml, from 0.0009 to 0.5 µg/ml, from 0.0009 to 1 µg/ml, for a period of time of 6.5 h, at a temperature of 30° C.; so as to obtain a mixture of cells of said strain 13/5 of *C. tropicalis* and micafungin;

b. a step of adding the fluorescent marker Calcofluor White to the mixture of cells of said strain 13/5 of *C. tropicalis* and micafungin obtained previously, so as to obtain a mixture of cells of said strain 13/5 of *C. tropicalis*, labelled by the fluorescent marker Calcofluor White, and micafungin;

c. a step of quantifying the chitin level, by high-content analysis fluorescence microscopy, of the labelled cells of said strain 13/5 of *C. tropicalis* in the mixture obtained in the previous step;

d. a step of determining a lack of any increase in the chitin level or an increase in the chitin level of less than 10% in the mixture of cells of said strain 13/5 of *C. tropicalis*, labelled by the fluorescent marker Calcofluor White, and micafungin as a function of the concentration of micafungin in the population of cells of said strain 13/5 of *C. tropicalis* compared to the chitin level of a population of cells of said strain 13/5 of *C. tropicalis* in the absence of micafungin.

According to an especial embodiment the present invention relates to a method for determining the degree of sensitivity, corresponding to a resistant phenotype, of a population of cells of the strain 13/5 of *C. tropicalis* to micafungin, comprising:

a. a step of contacting cells of said strain 13/5 of *C. tropicalis* with a gradient of concentrations of micafungin varying from 0.0009 to 1 µg/ml, more especially from 0.0009 to 0.0019 µg/ml, from 0.0009 to 0.0039 µg/ml, from 0.0009 to 0.007 µg/ml, from 0.0009 to 0.015 µg/ml, from 0.0009 to 0.031 µg/ml, from 0.0009 to 0.062 µg/ml, from 0.0009 to 0.125 µg/ml, from 0.0009 to 0.25 µg/ml, from 0.0009 to 0.5 µg/ml, from 0.0009 to 1 µg/ml, for a period of time of 6.5 h, at a temperature of 30° C.; so as to obtain a mixture of cells of said strain 13/5 of *C. tropicalis* and micafungin;

b. a step of adding the fluorescent marker Calcofluor White to the mixture of cells of said strain 13/5 of *C. tropicalis* and micafungin obtained previously, so as to obtain a mixture of cells of said strain 13/5 of *C. tropicalis*, labelled by the fluorescent marker Calcofluor White, and micafungin;

c. a step of quantifying the chitin level, by high-content analysis fluorescence microscopy, of the labelled cells of said strain 13/5 of *C. tropicalis* in the mixture obtained in the previous step;

d. a step of determining an increase in the chitin level of less than 10%, or a decrease in the chitin level especially of less than 20%, or an unchanged chitin level, in the mixture of cells of said strain 13/5 of *C. tropicalis*, labelled by the fluorescent marker Calcofluor White, and micafungin as a function of the concentration of micafungin in the population of cells of said strain 13/5 of *C. tropicalis* compared to the chitin level of a population of cells of said strain 13/5 of *C. tropicalis* in the absence of micafungin.

According to an especial embodiment the present invention relates to a method for determining the degree of sensitivity, corresponding to a sensitive phenotype, of a population of cells of the strain ATCC®7349 of *C. tropicalis* to fluconazole, comprising:

a. a step of contacting cells of said strain ATCC®22019 of *C. parapsilosis* with a gradient of concentrations of fluconazole varying from 0.015 to 16 µg/ml, more especially from 0.015 to 0.031 µg/ml, from 0.015 to 0.062 µg/ml, from 0.015 to 0.125 µg/ml, from 0.015 to 0.25 µg/ml, from 0.015 to 0.5 µg/ml, from 0.015 to 1 µg/ml, from 0.015 to 2 µg/ml, from 0.015 to 4 µg/ml, from 0.015 to 8 µg/ml, from 0.015 to 16 µg/ml, for a period of time of 6.5 h, at a temperature of 30° C.; so as to obtain a mixture of cells of said strain ATCC®22019 of *C. parapsilosis* and fluconazole;

b. a step of adding the fluorescent marker Calcofluor White to the mixture of cells of said strain ATCC®22019 of *C. parapsilosis* and fluconazole obtained previously, so as to obtain a mixture of cells of said strain ATCC®22019 of *C. parapsilosis*, labelled by the fluorescent marker Calcofluor White, and fluconazole;

c. a step of quantifying the chitin level, by high-content analysis fluorescence microscopy, of the labelled cells of said strain ATCC®22019 of *C. parapsilosis* in the mixture obtained in the previous step;

d. a step of determining an increase in the chitin level having a value greater than or equal to 20% in the mixture of cells of said strain ATCC®22019 of *C. parapsilosis*, labelled by the fluorescent marker Calcofluor White, and fluconazole as a function of the concentration of micafungin in the population of cells of said strain ATCC®22019 of *C. parapsilosis* compared to the chitin level of a population of cells of said strain ATCC®22019ofe *C. parapsilosis* in the absence of fluconazole; followed by e. a step of counting the cells in the mixture of cells of said strain ATCC®22019 of *C. parapsilosis*, labelled by the fluorescent marker Calcofluor White, and fluconazole; then by f. a step of determining a decrease in the number of cells of at least 0.3 log as a function of the concentration of fluconazole in the population of cells of said strain ATCC®22019 of *C. parapsilosis* compared to the number of cells in a population of cells of said strain ATCC®22019 of *C. parapsilosis* in the absence of fluconazole.

According to an especial embodiment the present invention relates to a method for determining the degree of sensitivity, corresponding to a sensitive phenotype, of a population of cells of the strain ATCC®22019 of *C. parapsilosis* to voriconazole, comprising:

a. a step of contacting cells of said strain ATCC®22019 of *C. parapsilosis* with a gradient of concentrations of voriconazole varying from 0.004 to 5 µg/ml, more especially from 0.004 to 0.009 µg/ml, from 0.004 to 0.019 µg/ml, from 0.004 to 0.039 µg/ml, from 0.004 to 0.078 µg/ml, from 0.004 to 0.156 µg/ml, from 0.004 to 0.312 µg/ml, from 0.004 to 0.0625 µg/ml, from 0.004 to 1.25 µg/ml, from 0.004 to 2.5 µg/ml, from 0.004 to 5 µg/ml, for a period of time of 6.5 h, at a temperature of 30° C.; so as to obtain a mixture of cells of said strain ATCC®22019 of *C. parapsilosis* and voriconazole;

b. a step of adding the fluorescent marker Calcofluor White to the mixture of cells of said strain ATCC®22019 of *C. parapsilosis* and voriconazole obtained previously, so as to obtain a mixture of cells of said strain ATCC®22019 of *C. parapsilosis*, labelled by the fluorescent marker Calcofluor White, and voriconazole;

c. a step of quantifying the chitin level, by high-content analysis fluorescence microscopy, of the labelled cells of said strain ATCC®22019 of ATCC®22019 of *C. parapsilosis* in the mixture obtained in the previous step;

d. a step of determining an increase in the chitin level having a value greater than or equal to 20% in the mixture of cells of said strain ATCC®22019 of ATCC®22019 of *C. parapsilosis*, labelled by the fluorescent marker Calcofluor White, and voriconazole as a function of the concentration of voriconazole in the population of cells of said strain ATCC®22019 of ATCC®22019 of *C. parapsilosis* compared to the chitin level of a population of cells of said strain ATCC®22019 of ATCC®22019 of *C. parapsilosis* in the absence of voriconazole; followed by e. a step of counting the cells in the mixture of cells of said strain ATCC®22019 of *C. parapsilosis*, labelled by the fluorescent marker Calcofluor White, and voriconazole; then by f. a step of determining a decrease in the number of cells of at least 0.3 log as a function of the concentration of voriconazole in the population of cells of said strain ATCC®22019 of *C. parapsilosis* compared to the number of cells in a population of cells of said strain ATCC®22019 of *C. parapsilosis* in the absence of voriconazole.

According to an especial embodiment the present invention relates to a method for determining the degree of sensitivity, corresponding to a sensitive phenotype, of a population of cells of the strain ATCC®2001 of *C. parapsilosis* to micafungin, comprising:

a. a step of contacting cells of said strain ATCC®22019 of *C. parapsilosis* with a gradient of concentrations of micafungin varying from 0.0009 to 1 µg/ml, more especially from 0.0009 to 0.0019 µg/ml, from 0.0009 to 0.0039 µg/ml, from 0.0009 to 0.007 µg/ml, from 0.0009 to 0.015 µg/ml, from 0.0009 to 0.031 µg/ml, from 0.0009 to 0.062 µg/ml, from 0.0009 to 0.125 µg/ml, from 0.0009 to 0.25 µg/ml, from 0.0009 to 0.5 µg/ml, from 0.0009 to 1 µg/ml, for a period of time of 6.5 h, at a temperature of 30° C.; so as to obtain a mixture of cells of said strain ATCC®22019 of *C. parapsilosis* and micafungin;

b. a step of adding the fluorescent marker Calcofluor White to the mixture of cells of said strain ATCC®22019 of *C. parapsilosis* and micafungin obtained previously, so as to obtain a mixture of cells of said strain ATCC®22019 of *C. parapsilosis*, labelled by the fluorescent marker Calcofluor White, and micafungin;

c. a step of quantifying the chitin level, by high-content analysis fluorescence microscopy, of the labelled cells of said strain ATCC®22019 of *C. parapsilosis* in the mixture obtained in the previous step;

d. a step of determining an increase in the chitin level having a value greater than or equal to 20% in the mixture of cells of said strain ATCC®22019 of *C. parapsilosis*, labelled by the fluorescent marker Calcofluor White, and micafungin as a function of the concentration of micafungin in the population of cells of said strain ATCC®22019 of *C. parapsilosis* compared to the chitin level of a population of cells of said strain ATCC®22019 of *C. parapsilosis* in the absence of micafungin; followed by e. a step of counting the cells in the mixture of cells of said strain ATCC®22019 of *C. parapsilosis*, labelled by the fluorescent marker Calcofluor White, and micafungin; then by f. a step of determining a decrease in the number of cells of at least 0.3 log as a function of the concentration of micafungin in the population of cells of said strain ATCC®22019 of *C. parapsilosis* compared to the number of cells in a population of cells of said strain ATCC®22019 of *C. parapsilosis* in the absence of micafungin.

According to an especial embodiment the present invention relates to a method for determining the degree of sensitivity, corresponding to a resistant phenotype, of a population of cells of the strain 8/21 of *C. parapsilosis* to fluconazole, comprising:

a. a step of contacting cells of said strain 8/21 of *C. parapsilosis* with a gradient of concentrations of fluconazole varying from 0.015 to 16 µg/ml, more especially from 0.015 to 0.031 µg/ml, from 0.015 to 0.062 µg/ml, from 0.015 to 0.125 µg/ml, from 0.015 to 0.25 µg/ml, from 0.015 to 0.5 µg/ml, from 0.015 to 1 µg/ml, from 0.015 to 2 µg/ml, from 0.015 to 4 µg/ml, from 0.015 to 8 µg/ml, from 0.015 to 16 µg/ml, for a period of time of 6.5 h, at a temperature of 30° C.; so as to obtain a mixture of cells of said strain 8/21 of *C. parapsilosis* and fluconazole;

b. a step of adding the fluorescent marker Calcofluor White to the mixture of cells of said strain 8/21 of *C.*

*parapsilosis* and fluconazole obtained previously, so as to obtain a mixture of cells of said strain 8/21 of *C. parapsilosis*, labelled by the fluorescent marker Calcofluor White, and fluconazole;
c. a step of quantifying the chitin level, by high-content analysis fluorescence microscopy, of the labelled cells of said strain 8/21 of *C. parapsilosis* in the mixture obtained in the previous step;
d. a step of determining a lack of any increase in the chitin level or an increase in the chitin level of less than 10% in the mixture of cells of said strain 8/21 of *C. parapsilosis*, labelled by the fluorescent marker Calcofluor White, and fluconazole as a function of the concentration of fluconazole in the population of cells of said strain 8/21 of *C. parapsilosis* compared to the chitin level of a population of cells of said strain 8/21 of *C. parapsilosis* in the absence of fluconazole.

According to an especial embodiment the present invention relates to a method for determining the degree of sensitivity, corresponding to a resistant phenotype, of a population of cells of the strain 8/21 of *C. parapsilosis* to fluconazole, comprising:
a. a step of contacting cells of said strain 8/21 of *C. parapsilosis* with a gradient of concentrations of fluconazole varying from 0.015 to 16 μg/ml, more especially from 0.015 to 0.031 μg/ml, from 0.015 to 0.062 μg/ml, from 0.015 to 0.125 μg/ml, from 0.015 to 0.25 μg/ml, from 0.015 to 0.5 μg/ml, from 0.015 to 1 μg/ml, from 0.015 to 2 μg/ml, from 0.015 to 4 μg/ml, from 0.015 to 8 μg/ml, from 0.015 to 16 μg/ml, for a period of time of 6.5 h, at a temperature of 30° C.; so as to obtain a mixture of cells of said strain 8/21 of *C. parapsilosis* and fluconazole;
b. a step of adding the fluorescent marker Calcofluor White to the mixture of cells of said strain 8/21 of *C. parapsilosis* and fluconazole obtained previously, so as to obtain a mixture of cells of said strain 8/21 of *C. parapsilosis*, labelled by the fluorescent marker Calcofluor White, and fluconazole;
c. a step of quantifying the chitin level, by high-content analysis fluorescence microscopy, of the labelled cells of said strain 8/21 of *C. parapsilosis* in the mixture obtained in the previous step;
d. a step of determining an increase in the chitin level of less than 10%, or a decrease in the chitin level especially of less than 20%, or an unchanged chitin level, in the mixture of cells of said strain 8/21 of *C. parapsilosis*, labelled by the fluorescent marker Calcofluor White, and fluconazole as a function of the concentration of fluconazole in the population of cells of said strain 8/21 of *C. parapsilosis* compared to the chitin level of a population of cells of said strain 8/21 of *C. parapsilosis* in the absence of fluconazole.

According to an especial embodiment the present invention relates to a method for determining the degree of sensitivity, corresponding to a resistant phenotype, of a population of cells of the strain 8/21 of *C. parapsilosis* to voriconazole, comprising:
a. a step of contacting cells of said strain 8/21 of *C. parapsilosis* with a gradient of concentrations of voriconazole varying from 0.004 to 5 μg/ml, more especially from 0.004 to 0.009 μg/ml, from 0.004 to 0.019 μg/ml, from 0.004 to 0.039 μg/ml, from 0.004 to 0.078 μg/ml, from 0.004 to 0.156 μg/ml, from 0.004 to 0.312 μg/ml, from 0.004 to 0.0625 μg/ml, from 0.004 to 1.25 μg/ml, from 0.004 to 2.5 μg/ml, from 0.004 to 5 μg/ml, for a period of time of 6.5 h, at a temperature of 30° C.; so as to obtain a mixture of cells of said strain 8/21 of *C. parapsilosis* and voriconazole;
b. a step of adding the fluorescent marker Calcofluor White to the mixture of cells of said strain of fungus and voriconazole obtained previously, so as to obtain a mixture of cells of said strain 8/21 of *C. parapsilosis*, labelled by the fluorescent marker Calcofluor White, and voriconazole;
c. a step of quantifying the chitin level, by high-content analysis fluorescence microscopy, of the labelled cells of said strain 8/21 of *C. parapsilosis* in the mixture obtained in the previous step;
d. a step of determining a lack of any increase in the chitin level or an increase in the chitin level of less than 10% in the mixture of cells of said strain 8/21 of *C. parapsilosis*, labelled by the fluorescent marker Calcofluor White, and voriconazole as a function of the concentration of voriconazole in the population of cells of said strain 8/21 of *C. parapsilosis* compared to the chitin level of a population of cells of said strain 8/21 of *C. parapsilosis* in the absence of voriconazole.

According to an especial embodiment the present invention relates to a method for determining the degree of sensitivity, corresponding to a resistant phenotype, of a population of cells of the strain 8/21 of *C. parapsilosis* to voriconazole, comprising:
a. a step of contacting cells of said strain 8/21 of *C. parapsilosis* with a gradient of concentrations of voriconazole varying from 0.004 to 5 μg/ml, more especially from 0.004 to 0.009 μg/ml, from 0.004 to 0.019 μg/ml, from 0.004 to 0.039 μg/ml, from 0.004 to 0.078 μg/ml, from 0.004 to 0.156 μg/ml, from 0.004 to 0.312 μg/ml, from 0.004 to 0.0625 μg/ml, from 0.004 to 1.25 μg/ml, from 0.004 to 2.5 μg/ml, from 0.004 to 5 μg/ml, for a period of time of 6.5 h, at a temperature of 30° C.; so as to obtain a mixture of cells of said strain 8/21 of *C. parapsilosis* and voriconazole;
b. a step of adding the fluorescent marker Calcofluor White to the mixture of cells of said strain of fungus and voriconazole obtained previously, so as to obtain a mixture of cells of said strain 8/21 of *C. parapsilosis*, labelled by the fluorescent marker Calcofluor White, and voriconazole;
c. a step of quantifying the chitin level, by high-content analysis fluorescence microscopy, of the labelled cells of said strain 8/21 of *C. parapsilosis* in the mixture obtained in the previous step;
d. a step of determining an increase in the chitin level of less than 10%, or a decrease in the chitin level especially of less than 20%, or an unchanged chitin level, in the mixture of cells of said strain 8/21 of *C. parapsilosis*, labelled by the fluorescent marker Calcofluor White, and voriconazole as a function of the concentration of voriconazole in the population of cells of said strain 8/21 of *C. parapsilosis* compared to the chitin level of a population of cells of said strain 8/21 of *C. parapsilosis* in the absence of voriconazole.

According to an especial embodiment the present invention relates to a method for determining the degree of sensitivity, corresponding to a resistant phenotype, of a population of cells of the strain ATCC®6258 of *C. krusei* to fluconazole, comprising:
a. a step of contacting cells of said strain ATCC®6258 of *C. krusei* with a gradient of concentrations of fluconazole varying from 0.125 to 128 μg/ml, more especially from 0.125 to 0.250 μg/ml, from 0.125 to 0.5 μg/ml, from 0.125 to 1 μg/ml, from 0.125 to 2 μg/ml, from 0.125 to 4 µg/ml, from 0.125 to 8 µg/ml, from 0.125 to 16 µg/ml, from 0.125 to 32 µg/ml, from 0.125 to 64 µg/ml, from 0.125 to 128 µg/ml, for a period of time of 6.5 h, at a temperature of 30° C.; so as to obtain a mixture of cells of said strain ATCC®6258 of *C. krusei* and fluconazole;

b. a step of adding the fluorescent marker Calcofluor White to the mixture of cells of said strain ATCC®6258 of *C. krusei* and fluconazole obtained previously, so as to obtain a mixture of cells of said strain ATCC®6258 of *C. krusei*, labelled by the fluorescent marker Calcofluor White, and fluconazole;

c. a step of quantifying the chitin level, by high-content analysis fluorescence microscopy, of the labelled cells of said strain ATCC®6258 of *C. krusei* in the mixture obtained in the previous step;

d. a step of determining a lack of any increase in the chitin level or an increase in the chitin level of less than 10% in the mixture of cells of said strain ATCC®6258 of *C. krusei*, labelled by the fluorescent marker Calcofluor White, and fluconazole as a function of the concentration of fluconazole in the population of cells of said strain ATCC®6258 of *C. krusei* compared to the chitin level of a population of cells of said strain ATCC®6258 of *C. krusei* in the absence of fluconazole.

According to an especial embodiment the present invention relates to a method for determining the degree of sensitivity, corresponding to a resistant phenotype, of a population of cells of the strain ATCC®6258 of *C. krusei* to fluconazole, comprising:

a. a step of contacting cells of said strain ATCC®6258 of *C. krusei* with a gradient of concentrations of fluconazole varying from 0.125 to 128 µg/ml, more especially from 0.125 to 0.250 µg/ml, from 0.125 to 0.5 µg/ml, from 0.125 to 1 µg/ml, from 0.125 to 2 µg/ml, from 0.125 to 4 µg/ml, from 0.125 to 8 µg/ml, from 0.125 to 16 µg/ml, from 0.125 to 32 µg/ml, from 0.125 to 64 µg/ml, from 0.125 to 128 µg/ml, for a period of time of 6.5 h, at a temperature of 30° C.; so as to obtain a mixture of cells of said strain ATCC®6258 of *C. krusei* and fluconazole;

b. a step of adding the fluorescent marker Calcofluor White to the mixture of cells of said strain ATCC®6258 of *C. krusei* and fluconazole obtained previously, so as to obtain a mixture of cells of said strain ATCC®6258 of *C. krusei*, labelled by the fluorescent marker Calcofluor White, and fluconazole;

c. a step of quantifying the chitin level, by high-content analysis fluorescence microscopy, of the labelled cells of said strain ATCC®6258 of *C. krusei* in the mixture obtained in the previous step;

d. a step of determining an increase in the chitin level of less than 10%, or a decrease in the chitin level especially of less than 20%, or an unchanged chitin level, in the mixture of cells of said strain ATCC®6258 of *C. krusei*, labelled by the fluorescent marker Calcofluor White, and fluconazole as a function of the concentration of fluconazole in the population of cells of said strain ATCC®6258 of *C. krusei* compared to the chitin level of a population of cells of said strain ATCC®6258 of *C. krusei* in the absence of fluconazole.

According to an especial embodiment the present invention relates to a method for determining the degree of sensitivity, corresponding to an intermediate phenotype, of a population of cells of the strain ATCC®6258 of *C. krusei* to voriconazole, comprising:

a. a step of contacting cells of said strain ATCC®6258 of *C. krusei* with a gradient of concentrations of voriconazole varying from 0.007 to 8 µg/ml, more especially from 0.007 to 0.015 µg/ml, from 0.007 to 0.031 µg/ml, from 0.007 to 0.062 µg/ml, from 0.007 to 0.125 µg/ml, from 0.007 to 0.25 µg/ml, from 0.007 to 0.5 µg/ml, from 0.007 to 1 µg/ml, from 0.007 to 2 µg/ml, from 0.007 to 4 µg/ml, from 0.007 to 8 µg/ml, for a period of time of 6.5 h, at a temperature of 30° C.; so as to obtain a mixture of cells of said strain ATCC®6258 of *C. krusei* and voriconazole;

b. a step of adding the fluorescent marker Calcofluor White to the mixture of cells of said strain ATCC®6258 of *C. krusei* and voriconazole obtained previously, so as to obtain a mixture of cells of said strain ATCC®6258 of *C. krusei*, labelled by the fluorescent marker Calcofluor White, and voriconazole;

c. a step of quantifying the chitin level, by high-content analysis fluorescence microscopy, of the labelled cells of said strain ATCC®6258 of *C. krusei* in the mixture obtained in the previous step;

d. a step of determining an increase in the chitin level of from 10% to a value less than 20% in the mixture of cells of said strain ATCC®6258 of *C. krusei*, labelled by the fluorescent marker Calcofluor White, and voriconazole as a function of the concentration of voriconazole in the population of cells of said strain ATCC®6258 of *C. krusei* compared to the chitin level of a population of cells of said strain ATCC®6258 of *C. krusei* in the absence of voriconazole; or e. a step of determining an increase in the chitin level greater than or equal to 20% in the mixture of cells of said strain ATCC®6258 of *C. krusei*, labelled by the fluorescent marker Calcofluor White, and voriconazole as a function of the concentration of voriconazole in the population of cells of said strain ATCC®6258 of *C. krusei* compared to the chitin level of a population of cells of said strain ATCC®6258 of *C. krusei* in the absence of voriconazole; or f. a step of counting the cells in the mixture of cells of said strain ATCC®6258 of *C. krusei*, labelled by the fluorescent marker Calcofluor White, and voriconazole after said step of quantifying the chitin level; then by g. a step of determining a decrease in the number of cells of less than 0.3 log, or an unchanged number of cells as a function of the concentration of voriconazole in the population of cells of said strain ATCC®6258 of *C. krusei* compared to the number of cells in a population of cells of said strain ATCC®6258 of *C. krusei* in the absence of voriconazole.

According to an especial embodiment the present invention relates to a method for determining the degree of sensitivity, corresponding to a sensitive phenotype, of a population of cells of the strain ATCC®6258 of *C. krusei* to micafungin, comprising:

a. a step of contacting cells of said strain ATCC®6258 of *C. krusei* with a gradient of concentrations of micafungin varying from 0.0009 to 1 µg/ml, more especially from 0.0009 to 0.0019 µg/ml, from 0.0009 to 0.0039 µg/ml, from 0.0009 to 0.007 µg/ml, from 0.0009 to 0.015 µg/ml, from 0.0009 to 0.031 µg/ml, from 0.0009 to 0.062 µg/ml, from 0.0009 to 0.125 µg/ml, from 0.0009 to 0.25 µg/ml, from 0.0009 to 0.5 µg/ml, from 0.0009 to 1 µg/ml, for a period of time of 6.5 h, at a temperature of 30° C.; so as to obtain a mixture of cells of said strain ATCC®6258 of *C. krusei* and micafungin;

b. a step of adding the fluorescent marker Calcofluor White to the mixture of cells of said strain ATCC®6258 of *C. krusei* and micafungin obtained previously, so as to obtain a mixture of cells of said strain ATCC®6258 of *C. krusei*, labelled by the fluorescent marker Calcofluor White, and micafungin;

c. a step of quantifying the chitin level, by high-content analysis fluorescence microscopy, of the labelled cells of said strain ATCC®6258 of *C. krusei* in the mixture obtained in the previous step;

d. a step of determining an increase in the chitin level having a value greater than or equal to 20% in the mixture of cells of said strain ATCC®6258 of *C. krusei*, labelled by the fluorescent marker Calcofluor White, and micafungin as a function of the concentration of micafungin in the population of cells of said strain ATCC®6258 of *C. krusei* compared to the chitin level of a population of cells of said strain ATCC®6258 of *C. krusei* in the absence of micafungin; followed by e. a step of counting the cells in the mixture of cells of said strain ATCC®6258 of *C. krusei*, labelled by the fluorescent marker Calcofluor White, and micafungin; then by f. a step of determining a decrease in the number of cells of at least 0.3 log as a function of the concentration of micafungin in the population of cells of said strain ATCC®6258 of *C. krusei* compared to the number of cells in a population of cells of said strain ATCC®6258 of *C. krusei* in the absence of micafungin.

According to an especial embodiment the present invention relates to a method for determining the degree of sensitivity, corresponding to a resistant phenotype, of a population of cells of the strain GRE32 of *C. krusei* to fluconazole, comprising:

a. a step of contacting cells of said strain GRE32 of *C. krusei* with a gradient of concentrations of fluconazole varying from 0.125 to 128 µg/ml, more especially from 0.125 to 0.250 µg/ml, from 0.125 to 0.5 µg/ml, from 0.125 to 1 µg/ml, from 0.125 to 2 µg/ml, from 0.125 to 4 µg/ml, from 0.125 to 8 µg/ml, from 0.125 to 16 µg/ml, from 0.125 to 32 µg/ml, from 0.125 to 64 µg/ml, from 0.125 to 128 µg/ml, for a period of time of 6.5 h, at a temperature of 30° C.; so as to obtain a mixture of cells of said strain GRE32 of *C. krusei* and fluconazole;

b. a step of adding the fluorescent marker Calcofluor White to the mixture of cells of said strain GRE32 of *C. krusei* and fluconazole obtained previously, so as to obtain a mixture of cells of said strain GRE32 of *C. krusei*, labelled by the fluorescent marker Calcofluor White, and fluconazole;

c. a step of quantifying the chitin level, by high-content analysis fluorescence microscopy, of the labelled cells of said strain GRE32 of *C. krusei* in the mixture obtained in the previous step;

d. a step of determining a lack of any increase in the chitin level or an increase in the chitin level of less than 10% in the mixture of cells of said strain GRE32 of *C. krusei*, labelled by the fluorescent marker Calcofluor White, and fluconazole as a function of the concentration of fluconazole in the population of cells of said strain GRE32 of *C. krusei* compared to the chitin level of a population of cells of said strain GRE32 of *C. krusei* in the absence of fluconazole.

According to an especial embodiment the present invention relates to a method for determining the degree of sensitivity, corresponding to a resistant phenotype, of a population of cells of the strain GRE32 of *C. krusei* to fluconazole, comprising:

a. a step of contacting cells of said strain GRE32 of *C. krusei* with a gradient of concentrations of fluconazole varying from 0.125 to 128 µg/ml, more especially from 0.125 to 0.250 µg/ml, from 0.125 to 0.5 µg/ml, from 0.125 to 1 µg/ml, from 0.125 to 2 µg/ml, from 0.125 to 4 µg/ml, from 0.125 to 8 µg/ml, from 0.125 to 16 µg/ml, from 0.125 to 32 µg/ml, from 0.125 to 64 µg/ml, from 0.125 to 128 µg/ml, for a period of time of 6.5 h, at a temperature of 30° C.; so as to obtain a mixture of cells of said strain GRE32 of *C. krusei* and fluconazole;

b. a step of adding the fluorescent marker Calcofluor White to the mixture of cells of said strain GRE32 of *C. krusei* and fluconazole obtained previously, so as to obtain a mixture of cells of said strain GRE32 of *C. krusei*, labelled by the fluorescent marker Calcofluor White, and fluconazole;

c. a step of quantifying the chitin level, by high-content analysis fluorescence microscopy, of the labelled cells of said strain GRE32 of *C. krusei* in the mixture obtained in the previous step;

d. a step of determining an increase in the chitin level of less than 10%, or a decrease in the chitin level especially of less than 20%, or an unchanged chitin level, in the mixture of cells of said strain GRE32 of *C. krusei*, labelled by the fluorescent marker Calcofluor White, and fluconazole as a function of the concentration of fluconazole in the population of cells of said strain GRE32 of *C. krusei* compared to the chitin level of a population of cells of said strain GRE32 of *C. krusei* in the absence of fluconazole.

According to an especial embodiment the present invention relates to a method for determining the degree of sensitivity, corresponding to an intermediate phenotype, of a population of cells of the strain GRE32 of *C. krusei* to voriconazole, comprising:

a. a step of contacting cells of said strain GRE32 of *C. krusei* with a gradient of concentrations of voriconazole varying from 0.007 to 8 μg/ml, more especially from 0.007 to 0.015 μg/ml, from 0.007 to 0.031 μg/ml, from 0.007 to 0.062 μg/ml, from 0.007 to 0.125 μg/ml, from 0.007 to 0.25 μg/ml, from 0.007 to 0.5 μg/ml, from 0.007 to 1 μg/ml, from 0.007 to 2 μg/ml, from 0.007 to 4 μg/ml, from 0.007 to 8 μg/ml, for a period of time of 6.5 h, at a temperature of 30° C.; so as to obtain a mixture of cells of said strain GRE32 of *C. krusei* and voriconazole;

b. a step of adding the fluorescent marker Calcofluor White to the mixture of cells of said strain GRE32 of *C. krusei* and voriconazole obtained previously, so as to obtain a mixture of cells of said strain GRE32 of *C. krusei*, labelled by the fluorescent marker Calcofluor White, and voriconazole;

c. a step of quantifying the chitin level, by high-content analysis fluorescence microscopy, of the labelled cells of said strain GRE32 of *C. krusei* in the mixture obtained in the previous step;

d. a step of determining an increase in the chitin level of from 10% to a value less than 20% in the mixture of cells of said strain GRE32 of *C. krusei*, labelled by the fluorescent marker Calcofluor White, and voriconazole as a function of the concentration of voriconazole in the population of cells of said strain GRE32 of *C. krusei* compared to the chitin level of a population of cells of said strain GRE32 of *C. krusei* in the absence of voriconazole; or
e. a step of determining an increase in the chitin level greater than or equal to 20% in the mixture of cells of said strain GRE32 of *C. krusei*, labelled by the fluorescent marker Calcofluor White, and voriconazole as a function of the concentration of voriconazole in the population of cells of said strain GRE32 of *C. krusei* compared to the chitin level of a population of cells of said strain GRE32 of *C. krusei* in the absence of voriconazole; or
f. a step of counting the cells in the mixture of cells of said strain GRE32 of *C. krusei*, labelled by the fluorescent marker Calcofluor White, and voriconazole after said step of quantifying the chitin level; then by
g. a step of determining a decrease in the number of cells of less than 0.3 log, or an unchanged number of cells as a function of the concentration of voriconazole in the population of cells of said strain GRE32 of *C. krusei* compared to the number of cells in a population of cells of said strain GRE32 of *C. krusei* in the absence of voriconazole.

According to an especial embodiment, the present invention relates to a method for determining the degree of sensitivity of a population of cells of a strain of fungus, said fungus being a multicellular fungus of the genus *Aspergillus*, comprising the species *A. fumigatus, A. flavus, A. nidulans, A. terreus, A. versicolor, A. niger*, to an antifungal agent selected from posaconazole, voriconazole, itraconazole, isavuconazole, amphotericin B, and nystatin, comprising:
a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
c. a step of quantifying the chitin level, by high-content analysis fluorescence microscopy, of the labelled cells of said strain of fungus in the mixture obtained in the previous step;
d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;
when said possible change in the chitin level of said step d. is an increase of less than 10% or a decrease especially of less than 20%, or the level is unchanged, it is concluded that said strain has a resistant phenotype;
when said change in the chitin level of said step d. is an increase of from 10% to a value less than 20%, it is concluded that said strain of fungus has an intermediate phenotype;
when said change in the chitin level of said step d. is an increase with a value greater than or equal to 20%, it is concluded that said strain of fungus has a sensitive or intermediate phenotype;

According to an especial embodiment, the present invention relates to a method for determining the degree of sensitivity of a population of cells of a strain of fungus, said fungus being a multicellular fungus of the genus *Aspergillus*, comprising the species *A. fumigatus, A. flavus, A. nidulans, A. terreus, A. versicolor, A. niger*, to an antifungal agent selected from micafungin, anidulafungin and caspofungin, comprising:
a. a step of contacting cells of said strain of fungus with a gradient of concentrations of antifungal agent varying from 0.0017 to 2 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
c. a step of quantifying the chitin level, by high-content analysis fluorescence microscopy, of the labelled cells of said strain of fungus in the mixture obtained in the previous step;
d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;
when said possible change in the chitin level of said step d. is an increase of less than 10% or a decrease especially of less than 20%, or the level is unchanged, it is concluded that said strain of fungus has a resistant phenotype;
when said change in the chitin level of said step d. is an increase of from 10% to a value less than 20%, it is concluded that said strain of fungus has an intermediate phenotype;
when said change in the chitin level of said step d. is an increase with a value greater than or equal to 20%, it is concluded that said strain of fungus has a sensitive or intermediate phenotype;

According to an especial embodiment, the present invention relates to a method for determining the degree of sensitivity of a population of cells of a strain of fungus, said fungus being a multicellular fungus of the genus *Fusarium*, comprising the species *Fusarium solani, Fusarium oxysporum*, to an antifungal agent selected from voriconazole, isavuconazole, amphotericin B, and nystatin, comprising:
a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

when said possible change in the chitin level of said step d. is an increase of less than 10% or a decrease especially of less than 20%, or the level is unchanged, it is concluded that said strain has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment, the present invention relates to a method for determining the degree of sensitivity of a population of cells of a strain of fungus, said fungus being a multicellular fungus of the genus *Scedosporium*, comprising the species *Scedosporium apiospermum, S. prolificans*, to an antifungal agent selected from posaconazole, voriconazole, isavuconazole, and amphotericin B, comprising:
- a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
- b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
- c. a step of quantifying the chitin level, by high-content analysis fluorescence microscopy, of the labelled cells of said strain of fungus in the mixture obtained in the previous step;
- d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

when said possible change in the chitin level of said step d. is an increase of less than 10% or a decrease especially of less than 20%, or the level is unchanged, it is concluded that said strain has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment, the present invention relates to a method for determining the degree of sensitivity of a population of cells of a strain of fungus, said fungus being a multicellular fungus of the genus *Mucor*, comprising the species *Mucor racemosa*, to an antifungal agent selected from posaconazole, voriconazole, isavuconazole, and amphotericin B, comprising:
- a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
- b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
- c. a step of quantifying the chitin level, by high-content analysis fluorescence microscopy, of the labelled cells of said strain of fungus in the mixture obtained in the previous step;
- d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

when said possible change in the chitin level of said step d. is an increase of less than 10% or a decrease especially of less than 20%, or the level is unchanged, it is concluded that said strain has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment, the present invention relates to a method for determining the degree of sensitivity of a population of cells of a strain of fungus, said fungus being a multicellular fungus of the genus *Lichteimia*, comprising the species *Lichteimia corymbifera*, to an antifungal agent selected from posaconazole, voriconazole, isavuconazole, and amphotericin B, comprising:
- a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
- b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
- c. a step of quantifying the chitin level, by high-content analysis fluorescence microscopy, of the labelled cells of said strain of fungus in the mixture obtained in the previous step;
- d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment, the present invention relates to a method for determining the degree of sensitivity of a population of cells of a strain of fungus, said fungus being a multicellular fungus of the genus *Rhizopus*, comprising the species *Rhizopus oryzae*, to an antifungal agent selected from posaconazole, voriconazole, isavuconazole, and amphotericin B, comprising:

a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment, the present invention relates to a method for determining the degree of sensitivity of a population of cells of a strain of fungus, said fungus being a multicellular fungus of the genus *Rhizomucor*, comprising the species *Rhizomucor pusillus*, to an antifungal agent selected from posaconazole, voriconazole, isavuconazole, and amphotericin B, comprising:

a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment, the present invention relates to a method for determining the degree of sensitivity of a population of cells of a strain of fungus, said fungus being a multicellular fungus of the genus *Geotrichum*, to an antifungal agent selected from posaconazole, voriconazole, isavuconazole, and amphotericin B, comprising:

a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment, the present invention relates to a method for determining the degree of sensitivity of a population of cells of a strain of fungus, said fungus being a multicellular fungus of the genus *Paecylomyces*, to an antifungal agent selected from posaconazole, voriconazole, isavuconazole, and amphotericin B, comprising:
   a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
   b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
   c. a step of quantifying the chitin level, by high-content analysis fluorescence microscopy, of the labelled cells of said strain of fungus in the mixture obtained in the previous step;
   d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase with a value greater than or equal to 20%, it is concluded that said strain of fungus has a sensitive or intermediate phenotype;

According to an especial embodiment, the present invention relates to a method for determining the degree of sensitivity of a population of cells of a strain of fungus, said fungus being a multicellular fungus of the genus *Aspergillus*, comprising the species *A. fumigatus, A. flavus, A. nidulans, A. terreus, A. versicolor, A. niger*, to an antifungal agent selected from posaconazole, voriconazole, itraconazole, isavuconazole, amphotericin B, and nystatin, comprising:
   a. a step of contacting cells of said strain of fungus with a gradient of concentrations of antifungal agent varying from 0.007 to 125 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
   b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
   c. a step of quantifying the chitin level, by high-content analysis fluorescence microscopy, of the labelled cells of said strain of fungus in the mixture obtained in the previous step;
   d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by
   e. a step of measuring the length of the vegetative germination hypha in the mixture of cells of said strain of fungus, labelled by Calcofluor White, and antifungal agent; then by
   f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

According to an especial embodiment, the present invention relates to a method for determining the sensitivity or the resistance of a population of cells of a strain of fungus, said fungus being a multicellular fungus of the genus *Aspergillus*, comprising the species *A. fumigatus, A. flavus, A. nidulans, A. terreus, A. versicolor, A. niger*, to an antifungal agent selected from micafungin, anidulafungin and caspofungin, comprising:
   a. a step of contacting cells of said strain of fungus with a gradient of concentrations of antifungal agent varying from 0.0017 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.
   b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by e. a step of measuring the length of the vegetative germination hypha in the mixture of cells of said strain of fungus, labelled by Calcofluor White, and antifungal agent; then by f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

According to an especial embodiment, the present invention relates to a method for determining the sensitivity or resistance of a population of cells of a strain of fungus, said fungus being a multicellular fungus of the genus *Fusarium*, comprising the species *Fusarium solani* and *Fusarium oxysporum*, to an antifungal agent selected from voriconazole, isavuconazole, amphotericin B, and nystatin, comprising:

a. a step of contacting cells of said strain of fungus with a gradient of concentrations of antifungal agent varying from 0.007 to 125 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by e. a step of measuring the length of the vegetative germination hypha in the mixture of cells of said strain of fungus, labelled by Calcofluor White, and antifungal agent; then by f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

According to an especial embodiment, the present invention relates to a method for determining the sensitivity or resistance of a population of cells of a strain of fungus, said fungus being a multicellular fungus of the genus *Scedosporium*, comprising the species *Scedosporium apiospermum, S. prolificans*, to an antifungal agent selected from posaconazole, voriconazole, isavuconazole, and amphotericin B, comprising:

a. a step of contacting cells of said strain of fungus with a gradient of concentrations of antifungal agent varying from 0.007 to 125 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by e. a step of measuring the length of the vegetative germination hypha in the mixture of cells of said strain of fungus, labelled by Calcofluor White, and antifungal agent; then by f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

According to an especial embodiment, the present invention relates to a method for determining the sensitivity or resistance of a population of cells of a strain of fungus, said fungus being a multicellular fungus of the genus *Mucor*, comprising the species *Mucor racemosa*, to an antifungal agent selected from posaconazole, voriconazole, isavuconazole, and amphotericin B, comprising:

a. a step of contacting cells of said strain of fungus with a gradient of concentrations of antifungal agent varying from 0.007 to 125 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

According to an especial embodiment, the present invention relates to a method for determining the sensitivity or resistance of a population of cells of a strain of fungus, said fungus being a multicellular fungus of the genus *Lichteimia*, comprising the species *Lichteimia corymbifera*, to an antifungal agent selected from posaconazole, voriconazole, isavuconazole, and amphotericin B, comprising:

a. a step of contacting cells of said strain of fungus with a gradient of concentrations of antifungal agent varying from 0.007 to 125 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
c. a step of quantifying the chitin level, by high-content analysis fluorescence microscopy, of the labelled cells of said strain of fungus in the mixture obtained in the previous step;
d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by e. a step of measuring the length of the vegetative germination hypha in the mixture of cells of said strain of fungus, labelled by Calcofluor White, and antifungal agent; then by
f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

According to an especial embodiment, the present invention relates to a method for determining the sensitivity or resistance of a population of cells of a strain of fungus, said fungus being a multicellular fungus of the genus *Rhizopus*, comprising the species *Rhizopus oryzae*, to an antifungal agent selected from posaconazole, voriconazole, isavuconazole, and amphotericin B, comprising:

a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
c. a step of quantifying the chitin level, by high-content analysis fluorescence microscopy, of the labelled cells of said strain of fungus in the mixture obtained in the previous step;
d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by e. a step of measuring the length of the vegetative germination hypha in the mixture of cells of said strain of fungus, labelled by Calcofluor White, and antifungal agent; then by
f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

According to an especial embodiment, the present invention relates to a method for determining the sensitivity or resistance of a population of cells of a strain of fungus, said fungus being a multicellular fungus of the genus *Rhizomucor*, comprising the species *Rhizomucor pusillus*, to an antifungal agent selected from posaconazole, voriconazole, isavuconazole, and amphotericin B, comprising:

a. a step of contacting cells of said strain of fungus with a gradient of concentrations of antifungal agent varying from 0.007 to 125 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by e. a step of measuring the length of the vegetative germination hypha in the mixture of cells of said strain of fungus, labelled by Calcofluor White, and antifungal agent; then by f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

According to an especial embodiment, the present invention relates to a method for determining the sensitivity or resistance of a population of cells of a strain of fungus, said fungus being a multicellular fungus of the genus *Geotrichum*, to an antifungal agent selected from posaconazole, voriconazole, isavuconazole, and amphotericin B, comprising:

a. a step of contacting cells of said strain of fungus with a gradient of concentrations of antifungal agent varying from 0.007 to 125 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by e. a step of measuring the length of the vegetative germination hypha in the mixture of cells of said strain of fungus, labelled by Calcofluor White, and antifungal agent; then by f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

According to an especial embodiment, the present invention relates to a method for determining the sensitivity or resistance of a population of cells of a strain of fungus, said fungus being a multicellular fungus of the genus *Paecylomyces*, to an antifungal agent selected from posaconazole, voriconazole, isavuconazole, and amphotericin B, comprising:

a. a step of contacting cells of said strain of fungus with a gradient of concentrations of antifungal agent varying from 0.007 to 8 µg/ml, for a period of time less than or equal to 48 h, especially for a period of time of from 6.5 h to 24 h, at a temperature of from 30 to 35° C., so as to obtain a mixture of cells of said strain of fungus and antifungal agent.

b. a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;

c. a step of quantifying the chitin level, by high-content analysis fluorescence microscopy, of the labelled cells of said strain of fungus in the mixture obtained in the previous step;

d. a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent;

and in the case in which said possible change in the chitin level is an increase in the chitin level greater than or equal to 20%, said step d is followed by e. a step of measuring the length of the vegetative germination hypha in the mixture of cells of said strain of fungus, labelled by Calcofluor White, and antifungal agent; then by f. a step of determining the possible change in the length of the vegetative germination hypha as a function of the concentration of antifungal agent in the population of cells of said strain of fungus compared to the length of vegetative germination hypha of a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

According to an especial embodiment, the present invention relates to a method for determining the degree of sensitivity of a population of cells of a strain of multicellular fungus to an antifungal agent selected from fluconazole, posaconazole, voriconazole, itraconazole, isavuconazole, amphotericin B, and nystatin, comprising:

a. a step of contacting cells of said strain with a gradient of concentrations of antifungal agent varying from 0.007 to 8 µg/ml, more especially from 0.007 to 0.015 µg/ml, from 0.007 to 0.031 µg/ml, from 0.007 to 0.062 µg/ml, from 0.007 to 0.125 µg/ml, from 0.007 to 0.25 µg/ml, from 0.007 to 0.5 µg/ml, from 0.007 to 1 µg/ml, from 0.007 to 2 µg/ml, from 0.007 to 4 µg/ml, from 0.007 to 8 µg/ml, for a period of time of 6.5 h, at a temperature of 30° C.; so as to obtain a mixture of cells of said strain and antifungal agent;

b. a step of adding the fluorescent marker Calcofluor White to the mixture of cells of said strain and said antifungal agent obtained previously, so as to obtain a mixture of cells of said strain, labelled by the fluorescent marker Calcofluor White, and said antifungal agent;

c. a step of quantifying the chitin level, by high-content analysis fluorescence microscopy, of the labelled cells of said strain in the mixture obtained in the previous step;

d. a step of determining the possible change in the chitin level in the mixture of cells of said strain, labelled by the fluorescent marker Calcofluor White, and micafungin as a function of the concentration of antifungal agent in the population of cells of said strain compared to the chitin level of a population of cells of said strain of fungus in the absence of antifungal agent; followed by e. a step of determining the length of the germinative hypha of in the mixture of cells of said strain, labelled by the fluorescent marker Calcofluor White, and antifungal agent; then by f. a step of determining the possible change in the length of the germinative hypha as a function of the concentration of antifungal agent in the population of cells of said strain compared to the length of germinative hypha in a population of cells of said strain of fungus in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

According to an especial embodiment, the present invention relates to a method for determining the degree of sensitivity of a population of cells of a strain of multicellular fungus to an antifungal agent selected from micafungin, anidulafungin, and caspofungin, comprising:

a. a step of contacting cells of said strain with a gradient of concentrations of antifungal agent varying from 0.0017 to 2 µg/ml, more especially from 0.0017 to 0.003 µg/ml, from 0.0017 to 0.007 µg/ml, from 0.0017 to 0.015 µg/ml, from 0.0017 to 0.031 µg/ml, from 0.0017 to 0.062 µg/ml, from 0.0017 to 0.125 µg/ml, from 0.0017 to 0.25 µg/ml, from 0.0017 to 0.5 µg/ml, from 0.0017 to 1 µg/ml, from 0.0017 to 2 µg/ml, for a period of time of 6.5 h, at a temperature of 30° C.; so as to obtain a mixture of cells of said strain and antifungal agent;

b. a step of adding the fluorescent marker Calcofluor White to the mixture of cells of said strain and said antifungal agent obtained previously, so as to obtain a mixture of cells of said strain, labelled by the fluorescent marker Calcofluor White, and said antifungal agent;

c. a step of quantifying the chitin level, by high-content analysis fluorescence microscopy, of the labelled cells of said strain in the mixture obtained in the previous step;

d. a step of determining the change in the chitin level in the mixture of cells of said strain, labelled by the fluorescent marker Calcofluor White, and micafungin as a function of the concentration of antifungal agent in the population of cells of said strain compared to the chitin level of a population of cells of said strain in the absence of antifungal agent; followed by e. a step of determining the length of the germinative hypha of in the mixture of cells of said strain, labelled by the fluorescent marker Calcofluor White, and antifungal agent; then by f. a step of determining the change in the length of the germinative hypha as a function of the concentration of antifungal agent in the population of cells of said strain compared to the length of germinative hypha in a population of cells of said strain in the absence of antifungal agent;

when said possible change in the chitin level of said step d. is an increase of less than 10% or a decrease especially of less than 20%, or the level is unchanged, it is concluded that said strain of fungus has a resistant phenotype;

when said change in the chitin level of said step d. is an increase of from 10% to a value less than 20%, it is concluded that said strain of fungus has an intermediate phenotype;

when said change in the chitin level of said step d. is an increase by a value greater than or equal to 20%, and when said possible change in the length of the vegetative germination hypha of said step f. is a decrease of less than 10% of the length of said hypha or an unchanged length of the germinative hyphae, it is concluded that the strain has an intermediate phenotype;

when said change in the chitin level of said step d. is an increase by a value greater than or equal to 20%, and when said possible change in the length of the vegetative germination hypha of said step f is a decrease of at least 10% of the length of said hypha, the strain has a sensitive phenotype.

FIGURES

FIG. 1: Shows the effect of fluconazole on cells of the strain SC5314 of *C. albicans*. The solid curve shows the change in the chitin level in the wall of the cells as a function of the concentration of fluconazole (logarithmic scale). The dashed curve shows the change in the number of cells in the medium as a function of the concentration of fluconazole (logarithmic scale).

FIG. 2: Shows the effect of voriconazole on cells of the strain SC5314 of *C. albicans*. The solid curve shows the change in the chitin level in the wall of the cells as a function of the concentration of voriconazole (logarithmic scale). The dashed curve shows the change in the number of cells in the medium as a function of the concentration of voriconazole (logarithmic scale).

FIG. 3: Shows the effect of fluconazole on cells of the strain DSY296 of *C. albicans*. The solid curve shows the change in the chitin level in the wall of the cells as a function of the concentration of fluconazole (logarithmic scale). The dashed curve shows the change in the number of cells in the medium as a function of the concentration of fluconazole (logarithmic scale).

FIG. 4: Shows the effect of voriconazole on cells of the strain DSY296 of *C. albicans*. The solid curve shows the change in the chitin level in the wall of the cells as a function of the concentration of voriconazole (logarithmic scale). The dashed curve shows the change in the number of cells in the medium as a function of the concentration of voriconazole (logarithmic scale).

FIG. 5: Shows the effect of micafungin on cells of the strain TOP of *C. albicans*. The solid curve shows the change in the chitin level in the wall of the cells as a function of the concentration of micafungin (logarithmic scale). The dashed curve shows the change in the number of cells in the medium as a function of the concentration of micafungin (logarithmic scale).

FIG. 6: Shows the effect of fluconazole on cells of the strain Tg5 of *C. glabrata*. The solid curve shows the change in the chitin level in the wall of the cells as a function of the concentration of fluconazole (logarithmic scale). The dashed curve shows the change in the number of cells in the medium as a function of the concentration of fluconazole (logarithmic scale).

FIG. 7: Shows the effect of voriconazole on cells of the strain Tg5 of *C. glabrata*. The solid curve shows the change in the chitin level in the wall of the cells as a function of the concentration of voriconazole (logarithmic scale). The dashed curve shows the change in the number of cells in the medium as a function of the concentration of voriconazole (logarithmic scale).

FIG. 8: Shows the effect of fluconazole on cells of the strain ATCC®7349 of *C. tropicalis*. The solid curve shows the change in the chitin level in the wall of the cells as a function of the concentration of fluconazole (logarithmic scale). The dashed curve shows the change in the number of cells in the medium as a function of the concentration of fluconazole (logarithmic scale).

FIG. 9: Shows the effect of voriconazole on cells of the strain ATCC®7349 of *C. tropicalis*. The solid curve shows the change in the chitin level in the wall of the cells as a function of the concentration of voriconazole (logarithmic scale). The dashed curve shows the change in the number of cells in the medium as a function of the concentration of voriconazole (logarithmic scale).

FIG. 10: Shows the effect of micafungin on cells of the strain ATCC®7349 of *C. tropicalis*. The solid curve shows the change in the chitin level in the wall of the cells as a function of the concentration of micafungin (logarithmic scale). The dashed curve shows the change in the number of cells in the medium as a function of the concentration of micafungin (logarithmic scale).

FIG. 11: Shows the effect of micafungin on cells of the strain 13/5 of *C. tropicalis*. The solid curve shows the change in the chitin level in the wall of the cells as a function of the concentration of micafungin (logarithmic scale). The dashed curve shows the change in the number of cells in the medium as a function of the concentration of micafungin (logarithmic scale).

FIG. 12: Shows the effect of fluconazole on cells of the strain ATCC®22019 of *C. parapsilosis*. The solid curve shows the change in the chitin level in the wall of the cells as a function of the concentration of fluconazole (logarithmic scale). The dashed curve shows the change in the number of cells in the medium as a function of the concentration of fluconazole (logarithmic scale).

FIG. 13: Shows the effect of voriconazole on cells of the strain ATCC®22019 of *C. parapsilosis*. The solid curve shows the change in the chitin level in the wall of the cells as a function of the concentration of voriconazole (logarithmic scale). The dashed curve shows the change in the number of cells in the medium as a function of the concentration of voriconazole (logarithmic scale).

FIG. 14: Shows the effect of micafungin on cells of the strain ATCC®22019 of *C. parapsilosis*. The solid curve shows the change in the chitin level in the wall of the cells as a function of the concentration of micafungin (logarithmic scale). The dashed curve shows the change in the number of cells in the medium as a function of the concentration of micafungin (logarithmic scale).

FIG. 15: Shows the effect of fluconazole on cells of the strain 8/21 of *C. parapsilosis*. The solid curve shows the change in the chitin level in the wall of the cells as a function of the concentration of fluconazole (logarithmic scale). The dashed curve shows the change in the number of cells in the medium as a function of the concentration of fluconazole (logarithmic scale).

FIG. 16: Shows the effect of voriconazole on cells of the strain 8/21 of *C. parapsilosis*. The solid curve shows the change in the chitin level in the wall of the cells as a function of the concentration of voriconazole (logarithmic scale). The dashed curve shows the change in the number of cells in the medium as a function of the concentration of voriconazole (logarithmic scale).

FIG. 17: Shows the effect of fluconazole on cells of the strain Tg5 of ATCC®6258 of *C. krusei*. The solid curve shows the change in the chitin level in the wall of the cells as a function of the concentration of fluconazole (logarithmic scale). The dashed curve shows the change in the number of cells in the medium as a function of the concentration of fluconazole (logarithmic scale).

FIG. 18: Shows the effect of voriconazole on cells of the strain Tg5 of ATCC®6258 of *C. krusei*. The solid curve shows the change in the chitin level in the wall of the cells as a function of the concentration of voriconazole (logarithmic scale). The dashed curve shows the change in the number of cells in the medium as a function of the concentration of voriconazole (logarithmic scale).

FIG. 19: Shows the effect of fluconazole on cells of the strain GRE32 of *C. krusei*. The solid curve shows the change in the chitin level in the wall of the cells as a function of the concentration of fluconazole (logarithmic scale). The dashed curve shows the change in the number of cells in the medium as a function of the concentration of fluconazole (logarithmic scale).

FIG. 20: Shows the effect of voriconazole on cells of the strain GRE32 of *C. krusei*. The solid curve shows the change in the chitin level in the wall of the cells as a function of the concentration of voriconazole (logarithmic scale). The dashed curve shows the change in the number of cells in the medium as a function of the concentration of voriconazole (logarithmic scale).

EXAMPLES

A—Examples of Unicellular Fungi

I—Culture of Fungus in the Presence of an Antifungal Agent

The strains of *Candida* were incubated beforehand at 30° C. overnight in a yeast extract medium—peptone dextrose (YPD) (1% bacto peptone, 0.5% yeast extract, 2% glucose, 1.5% agar).

Yeast colonies were then removed from YPD medium plates and suspended in a 0.9% NaCl saline solution, in which the cell concentration was estimated by optical microscopy using Kova counting slides.

A dilution was performed to obtain 15 ml of an inoculum at $3 \times 10^6$ CFU/ml, in a synthetic complete (SC) medium at pH 7 (2% glucose, 0.5% ammonium sulfate, 0.17% nitrogen-containing yeast base, 0.2% synthetic complete mixture, and 10% HEPES 1.5M pH 7.2) for *C. albicans, C. parapsilosis, C. tropicalis* and *C. krusei*, and in a solution of RPMI 1640 pH 7.3 (10% HEPES 1M pH 7.2) for *C. glabrata*, so as to reduce the formation of septa and clusters.

1 ml of inoculum was then added to 2 ml of antifungal solution prepared in an SC or RPMI medium depending on the species of fungus, so as to obtain a final concentration of yeast of $10^6$ CFU/ml and the desired concentration of antifungal agent according to table 1.

TABLE 1

Gradients of concentration of fluconazole, voriconazole and micafungin used for the yeast species *Candida albicans, C. tropicalis, C. parapsilosis, C. glabrata* and *C. krusei*.

| Antifungal agent | Species | Concentration (µg/ml) | | | | | | | | | |
|---|---|---|---|---|---|---|---|---|---|---|---|
| Fluconazole | *C. albicans, C. tropicalis, C. parapsilosis* | 16 | 8 | 4 | 2 | 1 | 0.5 | 0.25 | 0.125 | 0.062 | 0.031 | 0.015 |
| | *C. glabrata, C. krusei* | 128 | 64 | 32 | 16 | 8 | 4 | 2 | 1 | 0.5 | 0.25 | 0.125 |
| Voriconazole | *C. albicans, C. tropicalis, C. parapsilosis* | 5 | 2.5 | 1.25 | 0.625 | 0.312 | 0.156 | 0.078 | 0.039 | 0.019 | 0.009 | 0.004 |
| | *C. glabrata, C. krusei* | 8 | 4 | 2 | 1 | 0.5 | 0.25 | 0.125 | 0.062 | 0.031 | 0.015 | 0.007 |
| Micafungin | *C. albicans, C. glabrata, C. tropicalis, C. parapsilosis, C. krusei* | 1 | 0.5 | 0.25 | 0.125 | 0.062 | 0.031 | 0.015 | 0.007 | 0.004 | 0.002 | 0.001 |

After homogenisation, the cultures were placed at 30° C. at 200 rpm, with the exception of cultures of C. glabrata, which were placed at 35° C. at 200 rpm, and incubated for a period of 6.5 h or 24 h.

II—Examination by High-Content Analysis (HCA) Microscopy

After incubation, 100 µl of the culture of fungi obtained above were transferred in triplicate to 96-well plates, and 2.5 µl of Calcofluor White (CFW) were added to each well so as to mark the chitin of the cell walls of the yeasts.

A step of acquiring images by automated fluorescence microscopy (ScanR screening station, Olympus), using a 40× lens and a CFW filter, made it possible to obtain 30 images per well so as to capture enough cells to provide statistically significant data. These images were analysed by software (ScanR analysis software, Olympus). Firstly, the background noise was processed so as to improve the contrast between the fluorescence of the yeasts and background noise. A pixel threshold was then defined. Segmentation of the fluorescent elements present in each of the acquired images was then performed using an algorithm predefined in the software, making it possible to determine the limit of each element on the basis of the fluorescence intensity of said element. A size parameter was then applied to select the yeasts and eliminate the aggregates and the fluorescent debris.

Each element then corresponding to a yeast, it was thus possible, on the basis of these elements predefined beforehand, to define the fluorescence intensity for each of the yeasts, this intensity being directly correlated with the chitin content of their wall.

On the basis of said defined elements, it was also possible to automatically count the yeasts, This data was then processed by a software (GraphPad Prism) so as to provide a representation in the form of a graph showing the change in the chitin level of the cell wall and the change in the number of cells in CFU/ml (colony-forming unit per ml) as a function of the concentration of antifungal agent, for each strain of yeast-antifungal agent pairing.

When an increase in the chitin level having a value less than 10% or a decrease in the chitin level of less than 20% or an unchanged chitin level are observed compared to the chitin level of a population of cells of said fungus in the absence of antifungal agent, the strain is assumed to have the resistant phenotype.

When an increase in the chitin level having a value of from 10% to a value less than 20% is observed compared to the chitin level of a population of cells of said fungus in the absence of antifungal agent, the strain is assumed to have the intermediate phenotype.

When an increase in the chitin level greater than or equal to 20% is observed compared to the chitin level of a population of cells of said fungus in the absence of antifungal agent, as well as a decrease in the number of cells of less than 0.3 log or an unchanged number of cells compared to the number of cells in a population of cells of said fungus in the absence of antifungal agent, the strain is assumed to have the intermediate phenotype.

When an increase in the chitin level greater than or equal to 20% is observed compared to the chitin level of a population of cells of said fungus in the absence of antifungal agent, as well as a decrease in the number of cells of at least 0.3 log compared to the number of cells in a population of cells of said fungus in the absence of antifungal agent, the strain is assumed to have the sensitive phenotype.

It should be noted that all of the examples of the present application comprise graphs showing both the curve for the change in chitin level and the curve for the change in the number of cells, however the parameter of the change in the number of cells is not used in some cases for determination of the sensitivity of the strain of fungus.

In fact, the generation of the two curves is inherent to the software used for the execution of the present examples.

The consideration of a parameter other than the cell count for determining the sensitivity of a strain of fungus constitutes the uniqueness of this invention compared to existing tests based on a measurement of yeast growth, these being subject to the subjectivity of the reader.

The aim of the present application is thus to find another criterion for determining the sensitivity of a strain of fungus, the cell count being included as supplementary piece of information in the majority of cases. This parameter, however, is necessary to distinguish between an intermediate phenotype and a sensitive phenotype when the change in chitin level is greater than or equal to 20%.

III—Analysis by the Comparative Etest® Method, Marketed by Biomérieux

The Etest® method is a commercial test for determining the sensitivity of a strain, most frequently used routinely in clinical mycology laboratories.

The results obtained by HCA were compared with this obtained with this susceptibility test.

The Etest® tests were performed according to the manufacturer's instructions. After distributing a standardised Mac Farland 0.5 inoculum (equivalent of $10^8$ CFU/ml) over plates of RPMI medium, said plates were incubated for 24 h at 35° C., with the exception of C. glabrata in which case the incubation was extended to 48 h so as to be able to determine the minimum inhibitory concentration (MIC).

The results of the MICs obtained were interpreted in accordance with the tables of the CLSI (Clinical and Laboratory Standards Institute) and/or of EUCAST (European Committee on Antimicrobial Susceptibility Testing) (Arendrup M C, Cuenca-Estrella M, Lass-Flörl C, Hope W W (2014) Breakpoints for antifungal agents: an update from EUCAST focussing on echinocandins against Candida spp and triazoles against Aspergillus spp. Drug Resist Updat 16(6):81-95. doi:10.1016/j.drup.2014.01.001) (cf. Table 2 taken from Maubon D, Garnaud C, Calandra T, et al. (2014) Resistance of Candida spp. to antifungal drugs in the ICU: where are we now? Intensive Care Med. doi: 10.1007/s00134-014-3404-7) which list the clinical thresholds (CBPs) for the most common species of yeast of the genus Candida as a function of different antifungal agents, or according to the table of epidemiological thresholds (ECVs).

The MIC thus makes it possible to determine the sensitivity of a strain to an antifungal agent. The CBPs or clinical thresholds make it possible to interpret this MIC and to predict a failure of therapy in the patient. The CBPs make it possible to establish the following categories: sensitive, intermediate, and resistant.

If the value of the MIC is in the sensitive category, the likelihood of failure of the treatment is low. This likelihood increases in the intermediate and resistant categories.

These tables make it possible to detect the acquired resistances which result primarily from the selection of mutants subjected to the pressure of pharmaceutical products in patients. They are thus specific to strains and should not be confused with intrinsic resistances, which are specific to species.

TABLE 2

Clinical thresholds of the tables of the CLSI (Clinical and Laboratory Standards Institute) and/or of EUCAST (European Committee on Antimicrobial Susceptibility Testing) for species of *Candida* (Source: Maubon D, Garnaud C, Calandra T, et al. (2014) Resistance of *Candida* spp. to antifungal drugs in the ICU: where are we now? Intensive Care Med. doi: 10.1007/s00134-014-3404-7).

| | | MIC (mg/L) minimum inhibitory concentration | | | | | | | | | | | | |
|---|---|---|---|---|---|---|---|---|---|---|---|---|---|---|
| | | *C. albicans* | | *C. glabrata* | | *C. krusei* | | *C. parapsilosis* | | *C. tropicalis* | | *C. guilliermondii* | | Non-species related breakpoints[1] |
| Antifungal agent | | S≤ | R> | S≤ | R> | S≤ | R> | S≤ | R> | S≤ | R> | S≤ | R> | S≤ | R> |
| Amphotericin B | EUCAST | 1 | 1 | 1 | 1 | 1 | 1 | 1 | 1 | 1 | 1 | IE | IE | IE | IE |
| | CLSI | ND | ND | ND | ND | ND | ND | ND | ND | ND | ND | ND | ND | 1 | |
| Fluconazole | EUCAST | 2 | 4 | 0.002 | 32 | — | — | 2 | 4 | 2 | 4 | IE[2] | IE[2] | 2 | 4 |
| | CLSI | 2 | 4 | 0.002 | 32 | — | — | 2 | 4 | 2 | 4 | ND | ND | ND | ND |
| Voriconazole | EUCAST | 0.12[5] | 0.12[5] | IE[2] | IE[2] | IE[2] | IE[2] | 0.12[5] | 0.12[5] | 0.12[5] | 0.12[5] | IE[2] | IE[2] | IE | IE |
| | CLSI | 0.12 | 0.5 | — | — | 0.5 | 1 | 0.12 | 0.5 | 0.12 | 0.5 | ND | ND | ND | ND |
| Posaconazole | EUCAST | 0.06 | 0.06 | IE2 | IE2 | IE2 | IE2 | 0.06 | 0.06 | 0.06 | 0.06 | IE[2] | IE[2] | IE | IE |
| | CLSI | ND | ND | ND | ND | ND | ND | ND | ND | ND | ND | ND | ND | ND | ND |
| Itraconazole | EUCAST | IP | IP | IP | IP | IP | IP | IP | IP | IP | IP | IP | IP | IP | IP |
| | CLSI | ND | ND | ND | ND | ND | ND | ND | ND | ND | ND | ND | ND | 0.125 | 0.5 |
| Anidulafungin | EUCAST | 0.03 | 0.03 | 0.06 | 0.06 | 0.06 | 0.06 | 0.002 | 4 | 0.06 | 0.06 | IE[2] | IE[2] | IE | IE |
| | CLSI | 0.25 | 0.5 | 0.12 | 0.25 | 0.25 | 0.5 | 2 | 4 | 0.25 | 0.5 | 2 | 4 | ND | ND |
| Micafungin | EUCAST | 0.016 | 0.016 | 0.03 | 0.03 | IE[4] | IE[4] | 0.002 | 2 | IE[4] | IE[4] | IE[4] | IE[4] | IE | IE |
| | CLSI | 0.25 | 0.5 | 0.06 | 0.125 | 0.25 | 0.5 | 2 | 4 | 0.25 | 0.5 | 2 | 4 | ND | ND |
| Caspofungin | EUCAST | Note[3] | Note[3] | Note[3] | Note[3] | Note[3] | Note[3] | Note[3] | Note[3] | Note[3] | Note[3] | IE[2] | IE[2] | Note[3] | Note[3] |
| | CLSI | 0.25 | 0.5 | 0.12 | 0.25 | 0.25 | 0.5 | 2 | 4 | 0.25 | 0.5 | 2 | 4 | ND | ND |
| Flucytosine | EUCAST | ND | ND | ND | ND | ND | ND | ND | ND | ND | ND | ND | ND | ND | ND |
| | CLSI | ND | ND | ND | ND | ND | ND | ND | ND | ND | ND | ND | ND | 4 | 16 |

ND: no data, DP: data in preparation, DI: data insufficient.
[1]Thresholds determined primarily on the basis of pharmacokinetic data, independent of species. Should be used only for organisms that have no specific thresholds.
[2]The thresholds for this species are generally higher than for *C. albicans*.
[3]Due to a significant inter-laboratory variation for the MICs of caspofungin, the EUCAST thresholds were established for this agent.
[4]The MICs for *C. tropicalis* are 1 to 2 dilutions higher than for *C. albicans* and *C. glabrata*. In the clinical study, the rate of therapeutic success was slightly lower for *C. tropicalis* than for *C. albicans* at the two doses (100 and 150 mg per day). However, the difference was not significant and the clinical relevance of this difference is unknown. The MICs for *C. krusei* are 3 dilutions higher than for *C. albicans* and, similarly, those of *C. guilliermondii* are 8 dilutions higher. In addition, only a small number of cases involve these species in the clinical tests. The data is insufficient to conclude that the wild population of these species can be considered as sensitive to micafungin.
[5]The strains with MIC values above the S/I threshold are rare, or else not reported at all. The tests for identifying sensitivity performed on these isolates must be repeated, and if the result is confirmed the isolate must be sent to a reference laboratory. Until there is proof of the clinical response for the confirmed isolates with MIC above the current resistant clinical threshold (in italics), these isolates must be marked as resistant.

Example 1: Test of Sensitivity of the Strain SC5314 of *C. albicans* to Fluconazole The strain SC5314 of *C. albicans* was cultivated as described in paragraph I of the Examples section so as to obtain an inoculum at $3 \times 10^6$ CFU/ml in 15 ml of SC medium.

2 ml of fluconazole solution prepared in the SC medium were then added to 1 ml of this inoculum so as to obtain a final concentration of yeast of $10^6$ CFU/ml and of 16 μg/ml in fluconazole.

The inoculum was treated in the same way so as to obtain cultures of $10^6$ CFU/ml and the following concentrations of fluconazole: 0.015 μg/ml, 0.031 μg/ml, 0.062 μg/ml, 0.125 μg/ml, 0.25 μg/ml, 0.5 μg/ml, 1 μg/ml, 2 μg/ml, 4 μg/ml, 8 μg/ml, 16 μg/ml.

A control without fluconazole was prepared by adding 2 ml of SC medium.

After incubation for 6.5 h at 30° C. with stirring at 200 rpm, 100 μl of each culture were removed and transferred to 96-well plates. This procedure was performed in triplicate, and 2.5 μl of CFW were then added to each well.

The chitin level in the cell wall of the yeasts was then measured by high-contact analysis (HCA) microscopy, as described in paragraph II of the Examples section, in triplicate for each condition of concentration of fluconazole and without fluconazole.

The data obtained was then averaged for each different tested condition and was presented in the form of a graph, shown in FIG. 1, where the solid curve shows the change in chitin level as a function of the concentration of fluconazole.

An increase having a value greater than or equal to 20% of the chitin level in the wall of the cells of the strain SC5314 of *C. albicans* in the presence of fluconazole was observed compared to the chitin level of a population of cells of the strain SC5314 of *C. albicans* in the absence of fluconazole.

The number of cells for each triplicate of each condition of concentration of fluconazole and without fluconazole was then determined by high-content analysis (HCA) microscopy, as described in paragraph II of the Examples section.

The data obtained was then averaged for each different tested condition and was presented in the form of a graph, shown in FIG. 1, where the dashed curve shows the change in the number of cells as a function of the concentration of fluconazole.

A decrease of at least 0.3 log of the number of cells of the strain SC5314 of *C. albicans* as a function of the concentration of fluconazole in the medium was observed compared to the number of cells in a population of cells of the strain SC5314 of *C. albicans* in the absence of fluconazole.

These results confirm the sensitive phenotype of the strain SC5314 of *C. albicans* with respect to fluconazole.

This result was confirmed by that obtained with the Etest method. In fact, with this method an MIC of 0.125 μg/ml was obtained, and the interpretation by the EUCAST and CLSI tables made it possible to determine that, with an MIC lower than 2 μg/ml for fluconazole, this strain is sensitive to this antifungal agent.

Example 2: Test of Sensitivity of the Strain SC5314 of *C. albicans* to Voriconazole The strain SC5314 of *C. albicans* was cultivated as described in paragraph I of the Examples section so as to obtain an inoculum at $3 \times 10^6$ CFU/ml in 15 ml of SC medium.

2 ml of voriconazole solution prepared in the SC medium were then added to 1 ml of this inoculum so as to obtain a final concentration of yeast of $10^6$ CFU/ml and of 5 µg/ml in voriconazole.

The inoculum was treated in the same way so as to obtain cultures of $10^6$ CFU/ml and the following concentrations of voriconazole: 0.004 µg/ml, 0.009 µg/ml, 0.019 µg/ml, 0.039 µg/ml, 0.078 µg/ml, 0.156 µg/ml, 0.312 µg/ml, 0.625 µg/ml, 1.25 µg/ml, 2.5 µg/ml, 5 µg/ml.

A control without voriconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of antifungal agent and without antifungal agent.

The data obtained was then averaged for each different tested condition and was presented in the form of a graph, shown in FIG. 2, where the solid curve shows the change in chitin level as a function of the concentration of voriconazole.

An increase having a value greater than or equal to 20% of the chitin level in the wall of the cells of the strain SC5314 of *C. albicans* in the presence of voriconazole was observed compared to the chitin level of a population of cells of the strain SC5314 of *C. albicans* in the absence of voriconazole.

The number of cells for each triplicate of each condition of concentration of voriconazole and without voriconazole was then determined by high-content analysis (HCA) microscopy, as described in paragraph II of the Examples section.

The data obtained was then averaged for each different tested condition and was presented in the form of a graph, shown in FIG. 2, where the dashed curve shows the change in the number of cells as a function of the concentration of voriconazole.

A decrease of at least 0.3 log of the number of cells of the strain SC5314 of *C. albicans* as a function of the concentration of voriconazole in the medium was observed compared to the number of cells in a population of cells of the strain SC5314 of *C. albicans* in the absence of voriconazole.

These results confirm the sensitive phenotype of the strain SC5314 of *C. albicans* with respect to voriconazole.

This result was confirmed by that obtained with the Etest method. In fact, with this method an MIC of 0.012 µg/ml was obtained, and the interpretation by the EUCAST and CLSI tables made it possible to determine that, with an MIC lower than 0.12 µg/ml for voriconazole, this strain is sensitive to this antifungal agent.

Example 3: Test of Sensitivity of the Strain DSY296 of *C. albicans* to Fluconazole The strain DSY296 of *C. albicans* was cultivated as described in paragraph I of the Examples section so as to obtain an inoculum at $3 \times 10^6$ CFU/ml in 15 ml of SC medium.

2 ml of fluconazole solution prepared in the SC medium were then added to 1 ml of this inoculum so as to obtain a final concentration of yeast of $10^6$ CFU/ml and of 16 µg/ml in fluconazole.

The inoculum was treated in the same way so as to obtain cultures of $10^6$ CFU/ml and the following concentrations of fluconazole: 0.015 µg/ml, 0.031 µg/ml, 0.062 µg/ml, 0.125 µg/ml, 0.25 µg/ml, 0.5 µg/ml, 1 µg/ml, 2 µg/ml, 4 µg/ml, 8 µg/ml, 16 µg/ml.

A control without fluconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of fluconazole and without fluconazole.

The data obtained was then averaged for each different tested condition and was presented in the form of a graph, shown in FIG. 3, where the solid curve shows the change in chitin level as a function of the concentration of fluconazole.

A decrease in the chitin level of less than 20% in the wall of the cells of the strain DSY296 of *C. albicans* in the presence of fluconazole was observed compared to the chitin level of cells of the strain DSY296 of *C. albicans* in the absence of fluconazole.

This result confirms the resistant phenotype of the strain DSY296 of *C. albicans* with respect to fluconazole.

This result was confirmed by that obtained with the Etest method. In fact, with this method an MIC of 96 µg/ml was obtained, and the interpretation by the EUCAST and CLSI tables made it possible to determine that, with an MIC greater than 4 µg/ml for fluconazole, this strain is resistant to this antifungal agent.

Example 4: Test of Sensitivity of the Strain DSY296 of *C. albicans* to Voriconazole The strain DSY296 of *C. albicans* was cultivated as described in paragraph I of the Examples section so as to obtain an inoculum at $3 \times 10^6$ CFU/ml in 15 ml of SC medium.

2 ml of voriconazole solution prepared in the SC medium were then added to 1 ml of this inoculum so as to obtain a final concentration of yeast of $10^6$ CFU/ml and of 5 µg/ml in voriconazole.

The inoculum was treated in the same way so as to obtain cultures of $10^6$ CFU/ml and the following concentrations of voriconazole: 0.004 µg/ml, 0.009 µg/ml, 0.019 µg/ml, 0.039 µg/ml, 0.078 µg/ml, 0.156 µg/ml, 0.312 µg/ml, 0.625 µg/ml, 1.25 µg/ml, 2.5 µg/ml, 5 µg/ml.

A control without voriconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of voriconazole and without voriconazole.

The data obtained was then averaged for each different tested condition and was presented in the form of a graph, shown in FIG. 4, where the solid curve shows the change in chitin level as a function of the concentration of voriconazole.

A decrease in the chitin level of less than 20% in the wall of the cells of the strain DSY296 of C. albicans in the presence of voriconazole was observed compared to the chitin level of cells of the strain DSY296 of C. albicans in the absence of voriconazole.

This result confirms the resistant phenotype of the strain DSY296 of C. albicans with respect to voriconazole.

This result was confirmed by that obtained with the Etest method. In fact, with this method an MIC of 1 µg/ml was obtained, and the interpretation by the EUCAST and CLSI tables made it possible to determine that, with an MIC greater than 0.12 µg/ml and greater than 0.5 µg/ml respectively for voriconazole, this strain is resistant to this antifungal agent.

Example 5: Test of Sensitivity of the Strain TOP of C. albicans to Micafungin

The strain TOP of C. albicans was cultivated as described in paragraph I of the Examples section so as to obtain an inoculum at $3 \times 10^6$ CFU/ml in 15 ml of SC medium.

2 ml of micafungin solution prepared in the SC medium were then added to 1 ml of this inoculum so as to obtain a final concentration of yeast of $10^6$ CFU/ml and of 1 µg/ml in micafungin.

The inoculum was treated in the same way so as to obtain cultures of $10^6$ CFU/ml and the following concentrations of fluconazole: 0.0009 µg/ml, 0.0019 µg/ml, 0.039 µg/ml, 0.007 µg/ml, 0.015 µg/ml, 0.031 µg/ml, 0.062 µg/ml, 0.125 µg/ml, 0.25 µg/ml, 0.5 µg/ml, 1 µg/ml.

A control without voriconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of micafungin and without micafungin.

The data obtained was then averaged for each different tested condition and was presented in the form of a graph, shown in FIG. 5, where the solid curve shows the change in chitin level as a function of the concentration of micafungin.

An increase in the chitin level of less than 10% in the wall of the cells of the strain TOP of C. albicans in the presence of micafungin was observed compared to the chitin level of cells of the strain TOP of C. albicans in the absence of micafungin.

This result confirms the resistant phenotype of the strain TOP of C. albicans with respect to micafungin.

This result was confirmed by that obtained with the Etest method. In fact, with this method an MIC of 1 µg/ml was obtained, and the interpretation by the EUCAST and CLSI tables made it possible to determine that, with an MIC greater than 0.016 µg/ml and greater than 0.5 µg/ml respectively for micafungin, this strain is resistant to this antifungal agent.

Example 6: Test of Sensitivity of the Strain Tg5 of C. glabrata to Fluconazole

The strain Tg5 of C. glabrata was cultivated as described in paragraph I of the Examples section so as to obtain an inoculum at $3 \times 10^6$ CFU/ml in 15 ml of RPMI medium.

2 ml of fluconazole solution prepared in the RPMI medium were then added to 1 ml of this inoculum so as to obtain a final concentration of yeast of $10^6$ CFU/ml and of 128 µg/ml in fluconazole.

The inoculum was treated in the same way so as to obtain cultures of $10^6$ CFU/ml and the following concentrations of fluconazole: 0.125 µg/ml, 0.25 µg/ml, 0.5 µg/ml, 1 µg/ml, 2 µg/ml, 4 µg/ml, 8 µg/ml, 16 µg/ml, 32 µg/ml, 64 µg/ml, 128 µg/ml.

A control without fluconazole was prepared by adding 2 ml of RPMI medium.

After incubation for 6.5 h at 35° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of fluconazole and without fluconazole.

The data obtained was then averaged for each different tested condition and was presented in the form of a graph, shown in FIG. 6, where the solid curve shows the change in chitin level as a function of the concentration of fluconazole.

A decrease in the chitin level of less than 20% in the wall of the cells of the strain Tg5 of C. glabrata in the presence of fluconazole was observed compared to the chitin level of cells of the strain Tg5 of C. glabrata in the absence of fluconazole.

This result confirms the resistant phenotype of the strain Tg5 of C. glabrata with respect to fluconazole.

This result was confirmed by that obtained with the Etest method. In fact, with this method an MIC greater than 256 µg/ml was obtained, and the interpretation by the EUCAST and CLSI tables made it possible to determine that, with an MIC greater than 32 µg/ml for fluconazole, this strain is resistant to this antifungal agent.

Example 7: Test of Sensitivity of the Strain Tg5 of C. glabrata to Voriconazole

The strain Tg5 of C. glabrata was cultivated as described in paragraph I of the Examples section so as to obtain an inoculum at $3 \times 10^6$ CFU/ml in 15 ml of RPMI medium.

2 ml of voriconazole solution prepared in the RPMI medium were then added to 1 ml of this inoculum so as to obtain a final concentration of yeast of $10^6$ CFU/ml and of 8 µg/ml in voriconazole.

The inoculum was treated in the same way so as to obtain cultures of $10^6$ CFU/ml and the following concentrations of voriconazole: 0.007 µg/ml, 0.015 µg/ml, 0.031 µg/ml, 0.062 µg/ml, 0.125 µg/ml, 0.25 µg/ml, 0.5 µg/ml, 1 µg/ml, 2 µg/ml, 4 µg/ml, 8 µg/ml.

A control without voriconazole was also prepared by adding 2 ml of RPMI medium.

After incubation for 6.5 h at 35° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of voriconazole and without voriconazole.

The data obtained was then averaged for each different tested condition and was presented in the form of a graph, shown in FIG. 7, where the solid curve shows the change in chitin level as a function of the concentration of voriconazole.

A decrease in the chitin level of less than 20% in the wall of the cells of the strain Tg5 of *C. glabrata* in the presence of voriconazole was observed compared to the chitin level of cells of the strain Tg5 of *C. glabrata* in the absence of voriconazole.

This result confirms the resistant phenotype of the strain Tg5 of *C. glabrata* with respect to voriconazole.

This result was confirmed by that obtained with the Etest method. In fact, with this method an MIC of 8 µg/ml was obtained, and the interpretation by the EUCAST table made it possible to determine that, with an MIC greater than 0.5 µg/ml for voriconazole, this strain is resistant to this antifungal agent.

Example 8: Test of Sensitivity of the Strain ATCC®7349 of *C. tropicalis* to Fluconazole The strain ATCC®7349 of *C. tropicalis* was cultivated as described in paragraph I of the Examples section so as to obtain an inoculum at $3 \times 10^6$ CFU/ml in 15 ml of SC medium.

2 ml of fluconazole solution prepared in the SC medium were then added to 1 ml of this inoculum so as to obtain a final concentration of yeast of $10^6$ CFU/ml and of 16 µg/ml in fluconazole.

The inoculum was treated in the same way so as to obtain cultures of $10^6$ CFU/ml and the following concentrations of fluconazole: 0.015 µg/ml, 0.031 µg/ml, 0.062 µg/ml, 0.125 µg/ml, 0.25 µg/ml, 0.5 µg/ml, 1 µg/ml, 2 µg/ml, 4 µg/ml, 8 µg/ml, 16 µg/ml.

A control without fluconazole was prepared by adding 2 ml of SC medium.

After incubation for 24 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of fluconazole and without fluconazole.

The data obtained was then averaged for each different tested condition and was presented in the form of a graph, shown in FIG. 8, where the solid curve shows the change in chitin level as a function of the concentration of fluconazole.

An increase having a value greater than or equal to 20% of the chitin level in the wall of the cells of the strain ATCC®7349 of *C. tropicalis* in the presence of fluconazole was observed compared to the chitin level of a population of cells of the strain ATCC®7349 of *C. tropicalis* in the absence of fluconazole.

The number of cells for each triplicate of each condition of concentration of fluconazole and without fluconazole was then determined by high-content analysis (HCA) microscopy, as described in paragraph II of the Examples section.

The data obtained was then averaged for each different tested condition and was presented in the form of a graph, shown in FIG. 8, where the dashed curve shows the change in the number of cells as a function of the concentration of fluconazole.

A decrease of at least 0.3 log of the number of cells of the strain ATCC®7349 of *C. tropicalis* as a function of the concentration of fluconazole in the medium was observed compared to the number of cells of the strain ATCC®7349 of *C. tropicalis* in a population of cells in the absence of fluconazole.

These results confirm the sensitive phenotype of the strain ATCC®7349 of *C. tropicalis* with respect to fluconazole.

This result was confirmed by that obtained with the Etest method. In fact, with this method an MIC of 0.38 µg/ml was obtained, and the interpretation by the EUCAST and CLSI tables made it possible to determine that, with an MIC lower than 2 µg/ml for fluconazole, this strain is sensitive to this antifungal agent.

Example 9: Test of Sensitivity of the Strain ATCC®7349 of *C. tropicalis* to Voriconazole The strain ATCC®7349 of *C. tropicalis* was cultivated as described in paragraph I of the Examples section so as to obtain an inoculum at $3 \times 10^6$ CFU/ml in 15 ml of SC medium.

2 ml of voriconazole solution prepared in the SC medium were then added to 1 ml of this inoculum so as to obtain a final concentration of yeast of $10^6$ CFU/ml and of 5 µg/ml in voriconazole.

The inoculum was treated in the same way so as to obtain cultures of $10^6$ CFU/ml and the following concentrations of voriconazole: 0.004 µg/ml, 0.009 µg/ml, 0.019 µg/ml, 0.039 µg/ml, 0.078 µg/ml, 0.156 µg/ml, 0.312 µg/ml, 0.625 µg/ml, 1.25 µg/ml, 2.5 µg/ml, 5 µg/ml.

A control without voriconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of voriconazole and without voriconazole.

The data obtained was then averaged for each tested condition and was presented in the form of a graph, shown in FIG. 9, where the solid curve shows the change in chitin level as a function of the concentration of voriconazole.

An increase having a value greater than or equal to 20% of the chitin level in the wall of the cells of the strain ATCC®7349 of *C. tropicalis* in the presence of voriconazole was observed compared to the chitin level of a population of cells of the strain ATCC®7349 of *C. tropicalis* in the absence of voriconazole.

The number of cells for each triplicate of each condition of concentration of antifungal agent and without antifungal agent was then determined by high-content analysis (HCA) microscopy, as described in paragraph II of the Examples section.

The data obtained was then averaged for each tested condition and was presented in the form of a graph, shown in FIG. 9, where the dashed curve shows the change in the number of cells as a function of the concentration of voriconazole.

A decrease of at least 0.3 log of the number of cells of the strain ATCC®7349 of *C. tropicalis* as a function of the concentration of voriconazole in the medium was observed compared to the number of cells of the strain ATCC®7349 of *C. tropicalis* in a population of cells in the absence of voriconazole.

These results confirm the sensitive phenotype of the strain ATCC®7349 of *C. tropicalis* with respect to voriconazole.

This result was confirmed by that obtained with the Etest method. In fact, with this method an MIC of 0.023 µg/ml was obtained, and the interpretation by the EUCAST and CLSI tables made it possible to determine that, with an MIC lower than 0.12 µg/ml for voriconazole, this strain is sensitive to this antifungal agent.

Example 10: Test of Sensitivity of the Strain ATCC®7349 of C. tropicalis to Micafungin The strain ATCC®7349 of C. tropicalis was cultivated as described in paragraph I of the Examples section so as to obtain an inoculum at $3\times10^6$ CFU/ml in 15 ml of SC medium.

2 ml of micafungin solution prepared in the SC medium were then added to 1 ml of this inoculum so as to obtain a final concentration of yeast of $10^6$ CFU/ml and of 1 µg/ml in micafungin.

The inoculum was treated in the same way so as to obtain cultures of $10^6$ CFU/ml and the following concentrations of fluconazole: 0.0009 µg/ml, 0.019 µg/ml, 0.039 µg/ml, 0.007 µg/ml, 0.015 µg/ml, 0.031 µg/ml, 0.062 µg/ml, 0.125 µg/ml, 0.25 µg/ml, 0.5 µg/ml, 1 µg/ml.

A control without voriconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of micafungin and without micafungin.

The data obtained was then averaged for each different tested condition and was presented in the form of a graph, shown in FIG. 10, where the solid curve shows the change in chitin level as a function of the concentration of micafungin.

An increase having a value greater than or equal to 20% of the chitin level in the wall of the cells of the strain ATCC®7349 of C. tropicalis in the presence of micafungin was observed compared to that of cells in the absence of micafungin.

The number of cells for each triplicate of each condition of concentration of micafungin and without micafungin was then determined by high-content analysis (HCA) microscopy, as described in paragraph II of the Examples section.

The data obtained was then averaged for each different tested condition and was presented in the form of a graph, shown in FIG. 10, where the dashed curve shows the change in the number of cells as a function of the concentration of micafungin.

A decrease of at least 0.3 log of the number of cells of the strain ATCC®7349 of C. tropicalis as a function of the concentration of micafungin in the medium was observed compared to the number of cells in a population of cells in the absence of micafungin.

These results confirm the sensitive phenotype of the strain ATCC®7349 of C. tropicalis with respect to micafungin.

This result was confirmed by that obtained with the Etest method. In fact, with this method an MIC of 0.016 µg/ml was obtained, and the interpretation by the CLSI table made it possible to determine that, with an MIC lower than 0.25 µg/ml for micafungin, this strain is sensitive to this antifungal agent.

Example 11: Test of Sensitivity of the Strain 13/5 of C. tropicalis to Micafungin The strain 13/5 of C. tropicalis was cultivated as described in paragraph I of the Examples section so as to obtain an inoculum at $3\times10^6$ CFU/ml in 15 ml of SC medium.

2 ml of micafungin solution prepared in the SC medium were then added to 1 ml of this inoculum so as to obtain a final concentration of yeast of $10^6$ CFU/ml and of 1 µg/ml in micafungin.

The inoculum was treated in the same way so as to obtain cultures of $10^6$ CFU/ml and the following concentrations of fluconazole: 0.0009 µg/ml, 0.019 µg/ml, 0.039 µg/ml, 0.007 µg/ml, 0.015 µg/ml, 0.031 µg/ml, 0.062 µg/ml, 0.125 µg/ml, 0.25 µg/ml, 0.5 µg/ml, 1 µg/ml.

A control without voriconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of micafungin and without micafungin.

The data obtained was then averaged for each different tested condition and was presented in the form of a graph, shown in FIG. 11, where the solid curve shows the change in chitin level as a function of the concentration of micafungin.

An increase in the chitin level of less than 10% in the wall of the cells of the strain 13/5 of C. tropicalis in the presence of micafungin was observed compared to the chitin level of cells of the strain 13/5 of C. tropicalis in the absence of micafungin.

This result confirms the resistant phenotype of the strain 13/5 of C. tropicalis with respect to micafungin.

This result was confirmed by that obtained with the Etest method. In fact, with this method an MIC of 1.5 µg/ml was obtained, and the interpretation by the CLSI table made it possible to determine that, with an MIC greater than 0.5 µg/ml for micafungin, this strain is resistant to this antifungal agent.

Example 12: Test of Sensitivity of the Strain ATCC®22019 of C. parapsilosis to Fluconazole The strain ATCC®22019 of C. parapsilosis was cultivated as described in paragraph I of the Examples section so as to obtain an inoculum at $3\times10^6$ CFU/ml in 15 ml of SC medium.

2 ml of fluconazole solution prepared in the SC medium were then added to 1 ml of this inoculum so as to obtain a final concentration of yeast of $10^6$ CFU/ml and of 16 µg/ml in fluconazole.

The inoculum was treated in the same way so as to obtain cultures of $10^6$ CFU/ml and the following concentrations of fluconazole: 0.015 µg/ml, 0.031 µg/ml, 0.062 µg/ml, 0.125 µg/ml, 0.25 µg/ml, 0.5 µg/ml, 1 µg/ml, 2 µg/ml, 4 µg/ml, 8 µg/ml, 16 µg/ml.

A control without fluconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 μl of CFW were then added to each well.

The chitin level in the cell wall of the yeasts was then measured by high-contact analysis (HCA) microscopy, as described in paragraph II of the Examples section, in triplicate for each condition of concentration of fluconazole and without fluconazole.

The data obtained was then averaged for each different tested condition and was presented in the form of a graph, shown in FIG. 12, where the solid curve shows the change in chitin level as a function of the concentration of fluconazole.

An increase having a value greater than or equal to 20% of the chitin level in the wall of the cells of the strain ATCC®22019 of *C. parapsilosis* in the presence of fluconazole was observed compared to the chitin level of a population of cells of the strain ATCC®22019 of *C. parapsilosis* in the absence of fluconazole.

The number of cells for each triplicate of each condition of concentration of fluconazole and without fluconazole was then determined by high-content analysis (HCA) microscopy, as described in paragraph II of the Examples section.

The data obtained was then averaged for each different tested condition and was presented in the form of a graph, shown in FIG. 12, where the dashed curve shows the change in the number of cells as a function of the concentration of fluconazole.

A decrease of at least 0.3 log of the number of cells of the strain ATCC®22019 of *C. parapsilosis* as a function of the concentration of fluconazole in the medium was observed compared to the number of cells in a population of cells in the absence of fluconazole.

These results confirm the sensitive phenotype of the strain ATCC®22019 of *C. parapsilosis* with respect to fluconazole.

This result was confirmed by that obtained with the Etest method. In fact, with this method an MIC of 1 μg/ml was obtained, and the interpretation by the EUCAST and CLSI tables made it possible to determine that, with an MIC lower than 2 μg/ml for fluconazole, this strain is sensitive to this antifungal agent.

Example 13: Test of Sensitivity of the Strain ATCC®22019 of *C. parapsilosis* to Voriconazole The strain ATCC®22019 of *C. parapsilosis* was cultivated as described in paragraph I of the Examples section so as to obtain an inoculum at $3 \times 10^6$ CFU/ml in 15 ml of SC medium.

2 ml of voriconazole solution prepared in the SC medium were then added to 1 ml of this inoculum so as to obtain a final concentration of yeast of $10^6$ CFU/ml and of 5 μg/ml in voriconazole.

The inoculum was treated in the same way so as to obtain cultures of $10^6$ CFU/ml and the following concentrations of voriconazole: 0.004 μg/ml, 0.009 μg/ml, 0.019 μg/ml, 0.039 μg/ml, 0.078 μg/ml, 0.156 μg/ml, 0.312 μg/ml, 0.625 μg/ml, 1.25 μg/ml, 2.5 μg/ml, 5 μg/ml.

A control without voriconazole was prepared by adding 2 ml of SC medium.

After incubation for 6.5 h at 30° C. with stirring at 200 rpm, 100 μl of each culture were removed and transferred to 96-well plates. This procedure was performed in triplicate, and 2.5 μl of CFW were then added to each well.

The chitin level in the cell wall of the yeasts was then measured by high-contact analysis (HCA) microscopy, as described in paragraph II of the Examples section, in triplicate for each condition of concentration of voriconazole and without voriconazole.

The data obtained was then averaged for each different tested condition and was presented in the form of a graph, shown in FIG. 13, where the solid curve shows the change in chitin level as a function of the concentration of voriconazole.

An increase having a value greater than or equal to 20% of the chitin level in the wall of the cells of the strain ATCC®22019 of *C. parapsilosis* in the presence of voriconazole was observed compared to the chitin level of a population of cells of the strain ATCC®22019 of *C. parapsilosis* in the absence of voriconazole.

The number of cells for each triplicate of each condition of concentration of voriconazole and without voriconazole was then determined by high-content analysis (HCA) microscopy, as described in paragraph II of the Examples section.

The data obtained was then averaged for each different tested condition and was presented in the form of a graph, shown in FIG. 13, where the dashed curve shows the change in the number of cells as a function of the concentration of voriconazole.

A decrease of at least 0.3 log of the number of cells of the strain ATCC®22019 of *C. parapsilosis* as a function of the concentration of antifungal agent in the medium was observed compared to the number of cells in a population of cells of the strain ATCC®22019 of *C. parapsilosis* in the absence of antifungal agent.

These results confirm the sensitive phenotype of the strain ATCC®22019 of *C. parapsilosis* with respect to voriconazole.

This result was confirmed by that obtained with the Etest method. In fact, with this method an MIC of 0.023 μg/ml was obtained, and the interpretation by the EUCAST and CLSI tables made it possible to determine that, with an MIC lower than 0.12 μg/ml for voriconazole, this strain is sensitive to this antifungal agent.

Example 14: Test of Sensitivity of the Strain ATCC®22019 of *C. parapsilosis* to Micafungin The strain ATCC®22019 of *C. parapsilosis* was cultivated as described in paragraph I of the Examples section so as to obtain an inoculum at $3 \times 10^6$ CFU/ml in 15 ml of SC medium.

2 ml of micafungin solution prepared in the SC medium were then added to 1 ml of this inoculum so as to obtain a final concentration of yeast of $10^6$ CFU/ml and of 1 μg/ml in micafungin.

The inoculum was treated in the same way so as to obtain cultures of $10^6$ CFU/ml and the following concentrations of fluconazole: 0.0009 μg/ml, 0.019 μg/ml, 0.039 μg/ml, 0.007 μg/ml, 0.015 μg/ml, 0.031 μg/ml, 0.062 μg/ml, 0.125 μg/ml, 0.25 μg/ml, 0.5 μg/ml, 1 μg/ml.

A control without voriconazole was prepared by adding 2 ml of SC medium.

After incubation for 24 h at 30° C. with stirring at 200 rpm, 100 μl of each culture were removed and transferred to 96-well plates. This procedure was performed in triplicate, and 2.5 μl of CFW were then added to each well.

The chitin level in the cell wall of the yeasts was then measured by high-contact analysis (HCA) microscopy, as described in paragraph II of the Examples section, in triplicate for each condition of concentration of micafungin and without micafungin.

The data obtained was then averaged for each different tested condition and was presented in the form of a graph, shown in FIG. 15, where the solid curve shows the change in chitin level as a function of the concentration of micafungin.

An increase having a value greater than or equal to 20% of the chitin level in the wall of the cells of the strain ATCC®22019 of *C. parapsilosis* in the presence of micafungin was observed compared to the chitin level of cells of the strain ATCC®22019 of *C. parapsilosis* in the absence of micafungin.

The number of cells for each triplicate of each condition of concentration of micafungin and without micafungin was then determined by high-content analysis (HCA) microscopy, as described in paragraph II of the Examples section.

The data obtained was then averaged for each different tested condition and was presented in the form of a graph, shown in FIG. 14, where the dashed curve shows the change in the number of cells as a function of the concentration of micafungin.

A decrease of at least 0.3 log of the number of cells of the strain ATCC®22019 of *C. parapsilosis* as a function of the concentration of micafungin in the medium was observed compared to the number of cells in a population of cells of the strain ATCC®22019 of *C. parapsilosis* in the absence of micafungin.

These results confirm the sensitive phenotype of the strain ATCC®22019 of *C. parapsilosis* with respect to micafungin.

This result was confirmed by that obtained with the Etest method. In fact, with this method an MIC of 0.19 µg/ml was obtained, and the interpretation by the CLSI table made it possible to determine that, with an MIC lower than 2 µg/ml for micafungin, this strain is sensitive to this antifungal agent.

Example 15: Test of Sensitivity of the Strain 8/21 of *C. parapsilosis* to Fluconazole The strain 8/21 of *C. tropicalis* was cultivated as described in paragraph I of the Examples section so as to obtain an inoculum at 3×10⁶ CFU/ml in 15 ml of SC medium.

2 ml of fluconazole solution prepared in the SC medium were then added to 1 ml of this inoculum so as to obtain a final concentration of yeast of 10⁶ CFU/ml and of 16 µg/ml in fluconazole.

The inoculum was treated in the same way so as to obtain cultures of 10⁶ CFU/ml and the following concentrations of fluconazole: 0.015 µg/ml, 0.031 µg/ml, 0.062 µg/ml, 0.125 µg/ml, 0.25 µg/ml, 0.5 µg/ml, 1 µg/ml, 2 µg/ml, 4 µg/ml, 8 µg/ml, 16 µg/ml.

A control without fluconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of fluconazole and without fluconazole.

The data obtained was then averaged for each different tested condition and was presented in the form of a graph, shown in FIG. 15, where the solid curve shows the change in chitin level as a function of the concentration of fluconazole.

An increase in the chitin level of less than 10% in the wall of the cells of the strain 8/21 of *C. parapsilosis* in the presence of fluconazole was observed compared to the chitin level of cells of the strain 8/21 of *C. parapsilosis* in the absence of fluconazole.

This result confirms the resistant phenotype of the strain 8/21 of *C. parapsilosis* with respect to fluconazole.

This result was confirmed by that obtained with the Etest method. In fact, with this method an MIC of 8 µg/ml was obtained, and the interpretation by the EUCAST and CLSI tables made it possible to determine that, with an MIC greater than 4 µg/ml for fluconazole, this strain is resistant to this antifungal agent.

Example 16: Test of Sensitivity of the Strain 8/21 of *C. parapsilosis* to Voriconazole The strain 8/21 of *C. tropicalis* was cultivated as described in paragraph I of the Examples section so as to obtain an inoculum at 3×10⁶ CFU/ml in 15 ml of SC medium.

2 ml of voriconazole solution prepared in the SC medium were then added to 1 ml of this inoculum so as to obtain a final concentration of yeast of 10⁶ CFU/ml and of 5 µg/ml in voriconazole.

The inoculum was treated in the same way so as to obtain cultures of 10⁶ CFU/ml and the following concentrations of voriconazole: 0.004 µg/ml, 0.009 µg/ml, 0.019 µg/ml, 0.039 µg/ml, 0.078 µg/ml, 0.156 µg/ml, 0.312 µg/ml, 0.625 µg/ml, 1.25 µg/ml, 2.5 µg/ml, 5 µg/ml.

A control without voriconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of voriconazole and without voriconazole.

The data obtained was then averaged for each different tested condition and was presented in the form of a graph, shown in FIG. 16, where the solid curve shows the change in chitin level as a function of the concentration of voriconazole.

An increase in the chitin level of less than 10% in the wall of the cells of the strain 8/21 of *C. parapsilosis* in the presence of voriconazole was observed compared to the chitin level of cells of the strain 8/21 of *C. parapsilosis* in the absence of voriconazole.

This result confirms the resistant phenotype of the strain 8/21 of *C. parapsilosis* with respect to voriconazole.

This result was confirmed by that obtained by means of the Etest method, and the interpretation by the EUCAST table made it possible to determine that, with an MIC of 4 µg/ml for voriconazole, this strain is resistant to this antifungal agent.

This result was confirmed by that obtained with the Etest method. In fact, with this method an MIC of 4 µg/ml was obtained, and the interpretation by the EUCAST and CLSI tables made it possible to determine that, with an MIC greater than 0.12 μg/ml and greater than 0.5 μg/ml respectively for voriconazole, this strain is resistant to this antifungal agent.

Example 17: Test of Sensitivity of the Strain ATCC®6258 of *C. krusei* to Fluconazole The strain ATCC®6258 of *C. krusei* was cultivated as described in paragraph I of the Examples section so as to obtain an inoculum at $3 \times 10^6$ CFU/ml in 15 ml of SC medium.

2 ml of fluconazole solution prepared in the SC medium were then added to 1 ml of this inoculum so as to obtain a final concentration of yeast of $10^6$ CFU/ml and of 128 μg/ml in fluconazole.

The inoculum was treated in the same way so as to obtain cultures of $10^6$ CFU/ml and the following concentrations of fluconazole: 0.125 μg/ml, 0.25 μg/ml, 0.5 μg/ml, 1 μg/ml, 2 μg/ml, 4 μg/ml, 8 μg/ml, 16 μg/ml, 32 μg/ml, 64 μg/ml, 128 μg/ml.

A control without fluconazole was prepared by adding 2 ml of SC medium.

After incubation for 6.5 h at 30° C. with stirring at 200 rpm, 100 μl of each culture were removed and transferred to 96-well plates. This procedure was performed in triplicate, and 2.5 μl of CFW were then added to each well.

The chitin level in the cell wall of the yeasts was then measured by high-contact analysis (HCA) microscopy, as described in paragraph II of the Examples section, in triplicate for each condition of concentration of fluconazole and without fluconazole.

The data obtained was then averaged for each different tested condition and was presented in the form of a graph, shown in FIG. 17, where the solid curve shows the change in chitin level as a function of the concentration of fluconazole.

An increase in the chitin level of less than 10% in the wall of the cells of the strain ATCC®6258 of *C. krusei* in the presence of fluconazole was observed compared to the chitin level of cells of the strain ATCC®6258 of *C. krusei* in the absence of fluconazole.

This result confirms the resistant phenotype of the strain ATCC®6258 of *C. krusei* with respect to fluconazole.

This result was confirmed by that obtained with the Etest method. In fact, with this method an MIC of 64 μg/ml was obtained, and the interpretation by the EUCAST table made it possible to determine that, with an MIC greater than 32 μg/ml for fluconazole, this strain is resistant to this antifungal agent. The interpretation was obtained in this case by extrapolation of the EUCAST and CLSI data for *C. glabrata*.

Example 18: Test of Sensitivity of the Strain ATCC®6258 of *C. krusei* to Voriconazole The strain ATCC®6258 of *C. krusei* was cultivated as described in paragraph I of the Examples section so as to obtain an inoculum at $3 \times 10^6$ CFU/ml in 15 ml of RPMI medium.

2 ml of voriconazole solution prepared in the RPMI medium were then added to 1 ml of this inoculum so as to obtain a final concentration of yeast of $10^6$ CFU/ml and of 8 μg/ml in voriconazole.

The inoculum was treated in the same way so as to obtain cultures of $10^6$ CFU/ml and the following concentrations of voriconazole: 0.007 μg/ml, 0.015 μg/ml, 0.031 μg/ml, 0.062 μg/ml, 0.125 μg/ml, 0.25 μg/ml, 0.5 μg/ml, 1 μg/ml, 2 μg/ml, 4 μg/ml, 8 μg/ml.

A control without voriconazole was also prepared by adding 2 ml of RPMI medium.

After incubation for 24 h at 30° C. with stirring at 200 rpm, 100 μl of each culture were removed and transferred to 96-well plates. This procedure was performed in triplicate, and 2.5 μl of CFW were then added to each well.

The chitin level in the cell wall of the yeasts was then measured by high-contact analysis (HCA) microscopy, as described in paragraph II of the Examples section, in triplicate for each condition of concentration of voriconazole and without voriconazole.

The data obtained was then averaged for each different tested condition and was presented in the form of a graph, shown in FIG. 18, where the solid curve shows the change in chitin level as a function of the concentration of voriconazole.

An increase having a value greater than or equal to 20% of the chitin level in the wall of the cells of the strain ATCC®6258 of *C. krusei* in the presence of voriconazole was observed compared to the chitin level of a population of cells of the strain ATCC®6258 of *C. krusei* in the absence of voriconazole.

The number of cells for each triplicate of each condition of concentration of voriconazole and without voriconazole was then determined by high-content analysis (HCA) microscopy, as described in paragraph II of the Examples section.

The data obtained was then averaged for each different tested condition and was presented in the form of a graph, shown in FIG. 18, where the dashed curve shows the change in the number of cells as a function of the concentration of voriconazole.

A decrease of less than 0.3 log of the number of cells of the strain ATCC®6258 of *C. krusei* as a function of the concentration of antifungal agent in the medium was observed compared to the number of cells in a population of cells of the strain ATCC®6258 of *C. krusei* in the absence of antifungal agent.

This result confirms the intermediate phenotype of the strain ATCC®6258 of *C. krusei* with respect to voriconazole.

This result was confirmed by that obtained with the Etest method. In fact, with this method an MIC of 1 μg/ml was obtained, and the interpretation by the CLSI table made it possible to determine that, with an MIC equal to 1 μg/ml for voriconazole, this strain has an intermediate phenotype with respect to this antifungal agent.

Example 19: Test of Sensitivity of the Strain GRE32 of *C. krusei* to Fluconazole The strain GRE32 of *C. krusei* was cultivated as described in paragraph I of the Examples section so as to obtain an inoculum at $3 \times 10^6$ CFU/ml in 15 ml of SC medium.

2 ml of fluconazole solution prepared in the SC medium were then added to 1 ml of this inoculum so as to obtain a final concentration of yeast of $10^6$ CFU/ml and of 128 μg/ml in fluconazole.

The inoculum was treated in the same way so as to obtain cultures of $10^6$ CFU/ml and the following concentrations of fluconazole: 0.125 μg/ml, 0.25 μg/ml, 0.5 μg/ml, 1 μg/ml, 2 μg/ml, 4 μg/ml, 8 μg/ml, 16 μg/ml, 32 μg/ml, 64 μg/ml, 128 μg/ml.

A control without fluconazole was prepared by adding 2 ml of SC medium.

After incubation for 6.5 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of fluconazole and without fluconazole.

The data obtained was then averaged for each different tested condition and was presented in the form of a graph, shown in FIG. 19, where the solid curve shows the change in chitin level as a function of the concentration of fluconazole.

A decrease in the chitin level of less than 20% in the wall of the cells of the strain GRE32 of *C. krusei* in the presence of fluconazole was observed compared to the chitin level of cells of the strain GRE32 of *C. krusei* in the absence of fluconazole.

This result confirms the resistant phenotype of the strain GRE32 of *C. krusei* with respect to fluconazole.

This result was confirmed by that obtained with the Etest method. In fact, with this method an MIC of 64 µg/ml was obtained, and the interpretation by the EUCAST table made it possible to determine that, with an MIC greater than 32 µg/ml for fluconazole, this strain is resistant to this antifungal agent. The interpretation was obtained in this case by extrapolation of the EUCAST and CLSI data for *C. glabrata*.

Example 20: Test of Sensitivity of the Strain GRE32 of *C. krusei* to Voriconazole The strain GRE32 of *C. krusei* was cultivated as described in paragraph I of the Examples section so as to obtain an inoculum at $3 \times 10^6$ CFU/ml in 15 ml of SC medium.

2 ml of voriconazole solution prepared in the RPMI medium were then added to 1 ml of this inoculum so as to obtain a final concentration of yeast of $10^6$ CFU/ml and of 8 µg/ml in voriconazole.

The inoculum was treated in the same way so as to obtain cultures of $10^6$ CFU/ml and the following concentrations of voriconazole: 0.007 µg/ml, 0.015 µg/ml, 0.031 µg/ml, 0.062 µg/ml, 0.125 µg/ml, 0.25 µg/ml, 0.5 µg/ml, 1 µg/ml, 2 µg/ml, 4 µg/ml, 8 µg/ml.

A control without voriconazole was also prepared by adding 2 ml of RPMI medium.

After incubation for 24 h at 30° C. with stirring at 200 rpm, 100 µl of each culture were removed and transferred to 96-well plates. This procedure was performed in triplicate, and 2.5 µl of CFW were then added to each well.

The chitin level in the cell wall of the yeasts was then measured by high-contact analysis (HCA) microscopy, as described in paragraph II of the Examples section, in triplicate for each condition of concentration of voriconazole and without voriconazole.

The data obtained was then averaged for each different tested condition and was presented in the form of a graph, shown in FIG. 20, where the solid curve shows the change in chitin level as a function of the concentration of voriconazole.

An increase in the chitin level greater than or equal to 20% in the wall of the cells of the strain GRE32 of *C. krusei* in the presence of voriconazole was observed compared to the chitin level of cells of the strain GRE32 of *C. krusei* in the absence of voriconazole.

The number of cells for each triplicate of each condition of concentration of voriconazole and without voriconazole was then determined by high-content analysis (HCA) microscopy, as described in paragraph II of the Examples section.

The data obtained was then averaged for each different tested condition and was presented in the form of a graph, shown in FIG. 20, where the dashed curve shows the change in the number of cells as a function of the concentration of voriconazole.

A decrease of less than 0.3 log of the number of cells of the strain GRE32 of *C. krusei* as a function of the concentration of voriconazole in the medium was observed compared to the number of cells in a population of cells of the strain GRE32 of *C. krusei* in the absence of voriconazole.

These results confirm the intermediate phenotype of the strain GRE32 of *C. krusei* with respect to voriconazole.

This result was confirmed by that obtained with the Etest method. In fact, with this method an MIC of 1 µg/ml was obtained, and the interpretation by the CLSI table made it possible to determine that, with an MIC equal to 1 µg/ml for voriconazole, this strain has an intermediate phenotype with respect to this antifungal agent.

B—Examples of Multicellular Fungi

I—Culture of Multicellular Fungus in the Presence of an Antifungal Agent

The strains of multicellular fungus were incubated beforehand at 30° C. overnight in a yeast extract medium—peptone dextrose (YPD) (1% bacto peptone, 0.5% yeast extract, 2% glucose, 1.5% agar).

Multicellular fungus conidia were then removed from YPD medium plates and suspended in a 0.9% NaCl saline solution, in which the cell concentration was estimated by optical microscopy using Kova counting slides.

A dilution was performed to obtain a final inoculum at $10^6$ CFU/ml, in a synthetic complete (SC) medium at pH 7 (2% glucose, 0.5% ammonium sulfate, 0.17% nitrogen-containing yeast base, 0.2% synthetic complete mixture, and 10% HEPES 1.5M pH 7.2) a or an RPMI medium depending on the fungus, from the genera *Aspergillus, Fusarium, Scedosporium, Lichteimia, Rhizopus, Rhizomucor, Mucor, Paecylomyces*, and the species *Aspergillus fumigatus, Aspergillus flavus, Aspergillus niger, Aspergillus nidulans, Aspergillus terreus, Fusarium solani, Fusarium oxysporum, Scedosporium apiospermum, Scedosporium prolificans, Mucor racemosa, Lichteimia corymbifera, Rhizopus oryzae, Rhizomucor pusillus*, so as to obtain a final yeast concentration of $10^6$ CFU/ml and the desired concentration of antifungal agent according to table 3.

TABLE 3

Gradients of concentration (μg/ml) of fluconazole, posaconazole, voriconazole, itraconazole, isavuconazole for the class of azoles and micafungin, anidulafungin and caspofungin for the class of class of echinocandins, and amphotericin B and nystatin for the class of polyenes, for the species of multicellular fungus.

| Antifungal agent | Concentration (μg/ml) | | | | | | | | | | |
|---|---|---|---|---|---|---|---|---|---|---|---|
| fluconazole | 8 | 4 | 2 | 1 | 0.5 | 0.25 | 0.125 | 0.062 | 0.031 | 0.015 | 0.007 |
| posaconazole | | | | | | | | | | | |
| voriconazole | | | | | | | | | | | |
| isavuconazole | | | | | | | | | | | |
| amphotericin B | | | | | | | | | | | |
| nystatin | | | | | | | | | | | |
| micafungin | 2 | 1 | 0.5 | 0.25 | 0.125 | 0.062 | 0.031 | 0.015 | 0.007 | 0.003 | 0.0017 |
| anidulafungin | | | | | | | | | | | |
| caspofungin | | | | | | | | | | | |

After homogenisation, the cultures were placed at 30° C. at 200 rpm and incubated for a period of 4 h, 6 h or 24 h.

II—Examination by High-Content Analysis (HCA) Microscopy

After incubation, the culture of fungi obtained above were transferred in triplicate to 96-well plates, and 2.5 μl of Calcofluor White (CFW) were added to each well so as to mark the chitin of the cell walls of the conidia and vegetative germination hyphae.

A step of acquiring images by automated fluorescence microscopy (ScanR screening station, Olympus), using a 40× lens and a CFW filter, make it possible to obtain 30 images per well so as to capture enough conidia and vegetative germination hyphae to provide measurements of the length of the germinative hyphae and the proportion of conidia yielding germinative hyphae. These images were analysed by ScanR analysis software (Olympus). Firstly, the background noise was processed so as to improve the contrast between the fluorescence of the conidia and germinative hyphae and background noise. A pixel threshold was then defined. Segmentation of the fluorescent elements present in each of the acquired images was then performed using an algorithm predefined in the software, making it possible to determine the limit of this element on the basis of the fluorescence intensity of each element. A parameter of size was then applied so as to select the conidia and the germinative hyphae and measure the length of these germinative hyphae.

For each element then corresponding to a conidia or a germinative hyphae, it was thus possible, on the basis of these elements predefined beforehand, to define the fluorescence intensity for each of these elements, this intensity being directly correlated with the chitin content of their wall.

This data was then processed by a software (GraphPad Prism) so as to provide a representation in the form of a graph showing the change in the chitin level of the wall of the conidia and vegetative hyphae and the change in the length of the vegetative hyphae as a function of the concentration of antifungal agent, for each strain of multicellular fungus-antifungal agent pairing.

When an increase in the chitin level having a value less than 10% or a decrease in the chitin level of less than 20% or an unchanged chitin level are observed compared to the chitin level of a population of cells of said fungus in the absence of antifungal agent, the strain is assumed to have the resistant phenotype.

When an increase in the chitin level having a value of from 10% to a value less than 20% is observed compared to the chitin level of a population of cells of said fungus in the absence of antifungal agent, the strain is assumed to have the intermediate phenotype.

When an increase in the chitin level greater than or equal to 20% is observed compared to the chitin level of a population of cells of said fungus in the absence of antifungal agent, as well as a decrease in the length of the germinative hyphae of less than 10% or an unchanged length of the germinative hyphae compared to the length of germinative hyphae in a population of cells of said fungus in the absence of antifungal agent, the strain is assumed to have the intermediate phenotype.

When an increase in the chitin level greater than or equal to 20% is observed compared to the chitin level of a population of cells of said fungus in the absence of antifungal agent, as well as a decrease in the length of germinative hyphae of at least 10% compared to the number of cells in a population of cells of said fungus in the absence of antifungal agent, the strain is assumed to have the sensitive phenotype.

The consideration of a parameter other than the cell count for determining the sensitivity of a strain of fungus constitutes the uniqueness of this invention compared to existing tests based on a measurement of fungus growth, these being subject to the subjectivity of the reader.

III—Analysis by the Comparative Etest® Method, Marketed by Biomérieux

The Etest® method is a commercial test for determining the sensitivity of a strain, most frequently used routinely in clinical mycology laboratories.

The results obtained by HCA were compared with those obtained with this susceptibility test.

The Etest® tests were performed according to the manufacturer's instructions. After distributing a standardised Mac Farland 0.5 inoculum (equivalent of $10^8$ CFU/ml) over plates of RPMI medium, said plates were incubated for 24 h at 35° C. so as to be able to determine the minimum inhibitory concentration (MIC).

The results of the MICs obtained were interpreted according to the tables of EUCAST (European Committee on Antimicrobial Susceptibility Testing www.eucast.org) which list the clinical thresholds (CBPs) for the most common species of multicellular fungi of the genus *Aspergillus* as a function of different antifungal agents. There are currently no interpretation criteria for the other genera of multicellular fungi including *Fusarium, Scedosporium, Lichteimia, Rhizopus, Rhizomucor, Mucor, Paecylomyces*.

The MIC thus makes it possible to determine the sensitivity of a strain to an antifungal agent. The CBPs or clinical thresholds make it possible to interpret this MIC and to predict a failure of therapy in the patient. The CBPs make it possible to establish the following categories: sensitive, intermediate, and resistant.

If the value of the MIC is in the sensitive category, the likelihood of failure of the treatment is low. This likelihood increases in the intermediate and resistant categories.

These tables make it possible to detect the acquired resistances which result primarily from the selection of mutants subjected to the pressure of pharmaceutical products in patients. They are thus specific to strains and should not be confused with intrinsic resistances, which are specific to species.

The invention claimed is:

1. A method for determining a degree of sensitivity of a population of cells of a strain of fungus capable of being stained by Calcofluor White to an antifungal agent,
    wherein the degree of sensitivity is determined by determining a possible change in a chitin level in cell walls of the population of cells of the strain of fungus, said possible change being determined by comparing a chitin level in cell walls of the population of cells in the presence of the antifungal agent to a chitin level in cells walls of the population of the cells in the absence of the antifungal agent,
    wherein the antifungal agent is capable of provoking a parietal stress that leads to an accumulation of the chitin in the cell walls of the population of cells to compensate for damage induced by the antifungal agent, and
    wherein the degree of sensitivity corresponds to a sensitive phenotype, or a resistant phenotype, or an intermediate phenotype of said strain of fungus with respect to the antifungal agent,
    the method comprising:
    (a) a step of contacting the population of cells of said strain of fungus with a gradient of concentrations of the antifungal agent varying from 0.0009 to 130 ug/ml, at a temperature of from 30 to 35 degrees C., for a period of time less than or equal to 48 h, so as to obtain a mixture of cells of said strain of fungus and antifungal agent;
    (b) a step of adding the fluorescent marker Calcofluor White to the mixture of cells of said strain of fungus and antifungal agent obtained previously, so as to obtain a mixture of cells of said strain of fungus, labelled by Calcofluor White, and antifungal agent;
    (c) a step of quantifying the chitin level, by high-content analysis fluorescence microscopy, of the labelled cells of said strain of fungus in the mixture obtained in the previous step;
    (d) a step of determining the possible change in the chitin level in the mixture of cells of said strain of fungus, labelled by Calcofluor White, and antifungal agent as a function of the concentrations of antifungal agent in the population of cells of said strain of fungus compared to the chitin level of a population of cells of said strain of fungus in the absence of antifungal agent; and
    in the case in which said possible change in the chitin level is an increase in the chitin level greater than or equal to 20%, said step d is followed by
    (e) a step of counting the cells in the mixture of cells of said strain of fungus, labelled by Calcofluor White, and antifungal agent; then by
    (f) a step of determining the possible change in the number of cells as a function of the concentration of antifungal agent in the population of cells of said strain of fungus compared to the number of cells in a population of cells of said strain of fungus in the absence of antifungal agent;
    when said change in the chitin level of said step d is an increase in the chitin level of less than 10% or a decrease in the chitin level, or the level is unchanged, it is concluded that said strain of fungus has a resistant phenotype;
    when said change in the chitin level of said step d is an increase of from 10% to a value less than 20%, it is concluded that said strain of fungus has an intermediate phenotype;
    when said change in the chitin level of said step d is an increase by a value greater than or equal to 20%, and when said change in the number of cells of said step f is a decrease of less than 0.3 log or an unchanged number of cells, it is concluded that said strain of fungus has an intermediate phenotype; and
    when said change in the chitin level of said step d is an increase by a value greater than or equal to 20%, and when said change in the number of cells is a decrease of at least 0.3 log, it is concluded that said strain of fungus has a sensitive phenotype.

2. The method according to claim 1, further comprising determining a possible change in a length of vegetative germination hypha in said population of cells of said strain of fungus to determine the degree of sensitivity of said strain of fungus to the antifungal agent, said change in the length of the vegetative germination hypha being determined by comparing a length of vegetative germination hypha in said population of cells of said strain of fungus in the presence of the antifungal agent to a length of vegetative germination hypha of the population of cells of said strain of fungus in the absence of the antifungal agent, and wherein said fungus is a multicellular fungus.

3. The method according to claim 1, said fungus being an unicellular fungus and
    wherein the resistant phenotype of said strain of fungus with respect to said antifungal agent is determined by an increase in the chitin level of less than 10%, or a decrease in the chitin level, or an unchanged chitin level compared to the chitin level of a population of cells of said strain of fungus in the absence of antifungal agent, and wherein the minimum threshold of cells in said population of cells of said strain of fungus demonstrating an increase in the chitin level is at least 10%,
    or wherein the intermediate phenotype of said strain of fungus with respect to said antifungal agent is determined either by an increase in the chitin level of from 10% to a value less than 20% compared to the chitin level of a population of cells of said strain of fungus in the absence of antifungal agent, or by an increase in the chitin level greater than or equal to 20% compared to the chitin level of a population of cells of said strain of fungus in the absence of antifungal agent, and by a decrease in the number of cells of less than 0.3 log or an unchanged number of cells compared to the number of cells of a population of cells of said strain of fungus in the absence of antifungal agent, and wherein the minimum threshold of cells in said population of cells of said strain of fungus demonstrating an increase in the chitin level is at least 10%,
    or wherein the sensitive phenotype of said strain of fungus with respect to said antifungal agent is determined by an increase in the chitin level greater than or equal to 20% compared to the chitin level of a population of cells of said strain of fungus in the absence of antifungal agent, and by a decrease in the number of cells of at least 0.3 log compared to the number of cells of a population of cells of said strain of fungus in the absence of antifungal agent, and wherein the minimum threshold of cells in said population of cells of said strain of fungus demonstrating an increase in the chitin level is at least 10%, and wherein the minimum level of a decrease in the number of cells in said population of cells of said strain of fungus is at least 0.3 log.

4. The method according to claim 1, wherein the antifungal agent is selected from the group consisting of antifungal agents free from polyenes and antifungal agents that inhibit the synthesis of ergosterol.

5. The method according to claim 1, wherein the fungus is a yeast selected from the group consisting of the genera *Candida, Cryptococcus, Saccharomyces, Trichosporon, Rhodotorula*, and *Malassezia*.

6. The method according to claim 1, wherein said fungus is a unicellular fungus.

7. The method according to claim 1, wherein said degree of sensitivity corresponds to the resistant phenotype when the change in the chitin level in the population of cells of said strain of fungus in the presence of the antifungal agent is an increase in the chitin level of less than 10%, or a decrease in the chitin level, or an unchanged chitin level compared to the chitin level of a population of cells of said strain of fungus in the absence of antifungal agent, and wherein the minimum threshold of cells in said population of cells of said strain of fungus demonstrating an increase in the chitin level is at least 10%;

wherein said degree of sensitivity corresponds to the intermediate phenotype when the change in the chitin level in the population of cells of said strain of fungus in the presence of the antifungal agent is either (1) an increase in the chitin level of from 10% to a value less than 20% compared to the chitin level of a population of cells of said strain of fungus in the absence of the antifungal agent, or (2) an increase in the chitin level greater than or equal to 20% compared to the chitin level of a population of cells of said strain of fungus in the absence of the antifungal agent and the change in the number of cells of said strain of fungus in the presence of the antifungal agent is a decrease of less than 0.3 log or an unchanged number of cells compared to the number of cells in a population of cells of said strain of fungus in the absence of the antifungal agent, and for both (1) and (2) wherein the minimum threshold of cells in said population of cells of said strain of fungus demonstrating an increase in the chitin level is at least 10%; and wherein said degree of sensitivity corresponds to the sensitive phenotype when the change in the chitin level in the population of cells of said strain of fungus in the presence of antifungal agent is an increase in the chitin level greater than or equal to 20% compared to the chitin level of a population of cells of said strain of fungus in the absence of the antifungal agent, and the change in the number of cells in said population of cells of said strain of fungus in the presence of the antifungal agent is a decrease in the number of cells of at least 0.3 log compared to the number of cells of a population of cells of said strain of fungus in the absence of the antifungal agent, and the minimum threshold of cells in said population of cells of said strain of fungus demonstrating an increase in the chitin level is at least 10%.

8. The method according to claim 4, wherein said fungus is a multicellular fungus, further comprising a step of determining a possible change in a length of vegetative germination hypha in said population of fungal cells in the presence of said antifungal agent, said possible change in the length of the vegetative germination hypha being determined compared to a length of vegetative germination hypha of the population of cells of said strain of fungus in the absence of said antifungal agent.

9. The method of claim 1, wherein a treatment of an infection of the strain of fungus is adapted based on whether it is concluded that the strain of fungus is the resistant phenotype, the intermediate phenotype, or the sensitive phenotype.

* * * * *